(12) United States Patent
Molnar

(10) Patent No.: US 12,257,387 B2
(45) Date of Patent: Mar. 25, 2025

(54) MEDICAL DEVICES FOR AIRWAY MANAGEMENT AND METHODS OF PLACEMENT

(71) Applicant: WM & DG, Inc., Deerfield, IL (US)

(72) Inventor: Robert Molnar, Long Grove, IL (US)

(73) Assignee: WM & DG, INC., Deerfield, IL (US)

( * ) Notice: Subject to any disclaimer, the term of this patent is extended or adjusted under 35 U.S.C. 154(b) by 3 days.

(21) Appl. No.: 16/156,322

(22) Filed: Oct. 10, 2018

(65) Prior Publication Data

US 2020/0114105 A1 Apr. 16, 2020

(51) Int. Cl.
| | |
|---|---|
| *A61M 16/04* | (2006.01) |
| *A61B 1/00* | (2006.01) |
| *A61B 1/05* | (2006.01) |
| *A61B 1/267* | (2006.01) |
| *A61B 7/02* | (2006.01) |
| *A61M 16/08* | (2006.01) |
| *A61M 25/06* | (2006.01) |

(52) U.S. Cl.
CPC ..... *A61M 16/0488* (2013.01); *A61B 1/00016* (2013.01); *A61B 1/00045* (2013.01); *A61B 1/00154* (2013.01); *A61B 1/051* (2013.01); *A61B 1/267* (2013.01); *A61B 7/023* (2013.01); *A61M 16/0429* (2014.02); *A61M 16/0434* (2013.01); *A61M 16/0816* (2013.01); *A61M 25/0668* (2013.01); *A61M 2205/3368* (2013.01)

(58) Field of Classification Search
CPC ........ A61M 16/0402; A61M 16/07404; A61M 16/0463; A61M 16/0488; A61M 16/04; A61B 1/267; A61B 1/2673; A61B 1/2676

USPC .................................................. 600/234–246
See application file for complete search history.

(56) References Cited

U.S. PATENT DOCUMENTS

| | | | |
|---|---|---|---|
| 4,231,365 | A | 11/1980 | Scarberry |
| 4,360,008 | A | 11/1982 | Corazzelli, Jr. |

(Continued)

FOREIGN PATENT DOCUMENTS

| | | |
|---|---|---|
| EP | 0665029 A2 | 8/1995 |
| JP | 2016516455 A | 6/2016 |

(Continued)

OTHER PUBLICATIONS

PCT International Search Report for Application No. PCT/US2019/055138 dated Feb. 3, 2020.

(Continued)

*Primary Examiner* — Matthew J Lawson
(74) *Attorney, Agent, or Firm* — Greer, Burns & Crain, Ltd.

(57) ABSTRACT

This disclosure relates to various aspects of an adaptor for converting a medical device, including an endotracheal tube and/or a bougie, into a device compatible with a camera. In some embodiments, the adaptor comprising a first hollow tube with a distal end opening and a proximal end opening, the first hollow tube having a diameter compatible for insertion of the medical device into the first hollow tube, wherein the adaptor further comprises a camera sealed or attached slidably along the first hollow tube and/or the adaptor comprises a second hollow tube attached along the length of the first hollow tube, the second hollow tube being capable of receiving a camera and/or a medical tool, and wherein the second hollow tube is not sealed at the distal end.

2 Claims, 24 Drawing Sheets

(56) References Cited

U.S. PATENT DOCUMENTS

| | | |
|---|---|---|
| 4,577,638 A | 3/1986 | Graham |
| 4,584,998 A | 4/1986 | McGrail |
| 4,607,643 A | 8/1986 | Bell et al. |
| 4,846,153 A | 7/1989 | Berci |
| 5,052,386 A | 1/1991 | Fischer, Jr. |
| 5,025,778 A | 6/1991 | Silverstein et al. |
| 5,174,283 A | 12/1992 | Parker |
| 5,193,692 A | 3/1993 | Farley et al. |
| 5,241,956 A | 9/1993 | Brain |
| 5,353,787 A | 10/1994 | Price |
| 5,372,131 A | 12/1994 | Heinen, Jr. |
| 5,400,771 A | 3/1995 | Pirak et al. |
| 5,499,625 A | 3/1996 | Frass et al. |
| 5,511,916 A | 4/1996 | Farley et al. |
| 5,513,627 A | 5/1996 | Flam |
| 5,515,844 A | 5/1996 | Christopher |
| 5,551,947 A | 9/1996 | Kaali |
| 5,632,271 A | 5/1997 | Brain |
| 5,665,052 A | 9/1997 | Bullard |
| 5,682,880 A | 11/1997 | Brain |
| 5,733,242 A | 3/1998 | Rayburn et al. |
| 5,740,791 A | 4/1998 | Aves |
| 5,819,733 A | 10/1998 | Bertram |
| 5,879,306 A | 3/1999 | Fontenot et al. |
| 5,888,195 A | 3/1999 | Schneider |
| 6,038,629 A | 3/2000 | Ogilvie et al. |
| 6,115,523 A | 9/2000 | Choi et al. |
| 6,142,144 A | 11/2000 | Pacey |
| 6,189,533 B1 | 2/2001 | Simon et al. |
| 6,196,225 B1 | 3/2001 | Allgeyer |
| 6,349,720 B1 | 2/2002 | Clark |
| 6,386,199 B1 | 5/2002 | Alfery |
| 6,439,232 B1 | 8/2002 | Brain |
| 6,440,061 B1 | 8/2002 | Wenner et al. |
| 6,443,156 B1 | 9/2002 | Niklason et al. |
| 6,527,704 B1 | 3/2003 | Chang et al. |
| 6,543,447 B2 | 4/2003 | Pacey |
| 6,626,169 B2 | 9/2003 | Gaitini |
| 6,631,720 B1 | 10/2003 | Brain |
| 6,634,354 B2 | 10/2003 | Christopher |
| 6,655,377 B2 | 12/2003 | Pacey |
| 6,860,264 B2 | 3/2005 | Christopher |
| 6,860,270 B2 | 3/2005 | Sniadach |
| 6,918,391 B1 | 7/2005 | Moore |
| 7,052,456 B2 | 5/2006 | Simon |
| 7,128,509 B2 | 10/2006 | Farley et al. |
| 7,156,091 B2 | 1/2007 | Koyama et al. |
| 7,237,993 B2 | 7/2007 | Farley et al. |
| 7,331,925 B2 | 2/2008 | McMorrow et al. |
| 7,421,877 B2 | 9/2008 | Frenken |
| 7,450,746 B2 | 11/2008 | Yang et al. |
| 7,493,901 B2 | 2/2009 | Brain |
| 7,520,857 B2 | 4/2009 | Chalana et al. |
| 7,527,601 B2 | 5/2009 | Dubey et al. |
| 7,611,466 B2 | 11/2009 | Chalana et al. |
| 7,654,970 B2 | 2/2010 | Dubey |
| 7,713,189 B2 | 5/2010 | Hanke |
| 7,713,216 B2 | 5/2010 | Dubey et al. |
| 7,727,150 B2 | 6/2010 | Chalana et al. |
| 7,744,534 B2 | 6/2010 | Chalana et al. |
| 7,749,165 B2 | 7/2010 | McMorrow et al. |
| 7,749,176 B2 | 7/2010 | Dubey |
| 7,811,239 B2 | 10/2010 | Dubey et al. |
| 7,819,806 B2 | 10/2010 | Yang et al. |
| 7,854,324 B2 | 12/2010 | Farley et al. |
| 7,896,007 B2 | 3/2011 | Brain |
| 7,921,847 B2 | 4/2011 | Totz |
| 7,942,813 B2 | 5/2011 | Mackin |
| 7,976,458 B2 | 7/2011 | Stefanchik et al. |
| 8,016,760 B2 | 9/2011 | Chalana et al. |
| 8,038,629 B2 | 10/2011 | Solanki et al. |
| 8,202,215 B2 | 6/2012 | Xiao et al. |
| 8,215,307 B2 | 7/2012 | Nasir |
| 8,297,275 B2 | 10/2012 | Ogilvie et al. |
| 8,308,644 B2 | 11/2012 | McMorrow et al. |
| 8,371,303 B2 | 2/2013 | Schaner et al. |
| 8,529,442 B2 | 9/2013 | Pacey et al. |
| 8,677,990 B2 | 3/2014 | Gabriel |
| 8,863,746 B2 | 10/2014 | Totz |
| 8,928,746 B1 | 1/2015 | Stevrin et al. |
| 9,211,060 B2 | 12/2015 | Waldron et al. |
| 9,415,179 B2 | 8/2016 | Molnar |
| 9,427,142 B2 | 8/2016 | Terliuc |
| 9,579,012 B2 | 2/2017 | Vazales et al. |
| 9,833,587 B2 | 12/2017 | Cook |
| 10,188,815 B2 | 1/2019 | Manas et al. |
| 10,342,944 B2 | 7/2019 | Molnar |
| 10,441,735 B1 * | 10/2019 | Zhou .................... A61M 16/04 |
| 10,576,230 B2 * | 3/2020 | Esnouf ............. A61M 16/0445 |
| 2002/0108610 A1 | 8/2002 | Christopher |
| 2002/0195103 A1 | 12/2002 | O'Mara |
| 2003/0220542 A1 | 11/2003 | Belson et al. |
| 2005/0182297 A1 | 8/2005 | Gravenstein et al. |
| 2005/0228226 A1 | 10/2005 | Muckner |
| 2005/0244801 A1 | 11/2005 | DeSalvo |
| 2005/0251119 A1 * | 11/2005 | Eaton .................... A61B 90/36 606/15 |
| 2005/0268917 A1 | 12/2005 | Boedeker et al. |
| 2006/0004260 A1 | 1/2006 | Boedeker et al. |
| 2006/0032505 A1 | 2/2006 | Alfery et al. |
| 2006/0111633 A1 | 5/2006 | McMorrow et al. |
| 2006/0149129 A1 | 7/2006 | Watts et al. |
| 2006/0162730 A1 | 7/2006 | Glassenberg et al. |
| 2006/0180155 A1 | 8/2006 | Glassenberg et al. |
| 2006/0276694 A1 | 12/2006 | Acha Gandarias |
| 2007/0017527 A1 * | 1/2007 | Totz ................. A61M 16/0488 128/207.15 |
| 2007/0095351 A1 | 5/2007 | Globel |
| 2007/0106121 A1 | 5/2007 | Yokota et al. |
| 2007/0137651 A1 | 7/2007 | Glassenberg et al. |
| 2007/0156068 A1 | 7/2007 | Dubey |
| 2007/0175482 A1 | 8/2007 | Kimmel et al. |
| 2007/0180887 A1 | 8/2007 | Frenken |
| 2007/0203393 A1 | 8/2007 | Stefanchik |
| 2007/0239197 A1 | 10/2007 | Dubey |
| 2007/0255185 A1 | 11/2007 | Dubey |
| 2007/0293726 A1 * | 12/2007 | Goldfarb ................ A61B 1/233 600/178 |
| 2008/0029100 A1 | 2/2008 | Glassenberg et al. |
| 2008/0114268 A1 | 5/2008 | Dubey |
| 2008/0115783 A1 | 5/2008 | Brain |
| 2008/0146879 A1 | 6/2008 | Pacey |
| 2008/0188774 A1 | 8/2008 | Dubey |
| 2008/0276932 A1 * | 11/2008 | Bassoul ............ A61M 16/0463 128/200.26 |
| 2009/0090356 A1 | 4/2009 | Cook |
| 2009/0194102 A1 | 8/2009 | Chen et al. |
| 2009/0194114 A1 | 8/2009 | Chen et al. |
| 2009/0227835 A1 | 9/2009 | Terliuc |
| 2010/0051024 A1 | 3/2010 | Abrons |
| 2010/0113916 A1 | 5/2010 | Kumar |
| 2010/0147309 A1 | 6/2010 | Cuevas et al. |
| 2010/0204546 A1 | 8/2010 | Hassidov et al. |
| 2010/0249639 A1 | 9/2010 | Bhatt |
| 2010/0261967 A1 | 10/2010 | Pacey et al. |
| 2010/0312069 A1 | 12/2010 | Sutherland et al. |
| 2011/0030694 A1 | 2/2011 | Schaner et al. |
| 2011/0130632 A1 | 6/2011 | McGrail et al. |
| 2011/0137127 A1 | 6/2011 | Schwartz et al. |
| 2011/0178372 A1 | 6/2011 | Pacey et al. |
| 2011/0201882 A1 | 8/2011 | Schwartz et al. |
| 2011/0315147 A1 | 12/2011 | Wood et al. |
| 2012/0059223 A1 | 3/2012 | McGrath et al. |
| 2012/0259173 A1 | 10/2012 | Waldron et al. |
| 2012/0260921 A1 | 10/2012 | Sangwan |
| 2012/0302833 A1 | 11/2012 | Hayman et al. |
| 2013/0006051 A1 | 1/2013 | Stace et al. |
| 2013/0030249 A1 | 1/2013 | Vazales et al. |
| 2013/0096379 A1 | 4/2013 | Golbert |
| 2013/0109918 A1 | 5/2013 | Pagan |
| 2013/0158351 A1 | 6/2013 | Daher et al. |
| 2013/0197303 A1 | 8/2013 | Chun |
| 2013/0253368 A1 | 9/2013 | Are et al. |
| 2013/0324798 A1 | 12/2013 | Molnar et al. |

(56) References Cited

U.S. PATENT DOCUMENTS

| | | |
|---|---|---|
| 2014/0018626 A1 | 1/2014 | Lee |
| 2014/0073853 A1 | 3/2014 | Swisher et al. |
| 2014/0076309 A1 | 3/2014 | Takeda et al. |
| 2014/0096766 A1* | 4/2014 | Avitsian ............... A61B 1/267 128/200.26 |
| 2014/0166020 A1 | 6/2014 | Chang |
| 2014/0194694 A1 | 7/2014 | Chen |
| 2014/0323806 A1 | 10/2014 | Brain |
| 2014/0357951 A1 | 12/2014 | Muller et al. |
| 2015/0122251 A1 | 5/2015 | Azhir et al. |
| 2016/0038008 A1* | 2/2016 | Molnar ............. A61B 1/00137 600/110 |
| 2016/0038014 A1 | 2/2016 | Molnar |
| 2016/0262603 A1* | 9/2016 | Molnar ................. A61B 1/233 |
| 2017/0072154 A1 | 3/2017 | Hoftman et al. |
| 2017/0196445 A1* | 7/2017 | Gardner ............ A61B 1/00154 |
| 2017/0209022 A1* | 7/2017 | Molnar ............ A61M 16/0465 |
| 2018/0104427 A1 | 4/2018 | Avitsian et al. |
| 2018/0169365 A1* | 6/2018 | Sawyer ............ A61M 16/0488 |
| 2019/0059710 A1* | 2/2019 | Molnar ................ A61B 1/2676 |
| 2020/0206445 A1* | 7/2020 | Musuku ............ A61M 16/0488 |
| 2021/0220592 A1* | 7/2021 | Walkden ........... A61M 16/0409 |

FOREIGN PATENT DOCUMENTS

| | | |
|---|---|---|
| KR | 20120095385 | 8/2012 |
| WO | WO9405200 | 3/1994 |
| WO | 03/084719 A2 | 10/2003 |
| WO | 2003084719 | 10/2003 |
| WO | 2008123934 A1 | 10/2008 |
| WO | 2009025843 A1 | 2/2009 |
| WO | WO2010120950 | 10/2010 |
| WO | 2012/080293 A2 | 6/2012 |
| WO | 2013/017535 A2 | 2/2013 |
| WO | 2015013172 | 1/2015 |

OTHER PUBLICATIONS

Bledsoe B., "The Disappearing Endotrachael Tube"., Clinical Professor of Emergency Medicine, University of Nevada School of Medicine, 2009, 84 pages.

Bledso B., "Incubation Threatened by New Devices and Lack of Paramedic Practice", Patient Care, Jems.com; http://www.jems.com/article/patient-care/incubation-threatened-new-devi, printed Feb. 21, 2015, 8 pages.

Bledso B., "Incubation Threatened by New Devices and Lack of Paramedic Practice", Patient Care; http://www.jems.com/article/patient-care/intubation-threatened-new-devi, printed Mar. 20, 2015, 14 pages.

Genzwuerker, MD. et al. "Laryngeal tube: a review of current literature" AJA-Online.com 2011:vol. 12, p. 22-33.

Kodali MD, "Capnography in emergency medicine—911" http://www.capnography.com/outside/922.htm., printed Feb. 21, 2015, 9 pages.

ETView Medical, Ltd., Announces the Appointment of David Amar, MD to Its Scientific Advisory Board, 2012; http://finance.yahoo.com/news/etview-medical-ltd-announces-appointment-104300770.html, Jun. 4, 2012, 3 pages.

ETView, "VivaSight-DL disposable dual lumen airway ventilation tube with integrated high resolution airway imaging system permitting airway control and lung isolation", http://www.etview.com/index_old.php, Jun. 21, 2012. 1 page.

"How to Use a Jem Endotrachael Tube Changer," Endotrachael Tube Changers, Instrumentatio Industries, Inc., Bethal Park, PA, 2015, 2 pages.

ETView Medical Ltd., "ETView Medical, Ltd., Announces Exclusive Patent License Agreement—Feb. 2, 2012", http://worldnetdaily.com.uk/markets/news/read/20671060/etview_medical, Jul. 5, 2012, 3 pages.

Japanese Office Action dated Aug. 1, 2023 for related Japanese Application No. 2021-520326.

* cited by examiner

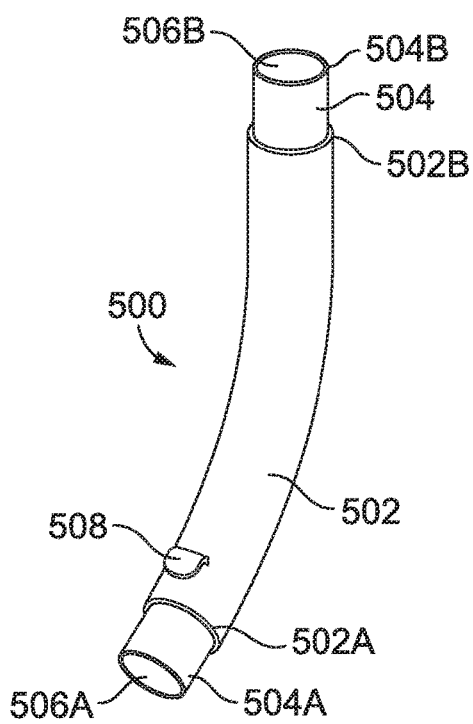
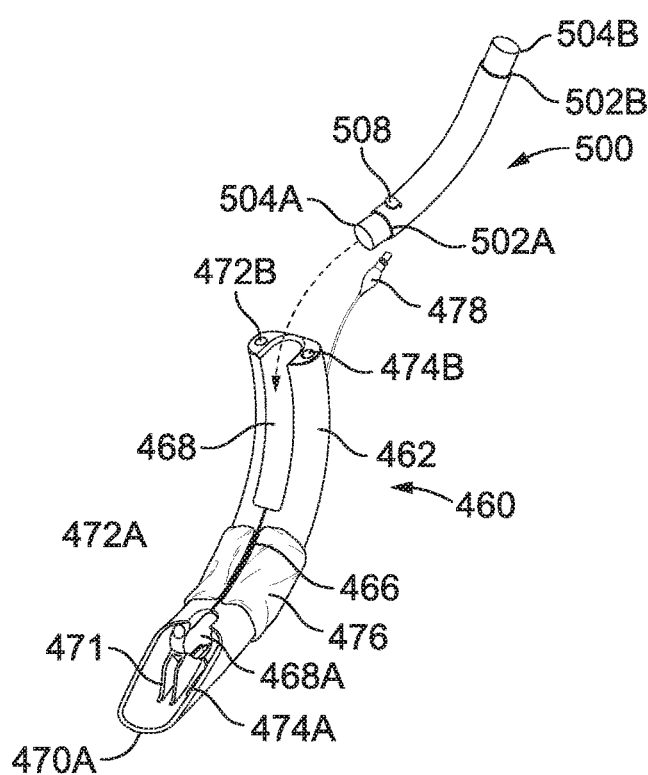
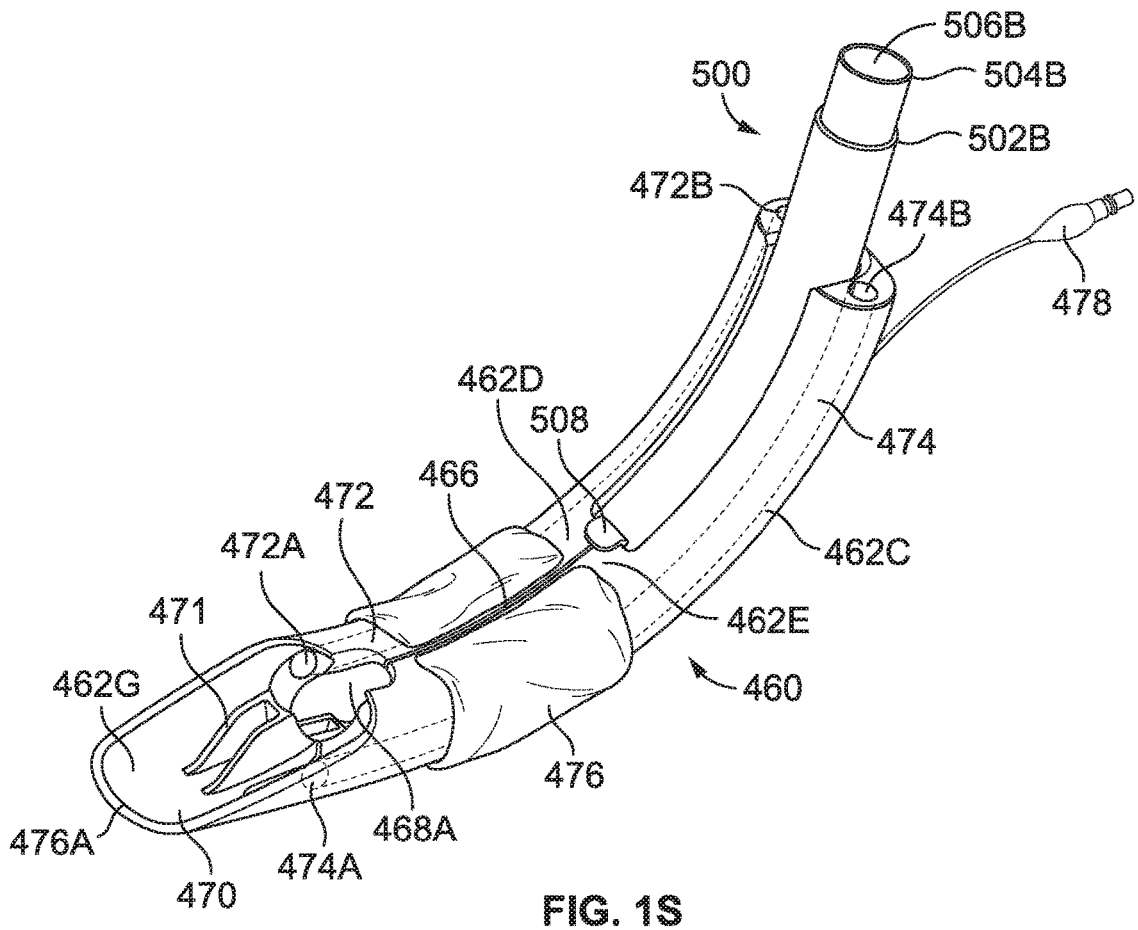
FIG. 1Q
FIG. 1R
FIG. 1S

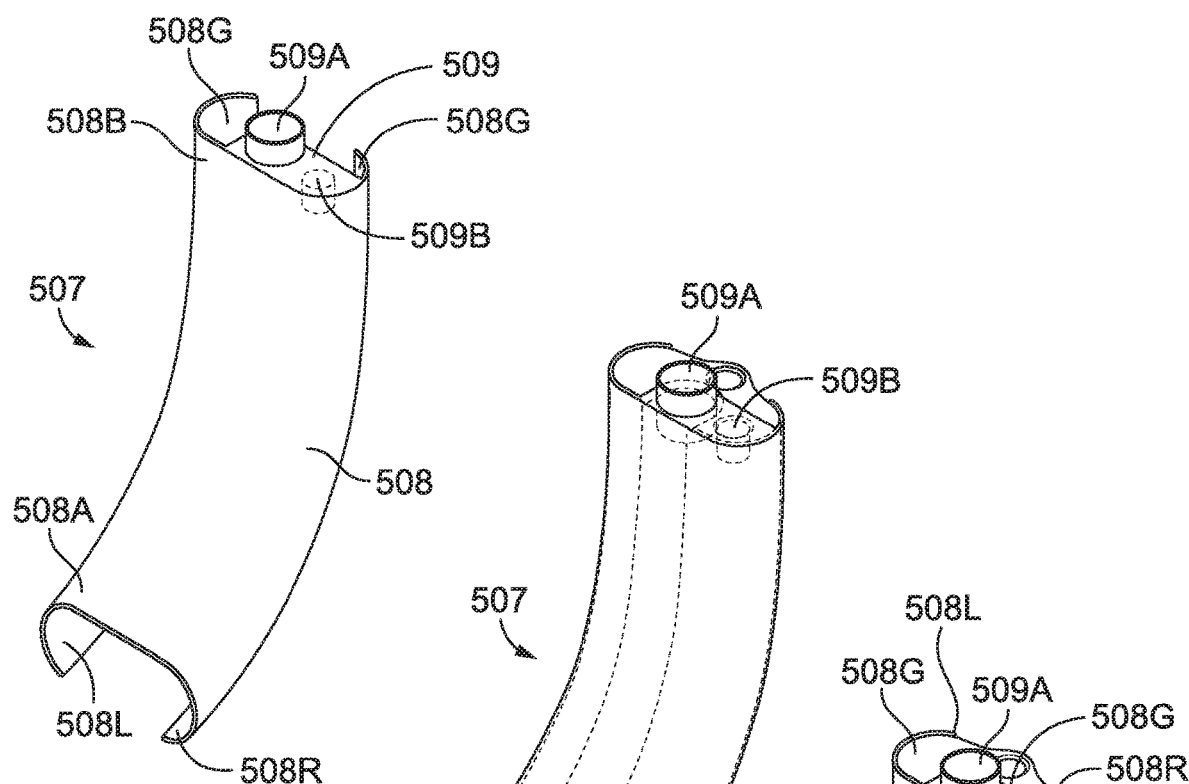
FIG. 1T
FIG. 1U
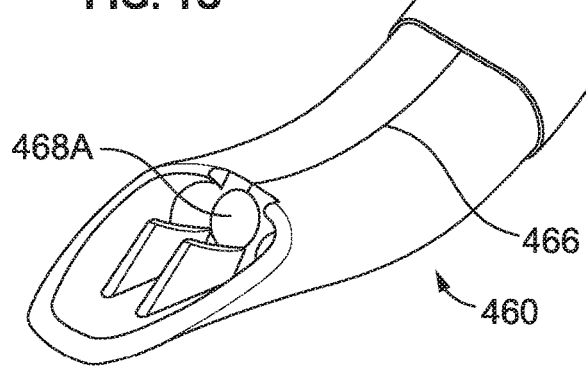
FIG. 1V

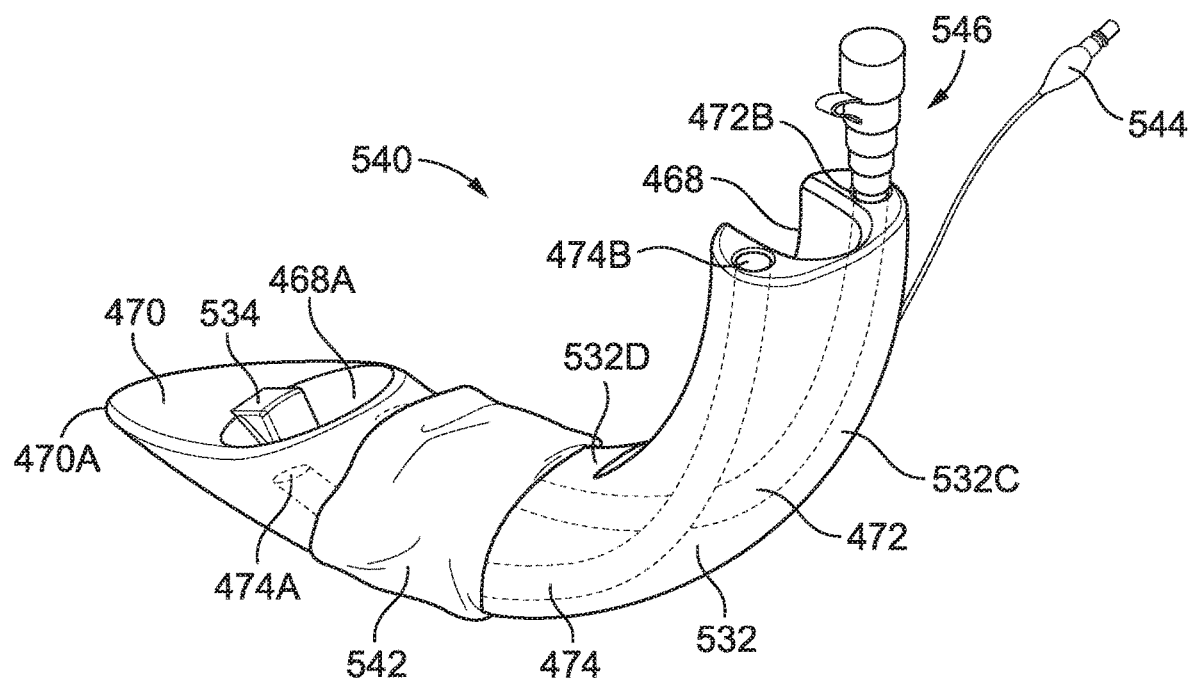
FIG. 4G
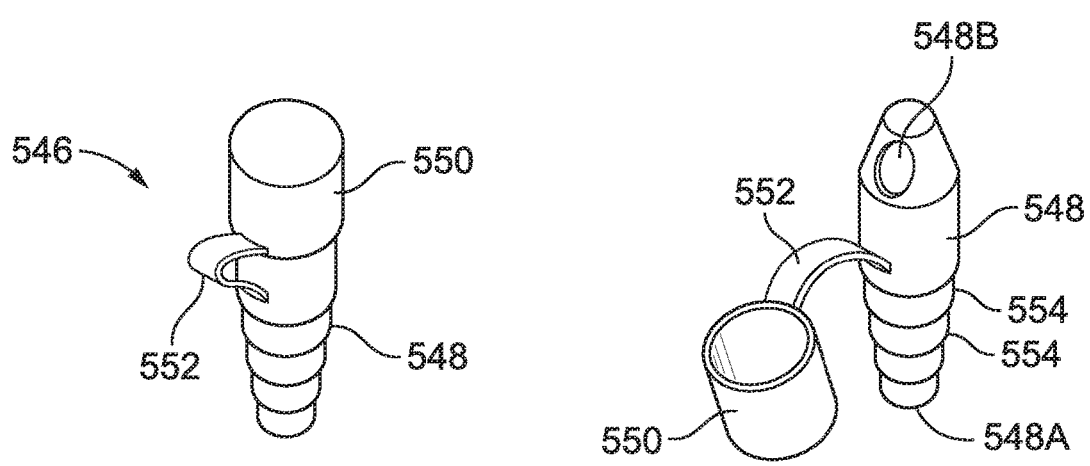
FIG. 4H  FIG. 4I

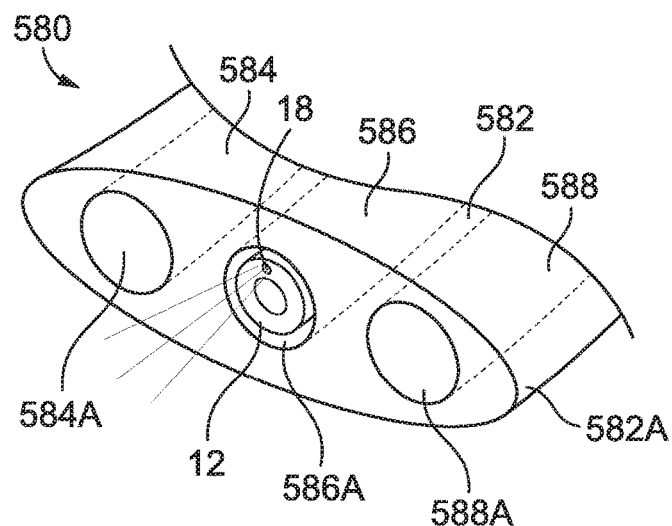
FIG. 5D
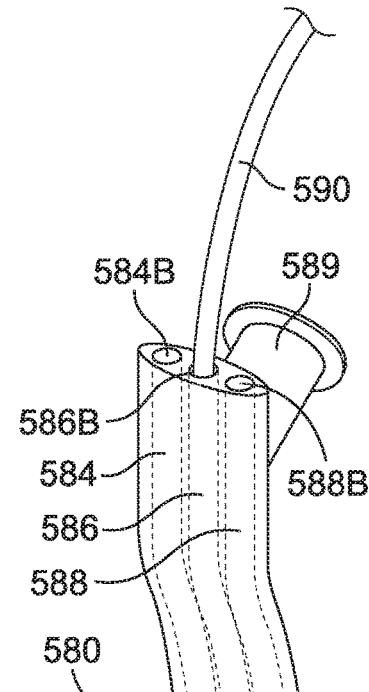
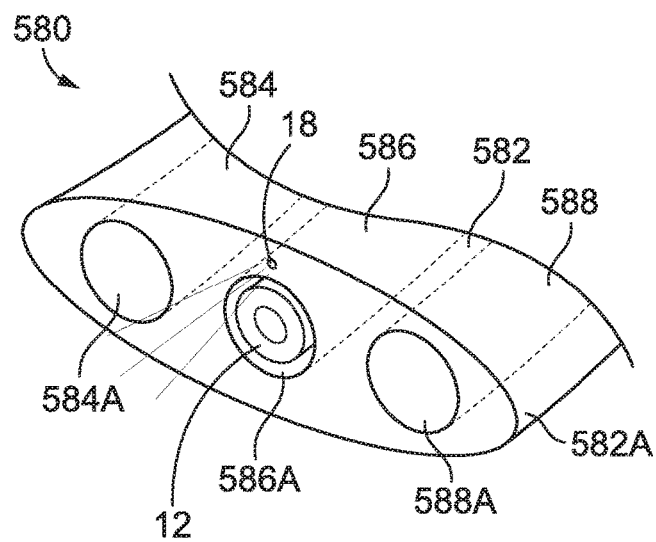
FIG. 5E
FIG. 5F

MEDICAL DEVICES FOR AIRWAY MANAGEMENT AND METHODS OF PLACEMENT

TECHNICAL FIELD

This disclosure relates to the field of medical devices for airway management and provides disposable oral airway management devices, including various oral airway devices and adaptors, which are compatible with a camera, providing continuous visualization and monitoring during and after placement.

BACKGROUND

Various medical devices are available to stabilize a patient and facilitate his/her breathing, feeding and medication delivery. Such devices may be used in patients during surgical procedures, after certain traumas including spinal cord injuries, and in patients suffering from certain medical conditions including advanced Alzheimer's disease. These devices include endotracheal tubes, airway devices, feeding tubes, oral airways, nasal cannulas and many other devices.

A process of placing a breathing tube in a patient is called intubation. Devices such as laryngoscopes, videolaryngoscopes, fiberoptic scopes, as well as other proprietary videoscopes have been developed which are typically used in order to place an endotracheal tube into a patient. These devices may provide accuracy for initial placement, but do not provide continuous visualization or mobility of the image after the endotracheal tube has been placed in the patient. Newer devices, such as Vivasight SL or DL endotracheal tubes, provide continuous visualization, but are costly because they depend on a single use of disposable cameras and they are not transferable from one medical device to another. The Totaltrack VLM supraglottic airway has a proprietary reusable camera for only its one device, and it cannot be transferred to other medical devices.

Certain medical devices which provide continuous visualization are described in U.S. Pat. Nos. 9,357,905, 9,415,179, 9,918,618, and Patent Publications US 2016-0038008; US 2016-0038014; and US 2016-0262603. In these devices, a camera is placed inside of a camera tube which is a separate lumen sealed at the distal end.

However, the need remains for medical devices which can be easily, rapidly and reliably inserted and removed while the devices are also compatible with a camera. There remains the need for devices which can be easily monitored during placement and after the placement has been completed for an adverse reaction in a patient such as for example, airway secretion, apnea, vomiting, internal bleedings, etc.

SUMMARY

The present disclosure provides medical oral airway devices and adaptors which are compatible with a camera and can be used for management of airways and/or intubation of a patient. One practitioner can perform an intubation procedure by using the devices, which eliminates the need for multiple operators and/or excessive lifting force. The use of a laryngoscope may be also avoided. The devices ensure visualization of a patient's larynx and vocal cords during placement, ventilation, intubation and/or extubation. They facilitate a placement, exchange and/or removal procedures without multiple or prolonged attempts. The present medical devices assemble various tools together for a single-step placement and eliminate the need for a multi-step intubation process. The present medical devices can be used for intubating patients who are difficult to intubate and also in at least some of patients with damaged airways. The present medical devices are also suitable for monitoring a patient for an adverse reaction such as for example, vomiting and/or obstruction.

In one aspect, the present disclosure provides an oral airway device which comprises an endotracheal tube (ETT) lumen. This oral airway device comprises a curved tubal body created by a wall which encircles the endotracheal tube (ETT) lumen, wherein the wall has a distal end and proximal end and wherein the wall has a dorsal surface and a ventral surface. The wall comprises two or more hollow channels which are passages in the wall. Each of the channels runs for at least a portion of the wall along the wall distal/proximal axis. Each of the channels has a distal opening which is an outlet from the wall and a proximal opening which is an inlet in the wall. The wall has a slit along the distal/proximal axis and the slit opens in the ETT lumen. The ETT lumen has a distal opening and a proximal opening. The oral airway device may further comprise at least one camera. The at least one camera may be insertable into the hollow channels and/or the ETT lumen, the camera may be built-in the wall of the oral airway device, the camera may be sealed to the wall of the oral airway device, or the camera may be connected slidably along the wall of the oral airway device. The at least one camera may have a capacity to transmit images wirelessly to one or more monitors positioned at one or more remote locations. The at least one camera may transmit images, heart tones, and/or breath sounds wirelessly to one or more monitors positioned at one or more remote locations.

In various embodiments, the oral airway device may further comprise one or more of the following: a bougie insertable into at least one of the hollow channels, a tongue at the distal end of the wall, a ramp being positioned proximally to the tongue, a camera being built-in the ramp, an esophageal stethoscope insertable into the at least one channel, an esophageal stethoscope being built-in the wall, a temperature probe, an inflatable cuff wrapping around the wall in the near proximity to the distal end of the wall, a non-inflatable cuff being attached around the perimeter of the distal end of the wall, a soft cushion being positioned under the tongue, a plug insertable and removable from a proximal opening of at least one of the channels; or any combination thereof.

In some embodiments, the oral airway device comprises two or more cameras, wherein each of the cameras independently:
  being insertable into the hollow channels and the ETT lumen,
  being built-in the wall,
  being sealed to the wall, or
  being connected slidably along the wall.

In some embodiments, the oral airway device comprises three peripheral channels. One of the three channels may have a diameter suitable for receiving and holding a scope.

In some embodiments, the at least one of the hollow channels has a slit and the slit opens into the ETT lumen or to the wall surface.

In some of the oral airway devices, the wall has a recess on the ventral surface of the wall which opens a portion of the ETT lumen on the ventral surface of the wall.

In some embodiments, one of the channels is a camera channel, the camera channel is positioned near the central line of the oral airway device and the ETT lumen is positioned peripherally to the camera channel.

Further aspects of this disclosure provide an oral airway device without the ETT lumen. This oral airway device comprises a curved body being created by a wall which has a distal end and a proximal end, and wherein the curved body comprises one or more peripheral channels which are passages in the wall and which run along the distal-proximal axis of the curved body, wherein each channel has a distal end which is an outlet in the wall and a proximal end which is an inlet in the wall. At least one of the peripheral channels may be a semi-lumen which opens externally along the distal/proximal axis of the curved body. In some embodiments, the oral airway device may further comprise at least one of the following: a cuff at or near the distal end of the curved body, a handle which is adhered to the wall of the curved body in the near proximity to the proximal end of the curved body, a handle which is attached removably to the wall of the curved body in the near proximity to the proximal end of the curved body, or a ventilator cap.

Further aspects of this disclosure provide an adaptor for converting a medical device, such as for example an endotracheal tube, into being compatible with a camera. The adaptor comprises a first hollow tube with a diameter compatible for insertion of the medical device, such as for example an endotracheal tube, into the first hollow tube. The adaptor further comprises a camera being sealed or attached slidably along the first hollow tube and/or the adaptor comprises a second hollow tube being attached along the length of the first hollow tube, the second hollow tube being capable of receiving a camera and/or a medical tool.

In the adaptor, the first hollow tube may comprise a slit. The adaptor may further comprise a second hollow tube and a third hollow tube, the second hollow tube being aligned and attached along the length of the first hollow tube and the third hollow tube being aligned and attached along the length of the first hollow tube. The adaptor may further comprise a backbone rod being attached to at least a portion of the length of the first hollow tube.

Further aspects of this disclosure provide ventilation methods, intubation methods, extubation methods and methods in which an endotracheal tube is exchanged. A method for ventilating a patient may comprise the following steps:
inserting a camera into one of the channels in the oral airway device comprising the ETT lumen, inserting the assembly of the oral airway device with the camera into the patient's oral cavity under continuous visualization by the camera, and positioning the assembly in the patient's pharynx,
establishing a closed system in the assembly, and connecting the assembly to a ventilator.

The method may further comprise inserting at least one of a tool and/or suction tube into one of the channels and wherein the closed system is established by at least one of the following: placing a ventilation adaptor over the wall of the curved body and/or inserting a plug into at least one of the channels.

Further aspects of this disclosure include methods for intubating, extubating or changing an endotracheal tube in a patient. The methods can be conducted under continuous visualization by a camera. The intubation methods comprise a step of loading an endotracheal tube into the ETT lumen of the oral airway device and inserting a camera into one of the channels in the oral airway device. This assembly is then inserted into the patient's oral cavity under continuous visualization by the camera. The assembly is then positioned in the patient's pharynx and the endotracheal tube is placed into the trachea. The assembly is then connected to a ventilator.

In the extubation methods, the endotracheal tube can be removed through the slit in the ETT lumen while the oral airway device remains in place in a patient. If an endotracheal tube needs to be exchanged in an intubated patient, the endotracheal tube can be removed from the ETT lumen through the slit and a new endotracheal tube can be placed, while the oral airway device is still positioned in the patient.

Further aspects of this disclosure provide a system for managing airways in a patient, the system comprising:
the oral airway device with the ETT lumen and the channels and/or the oral airway device with the channels and without the ETT lumen;
a camera insertable and removable from the channels and the ETT lumen; and
a ventilator adaptor with at least one cap for establishing a closed system in the oral airway device.

BRIEF DESCRIPTION OF THE DRAWINGS

FIG. 1Q is a device insertable into the oral airway device of FIGS. 1A and 1B.

FIG. 1R depicts loading the device of FIG. 1Q onto the oral airway device of FIG. 1B.

FIG. 1S depicts the device of FIG. 1Q loaded onto the oral airway device of FIG. 1B.

FIG. 1T depicts a ventilator adaptor for an oral airway device with a slit.

FIG. 1U depicts the ventilator adaptor of FIG. 1T placed over the oral airway device with the slit.

FIG. 1V depicts another embodiment of the ventilator adaptor for an oral airway device with a slit.

FIG. 4G depicts the oral airway device of FIG. 4B from the dorsal surface with a plug inserted into one of the peripheral channels.

FIG. 4H depicts a plug which is capped with a cap.

FIG. 4I depicts the plug of FIG. 4H with the cap being removed.

FIG. 5D depicts the distal end of the oral airway device of FIG. 5A with a camera being inserted into one of the channels.

FIG. 5E depicts the distal end of the oral airway device of FIG. 5A which comprises a light source, with a camera being inserted into one of the channels.

FIG. 5F depicts a bougie being inserted into one of the channels of the oral airway device of FIG. 5A.

DETAILED DESCRIPTION

The present disclosure provides medical devices for airway management, including ventilation, intubation, and monitoring a patient. The present disclosure also provides methods for a rapid and accurate placement of an airway management device in a patient and remote continuous real-time monitoring of the patient after the placement.

The present devices comprise at least one hollow channel with an inlet and outlet. The present devices are compatible with a camera which can be inserted into the channel. Thus, ventilation, intubation and/or extubation of a patient is conducted under continuous visualization. The devices can also monitor heart tones, sound transmission and temperature.

A camera compatible with the present devices may comprise a digital camera coupled to a power cord. The digital camera may comprise CCD (charge-coupled device) and/or CMOS (complementary metal-oxide semiconductor) sensors. The captured images may be transmitted either with a wire or wirelessly. The camera may be also equipped with means for monitoring sounds and heart tones. The camera may be connected to a cable. The camera may transmit images wirelessly to one or more remote locations. Accordingly, a patient can be monitored remotely and from different locations.

In this disclosure, if the same element appears in several different drawings, the element is referred to by the same reference number. It will be appreciated that if an element is described in connection with one embodiment, other embodiments may comprise this element as well. If an element was described in detail in a first embodiment and the element is then referred to under the same reference number in connection with other subsequent embodiments, the description from the first embodiment still applies even if the description is not repeated in full again in connection with the subsequent embodiments.

In one aspect, the present disclosure provides oral airway devices which comprise an endotracheal tube (ETT) lumen for delivering a breathing tube, and one or more additional channels. These oral airway devices with the ETT lumen will now be described with reference to FIGS. 1A-1V, FIG. 2, FIGS. 3A-3C, and FIGS. 4A-4K.

Figure 1A:
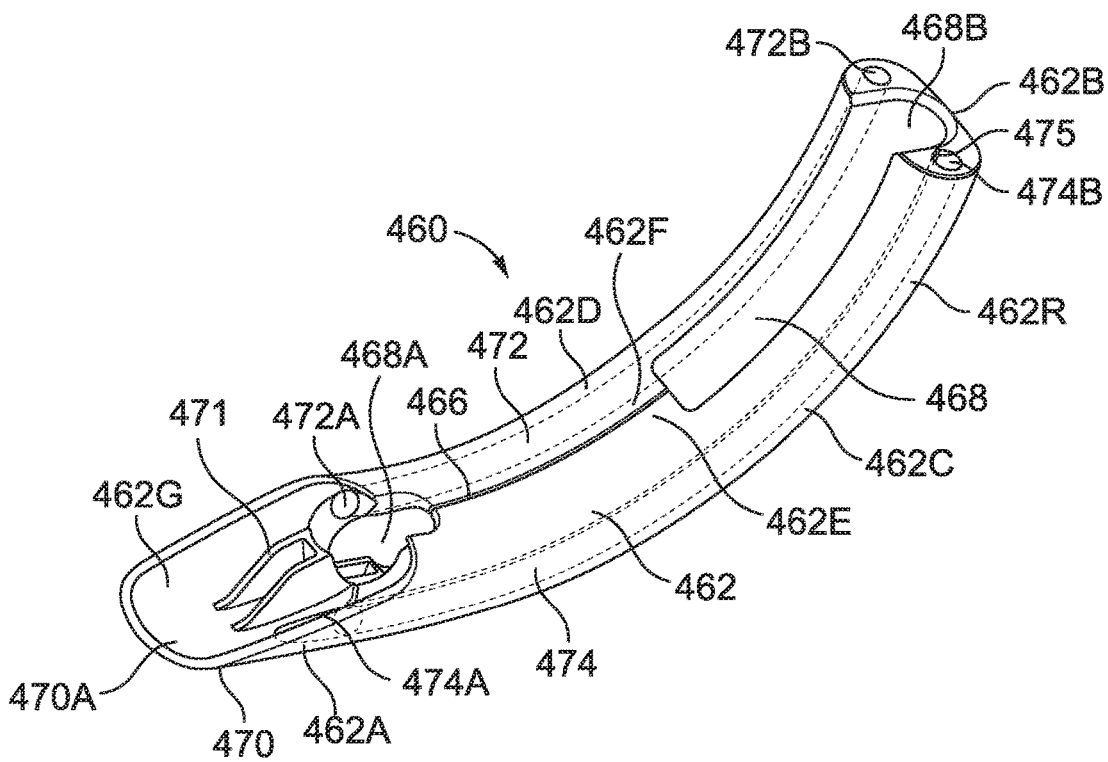
FIG. 1A depicts an oral airway device comprising a peripheral camera channel.

Referring to FIG. 1A, it provides one embodiment of an oral airway device according to this disclosure, generally 460. The oral airway device 460 is a tubal body which is curved such that the oral airway device 460 follows the contour of the roof of a patient's mouth during insertion of the device 460 into the patient.

The curved tubal body of the oral airway device 460 is made by a wall 462 with a distal end 462A and a proximal end 462B.

In this disclosure, "the proximal end of a device" means the end which is the closest to a practitioner during insertion of the device into a patient's body. In this disclosure, "the distal end of a device" means the end which is opposite to the proximal end of the device. The distal end is the end which is inserted first into the patient. The distal end is also considered to be the most distal end to a practitioner during insertion into the patient.

In the oral airway device 460, the wall 462 is curved along the distal-proximal 462A-462B axis such that the wall 462 follows the contour of the roof of a patient's mouth. The wall 462 creates an arch. The wall 462 has a dorsal surface 462C and a ventral surface 462D. Because of the arch curvature, a length of the wall 462 is longer on the dorsal surface, 462C than on the ventral surface, 462D.

The ventral surface 462D is in contact with the patient's tongue when the device 460 during insertion into an oral cavity. The distal surface 462C, is opposite to the ventral surface, 462D.

In this disclosure, the ventral surface of a device is the surface which is in contact with a patient's tongue during the insertion into the patient's oral cavity. The distal surface is the surface which is opposite to the ventral surface. In this disclosure, a lateral surface or a flank is a surface located between the dorsal and ventral surfaces. An oral airway device in this disclosure has two flanks, the left flank and the right flank.

In the drawing of FIG. 1A, the ventral surface 462D and the right flank 462R are shown. The left flank, 462L is opposite to the right flank 462R and is not visible in the drawing of FIG. 1A. In the drawing of FIG. 1A, only a portion of the dorsal surface 462C is visible.

The wall 462 encircles a lumen 468. The lumen 468 is hollow and has a distal opening 468A in proximity to the distal end 462A of the wall 462. The lumen 468 has a proximal opening 468B at the proximal end of the wall 462.

A medical device, such as for example an endotracheal tube or any other tool or device suitable for managing patient's airways, can be placed in the lumen 468 or removed from the lumen 468 by opening the wall 462 along the slit 466 which runs along the distal-proximal axis 462A-462B.

In the embodiment of FIG. 1A, the wall 462 has the slit 466 which runs along the distal-proximal 462A-462B axis on the ventral surface 462D. In other embodiments, the slit 466 may be placed at other surfaces of the wall 462, so long the slit 466 is located such that a practitioner can access the lumen 468 through the slit 466.

The wall 462 is made of a flexible material, such as for example, plastic or rubber. Accordingly, once an endotracheal tube is loaded in the lumen 468, the wall 462 can close back along the slit 466 and it holds the endotracheal tube in place.

Thus, one of the uses for the lumen 468 is to deliver an endotracheal tube during endotracheal placement into a patient. Accordingly, the lumen 468 may be referred in this disclosure as the endotracheal tube (ETT) lumen. However, it will be understood that the ETT lumen 468 may be used for delivery of other breathing tubes and/or tools and/or devices suitable for managing airways. As discussed in more detail below, the ETT lumen 468 itself can be used for ventilating a patient if needed. Accordingly, the device 460 can be used with or without an endotracheal tube for managing airways.

It will be appreciated that in the drawing of FIG. 1A, the ETT lumen 468 is positioned centrally in the curved tubal body of the oral airway device 460. In other embodiments and as discussed in more detail below, the ETT lumen 468 may be positioned peripherally in the curved tubal body of the oral airway device 460.

The oral airway device 460 provides several technical advantages in comparison to conventional oral airway devices which do not have a slit. First, it is much easier to load an endotracheal tube or any other breathing tube or tool or device into the ETT lumen 468 of the oral airway device 460 by opening the wall 462 at the slit 466.

Second, the oral airway device 460 can be separated and removed from a patient after the endotracheal tube has been inserted in the patient and while the endotracheal tube still remains inserted and in place in the patient without the need of removing the whole assembly from the patient first.

In the drawing of FIG. 1A, the wall 462 has two flaps, 462E and 462F, one on each side of the slit 466. The flaps 462E and 462F hold a device, such as for example an endotracheal tube, loaded into the ETT lumen 468 in place and prevent a slippage of an endotracheal tube from the ETT lumen 468 during insertion into a patient.

In other embodiments, the slit 466 may not have flaps. In some embodiments, the edges of the wall 462 may touch at the slit 466. In other embodiments, there is a gap between the edges of the wall 462 at the slit 466.

In the drawing of FIG. 1A, at least some proximal portion of the ETT lumen 468 is not covered by the wall 462 on the ventral surface 462D. Accordingly, some proximal portion of the ETT lumen 468 is exposed on the ventral surface 462D. In other embodiments, where the wall 462 does not have flaps, at least some proximal portion of the ETT lumen may still not be covered by the wall 462. Exposing a portion of the ETT lumen 468 facilitates insertion and removal of an endotracheal tube or other tool/device into and from the ETT lumen 468.

In other embodiments, the slit 466 may still provide access to the ETT lumen 468, but runs all the way or almost all the way from the proximal end 462B to the distal end 462A of the wall 462. In these embodiments, no ETT lumen 468 or only a very minimal portion of it is not covered by the wall 462 on the ventral surface 462D. In these embodiments, (not shown) two or more flaps (not shown) may be positioned on each side of the slit along the distal-proximal 462A-462B axis.

In some other embodiments, the slit 466 may be narrow such that the edges of the wall 462 touch or almost touch along the length of the slit 466. In other embodiments, the slit 466 has a gap such that there is always a gap between the edges of the wall 462 along the slit 466. In the drawing of FIG. 1A, the slit 466 is on the ventral surface 462D. In other embodiments (not shown), the slit 466 still provides access to the ETT lumen, but the slit 466 is positioned on the dorsal surface 462C or at some location other than the ventral surface. For example, between the dorsal and ventral surfaces.

At the distal end 462A, the wall 462 ends with a tongue 470 on the dorsal surface 462C. The distal end 470A of the tongue 470 may be in an oval or round shape. The tongue 470 is tapered at its distal end 470A. The tongue 470 is used to gently push patient's tissues apart during insertion of the oral airway device 460 through the patient's oral cavity and pharynx. The tongue 470 protrudes distally from the wall 462.

There is a ramp 471 attached to the internal surface 462G of the tongue 470. The ramp 471 is positioned proximally to the tongue 470 and distally to the distal opening 468A of the ETT lumen 468.

The ramp 471 elevates above the surface of the internal surface 462G of the tongue. The function of the ramp 471 is to lift and support a distal end of a device loaded in the ETT lumen 468, such as for example an endotracheal tube, above the surface of the internal surface 462G.

The wall 462 has at least two hollow channels, 472 and 474. The channel 472 is a hollow passage in the wall 462. The channel 472 is positioned peripherally to the ETT lumen 468 in the embodiment of FIG. 1A. In other embodiments, the ETT lumen 468 may be positioned peripherally and the channel 472 may be positioned centrally. The channel 472 may be used for inserting a camera or some other tools or devices. Accordingly, the channel 472 may be referred in this disclosure as the camera channel 472. It will be appreciated, that the channel 472 may be used for insertion of other tools and or devices.

The camera channel 472 has a proximal opening 472B which is an inlet into the camera channel 472 and which is positioned at the proximal end 462B of the wall 462. The camera channel 472 runs along the distal-proximal 462A-462B axis of the wall 462. The camera channel 472 ends with a distal opening 472A which is an outlet from the camera channel 472. In the drawing of FIG. 1A, the distal opening 472A is positioned near the distal end 462A of the wall 462. In other embodiments, the length of the camera channel 472 may be shorter and the distal opening 472A may be poisoned anywhere along the length of the wall 462, for example, two-thirds of the wall length.

The distal opening 472A of the camera channel 472 preferably is not sealed such that a camera can protrude distally from the camera channel 472. In some embodiments, the distal opening 472A is sealed with a transparent material (not shown in the drawing of FIG. 1A) such that a camera can capture images through the sealed window while located in the camera channel 472.

A camera (not shown) can be inserted through the proximal opening 472B in the camera channel 472. The camera can protrude from the distal opening 472A of the channel 472. Any camera suitable for visualization of patient's organs can be used in the oral airway device 460. The camera is insertable and removable from the camera channel 472. A position of the camera at the distal opening 472A of the camera channel 472 can be adjusted as needed in order to monitor patient's tissues and passage of the oral airway device 460 through the patient's oral cavity and into a pharynx during placement. The oral airway device 460 when equipped with a camera can provide continuous visualization of patient's larynx and vocal cords. This facilitates an accurate and rapid placement and avoids the need for multiple and lengthy attempts.

In some other embodiments, the oral airway device 460 may comprise at least one camera (not shown) which is built-in the wall 462, sealed to the wall 462 or is connected slidably along the wall 462. In further embodiments, the oral airway device 460 may comprise multiple cameras.

At least one or more cameras may transmit images wirelessly to one or more monitors and at least some of the monitors may be positioned at one or more remote locations. At least some the cameras may have a capability to transmit images, and also heart tones and sounds.

In further embodiments, the oral airway device 460 may comprise an esophageal stethoscope (not shown) which may be either built-in the wall 462 or the esophageal stethoscope may be insertable into the channel 472, the ETT lumen and/or the channel 472. In further embodiments, the oral airway device 460 may comprise a temperature probe (not shown) which may be either combined with the esophageal stethoscope (not shown) or the temperature probe may be built-in the wall 462 or the temperature probe may be insertable into the channel 472, the ETT lumen and/or the channel 472.

In some embodiments, the camera channel 472 is a hollow passage in the wall 462 and the camera channel 472 is completely separated from the ETT lumen 468.

In other embodiments, the camera channel 472 is a semi-lumen which is connected to the ETT lumen 468 with gap or slit. In further embodiments, there is a slit that runs along the length of the camera channel 472 on one of the surfaces of the wall 462. A camera can be easily inserted and removed from the camera channel 472 by being pulled through the slit.

In the embodiment of FIG. 1A, the oral airway device 460 comprises a second channel 474. In other embodiments, the channel 474 may be missing. In some other embodiments, more than one channel 474 is present.

The channel 474 is a hollow passage in the wall 462. The channel 474 can be used for aspirating fluids by inserting a suction tube in the channel 474. In this disclosure, the channel 474 may be referred as the esophageal channel 474. The esophageal channel 474 may be used for aspirating stomach contents and in order to prevent vomiting.

The esophageal channel can be also used for inserting other tools, including, but not limited to, a bougie, stylet, forceps, esophageal stethoscope and/or camera.

The esophageal channel 474 runs along the distal-proximal 462A-462B axis of the wall 462. The esophageal channel 474 is located peripherally to the ETT lumen 468 in the embodiment of FIG. 1A. As can be seen in the FIG. 1A, the channels 472 and 474 flank the ETT lumen 468 which is positioned between the channels 472 and 474.

In other embodiments, the camera channel 472 may be positioned centrally on the dorsal surface 462C and as discussed in more detail below. In other embodiments, the esophageal channel 474 may be positioned centrally on the dorsal surface 462C and as discussed in more detail below.

In yet other embodiments, the ETT lumen 468 may be positioned peripherally, as discussed in more detail below.

However, in all embodiments of the oral airway device 460, the relative positioning of the ETT lumen 468, the camera channel 472 and the esophageal channel 474 is such that it permits a practitioner to visualize by using camera tools/devices protruding from the ETT lumen and/or the esophageal channel 474.

The esophageal channel 474 opens with a proximal opening 474B near the proximal end 462 of the wall 462. The proximal opening 474B is an inlet through which a tool can be inserted into the esophageal channel 474.

The esophageal channel 474 ends with a distal opening 474A which is an outlet in near proximity to the distal end 462A of the wall 462. A tool or camera which is inserted into the channel 474 may protrude distally from the channel 474 from the distal end 474A.

In some embodiments, the esophageal channel 474 can be extended through the tongue 470 and up to the tongue tip 470A. In this embodiments, the distal opening 474 is located distally to the distal end 462A of the wall 462.

A tool, such as for example a suction tube, (not shown) can be inserted through the proximal opening 474B in the esophageal channel 474. The suction tube (or any other tool being inserted in the channel 474) can protrude from the distal opening 474A of the channel 474. The esophageal channel 474 can be used for hosting a bougie, a stylet, a camera, stethoscope, a temperature probe, a sound-monitoring and/or heart tone device which may be combined with a camera, forceps and/or any other tool that is used during intubation and or extubation of a patient.

Any of these tools are insertable and removable from the esophageal channel 474 and/or the camera channel 472 and can be used as needed for hosting these tools as well. A position of the tool at the distal opening 474A can be adjusted as needed in order to manipulate patient's tissues and/or provide suction if needed. In some embodiments, the esophageal channel 474 is a passage in the wall 462 and the esophageal channel 474 is completely separated from the ETT lumen 468.

In other embodiments, the esophageal channel 474 is a semi-lumen which is connected to the ETT lumen 468 with a slit 475 as showing in FIG. 1A. The slit 475 that runs along the length of the esophageal channel 474. The slit 475 opens into the ETT lumen 468 in the embodiment of FIG. 1A. In other embodiments, the slit 475 may open externally on the wall 462.

While the individual position of the two channels 472 and 474 may vary in the wall 462, a relative positioning of the channels 472 and 474 is such that when a camera is inserted in the camera channel 472 and protrudes from the distal opening 472A of the camera channel 472, the camera can visualize a distal end of a tool inserted into the esophageal channel 474 and protruding from the distal opening 474A of the esophageal channel 474. Accordingly, manipulations of the tool can be visualized with the camera, as needed.

Because the oral airway device 460 assembles several tools together, one practitioner can perform a placement of the oral airway device 460. There is no need to involve multiple operators for manipulating different tools.

In the drawing of FIG. 1A, the camera channel 472 is positioned in the wall 462 such that the distal opening 472A of the channel 472 opens on the ventral surface 462D or near the ventral surface 462D. The channel 474 is positioned such that its distal opening 474A opens on the dorsal surface 462C or near the dorsal surface 462C of the wall 462. In other embodiments, the camera channel 472 is positioned in the wall 462 such that the distal opening 472A of the channel 472 opens on the dorsal surface 462C or near the dorsal surface 462C. The esophageal channel 474 can be positioned such that its distal opening 474A opens on the dorsal surface 462C or near the dorsal surface 462C of the wall 462.

As can be appreciated by a person of skill, in some embodiments, the channels 472 and 474 may be interchangeable, i.e. a camera can be inserted into either of the two channels, as needed. In further embodiments, the device 460 may have more than two channels in the wall 462. These additional channels may be located peripherally to the ETT lumen 468. In some procedures, a camera can be also placed into the ETT lumen 468, if needed.

In the embodiment of FIG. 1A, the wall 462 has uneven thickness. The thickness of the wall 462 may be greater on the dorsal surface of the wall 462 and/or in flanks 462L and/or 462R between the dorsal surface 462C and the ventral surface 462D in order to accommodate the channels 472 and 474 which are typically hollow passages in the wall 462. In other embodiments, the thickness of the wall 462 may be the same or nearly the same around the perimeter of the oral airway device 460.

Figure 1B:
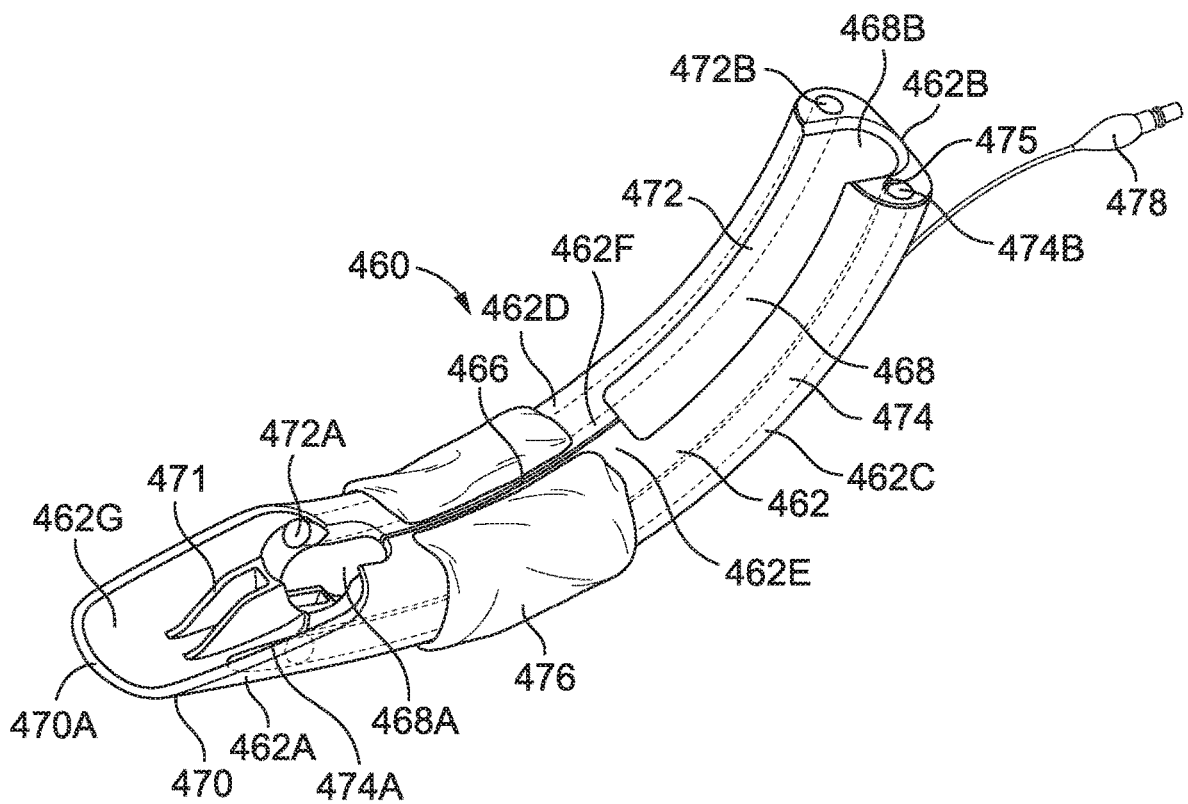
FIG. 1B depicts an oral airway device with a cuff and comprising a peripheral camera channel.

FIG. 1B provides a further embodiment of the oral airway device 460. All elements are as described in connection with FIG. 1A, except the oral airway device 460 in the embodiment of FIG. 1B comprises a cuff 476. The cuff 476 is attached around the perimeter of the wall 462 and it wraps around the wall 462 proximally to the distal opening 468A of the ETT lumen 468. The cuff 476 can be inflated with means 478. If needed, the cuff 476 is inflated after the device 460 is inserted into a patient in order to establish a closed system and to ventilate a patient. The cuff 476 is attached to the wall 462 and it does not go over the slit 466 such that when the cuff 476 is not inflated, the edges of the wall 462 can be still pulled apart at the slit 466 in the area where the cuff 476 is attached to the wall 462. While in the embodiment of FIG. 1B, the cuff 476 is inflatable, in other embodiments, the cuff 476 may be a soft donut-like cushion which is not inflatable.

Figure 1C:
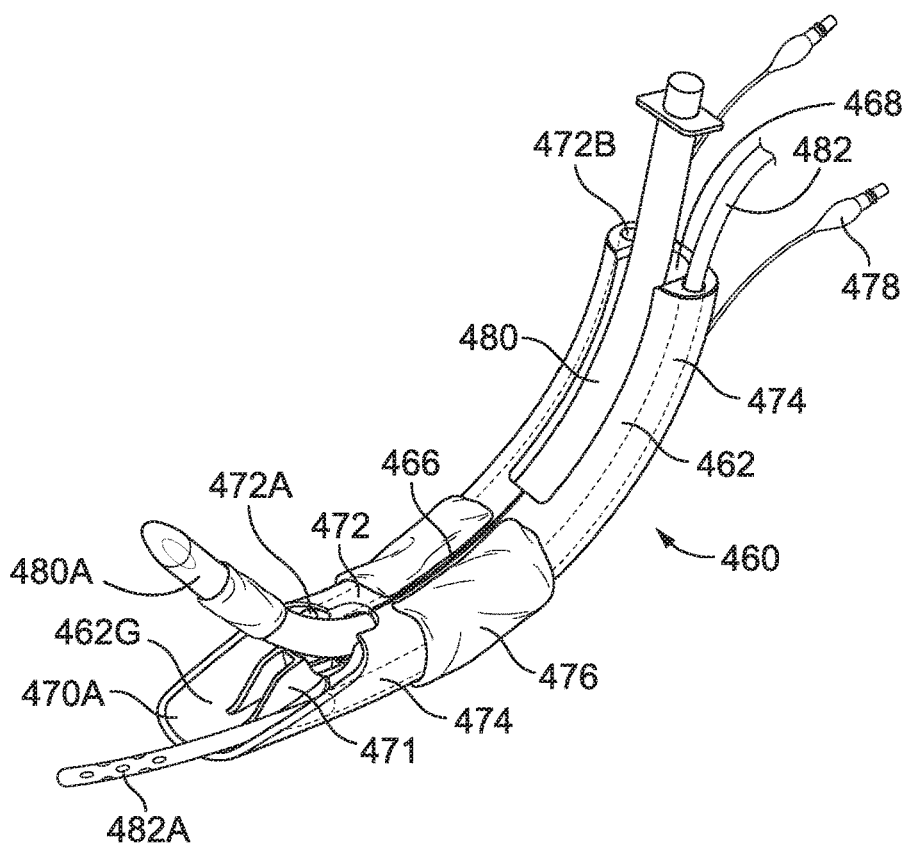
FIG. 1C depicts an endotracheal tube and a suction tube loaded onto the oral airway device of FIG. 1B.

FIG. 1C shows an endotracheal tube 480 and a suction tube 482, both of which are inserted into the oral airway device 460. All elements of the oral airway device 460 as were described in connection with FIGS. 1A and 1B. As can be seen in FIG. 1C, the endotracheal tube 480 is inserted into the ETT lumen 468. A distal end 480A of the endotracheal tube 480 protrudes from the distal opening 468A of the ETT lumen 468. The endotracheal tube 480 is elevated above the surface of the internal surface 462G by the ramp 471. This provides a technical advantage of preventing the distal end 480A of the endotracheal tube 480 from pushing and dragging against the surface of the device 460 and/or against tissues of a patient during insertion of the device 460 into the patient.

Accordingly, with the help of the ramp 471 and under continuous visualization from a camera inserted into the camera channel 472, an insertion of the endotracheal tube 480 (or any other device loaded in the ETT lumen 468) can be accomplished quicker as the position of the endotracheal tube 480 is guided and the endotracheal tube 480 is prevented from folding, bending and otherwise blocking completion of the insertion.

The oral airway device 460 provides a capability for combining several cameras, each of the cameras being positioned at a different location and accordingly providing a view of the patient's tissues from a different angle. This improves accuracy for endotracheal tube placement.

In the drawing of FIG. 1C, the suction tube 482 is inserted into the esophageal channel 474. The distal end 482A of the suction tube 482 protrudes from the distal opening 474A of the channel 474. Just like a camera which is insertable and removable from the camera channel 472, the suction tube 482 can be also easily inserted and removed from the esophageal channel 474.

Figure 1D:
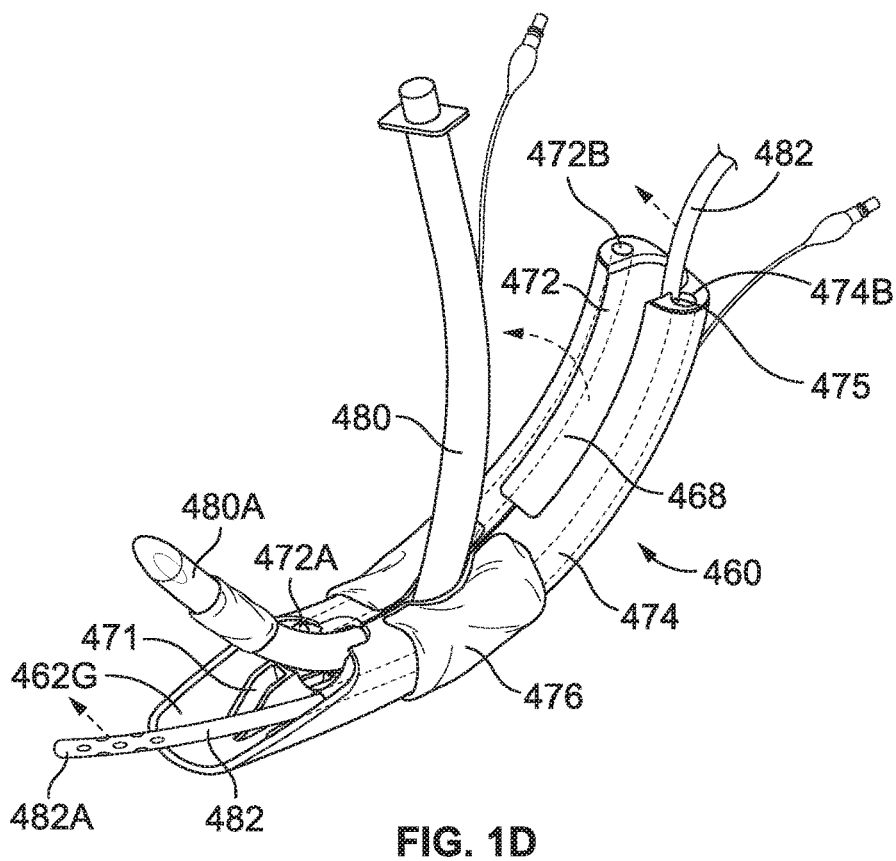
FIG. 1D depicts a removal of the endotracheal tube from the oral airway device of FIG. 1B.

Referring to the drawing of FIG. 1D, it shows how the endotracheal tube 480 can be separated from the oral airway device 460 by being pulled through the slit 466. This allows a practitioner to easily remove and/or replace an endotracheal tube as needed while the oral airway device 460 is still placed in a patient. In alternative, the oral airway device 460 can be easily removed from the patient while the endotracheal tube 480 remains inserted and in place in the patient. This provides a technical advantage of not needing to conduct multiple rounds of intubation and extubation.

As is also shown in the drawing of FIG. 1D, the suction tube 482 can be easily removed from the oral airway device 460 from the slit 475 of the esophageal channel 474. Thus, a practitioner can remove the suction tube 482 or any other tool, such as for example as a bougie, while the oral airway device 460 remains inserted into the patient.

Figures 1E, 1F, 1G:
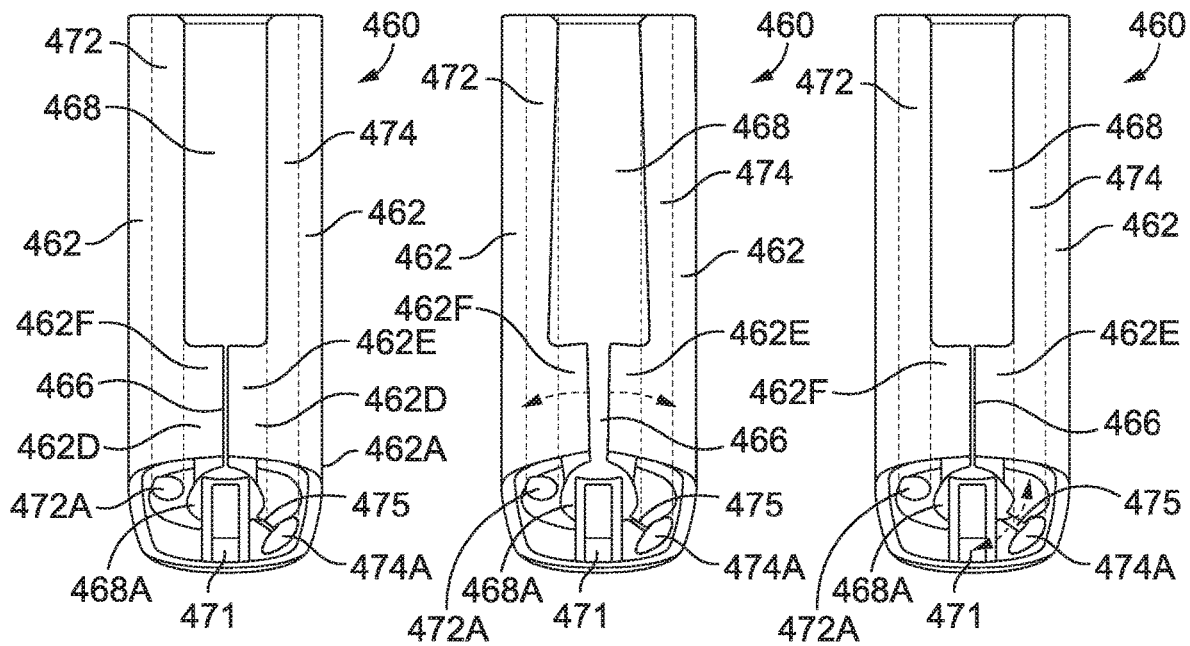
FIG. 1E depicts the distal end of the oral way device of FIG. 1A.
FIG. 1F depicts the distal end of the oral way device of FIG. 1A with the flaps being pushed apart.
FIG. 1G depicts the distal end of the oral way device of FIG. 1A and showing a gap widening in the slit of the esophageal channel.

Referring to FIGS. 1E, 1F and 1G, they are an enlarged view of details at the distal end of the oral airway device 460. The oral airway device 460 is shown in these drawings from the ventral surface 462D.

All elements are labeled in the same way as in connection with FIGS. 1A-1D. In FIG. 1E, one can see the distal opening 472A of the camera channel 472 positioned near the ventral surface 462D of the wall 462. In this embodiment, the camera channel 472 is a passage which is separated from the ETT lumen 468. The distal opening 474A of the esophageal channel 474 is positioned near the dorsal surface 462C of the wall 462. In FIG. 1E, the esophageal channel 474 has the slit 475 which runs along the length of the esophageal channel 474 and which opens the esophageal channel 474 into the ETT lumen 468. This helps in guiding a placement of the oral airway device 460 with a bougie or stylet placed in the esophageal channel 474.

As can be seen from the embodiment of FIG. 1E, the ETT lumen 468 is positioned between the channels 472 and 474. As shown in FIG. 1F, the flaps 462E and 462F can be pushed aside such that a device, such as for example an endotracheal tube, can be loaded into the ETT lumen 468 of the oral airway device 460.

As shown in FIG. 1G, the slit 475 can be also widen to a gap as the wall 462 and/or at least a portion of the channel 474 is made of a flexible material. The slit 475 facilitates a removal of a suction tube or any other tool from the esophageal channel 474.

Figure 1H:
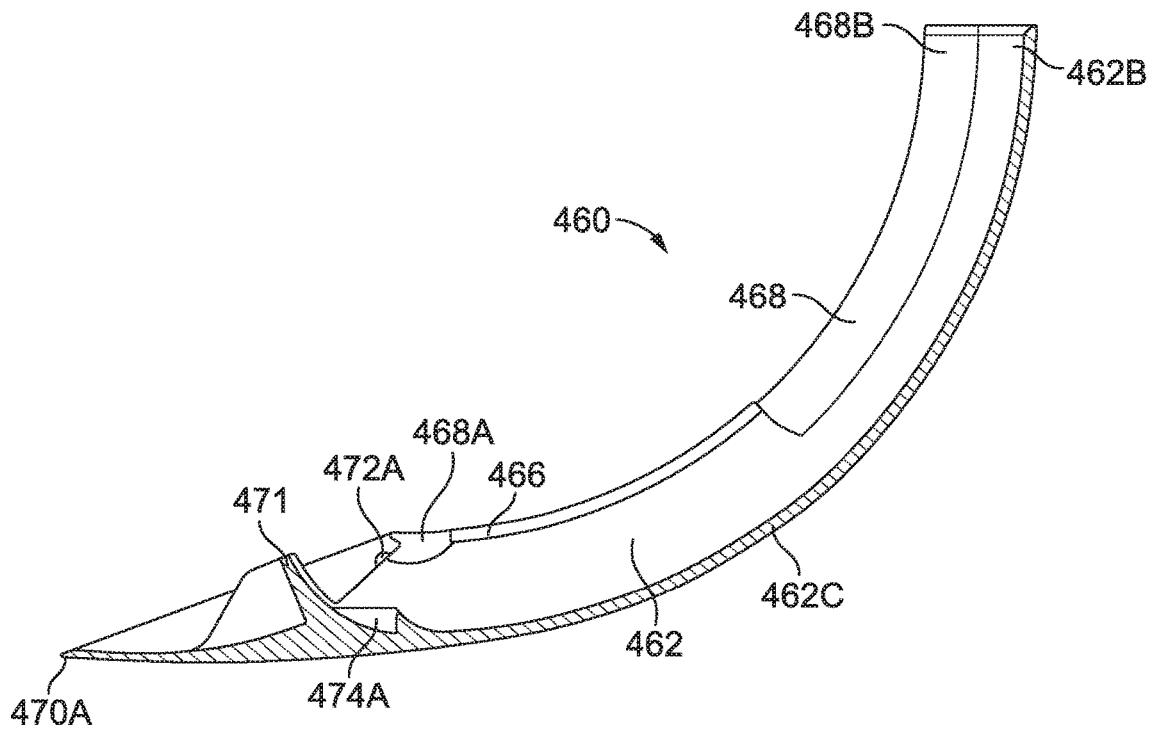
FIG. 1H is a longitudinal section through the oral airway device of FIG. 1A.

FIG. 1H is a longitudinal section through the oral airway device 460. All elements are labeled as in connection with FIGS. 1A-1G.

Figure 1I:
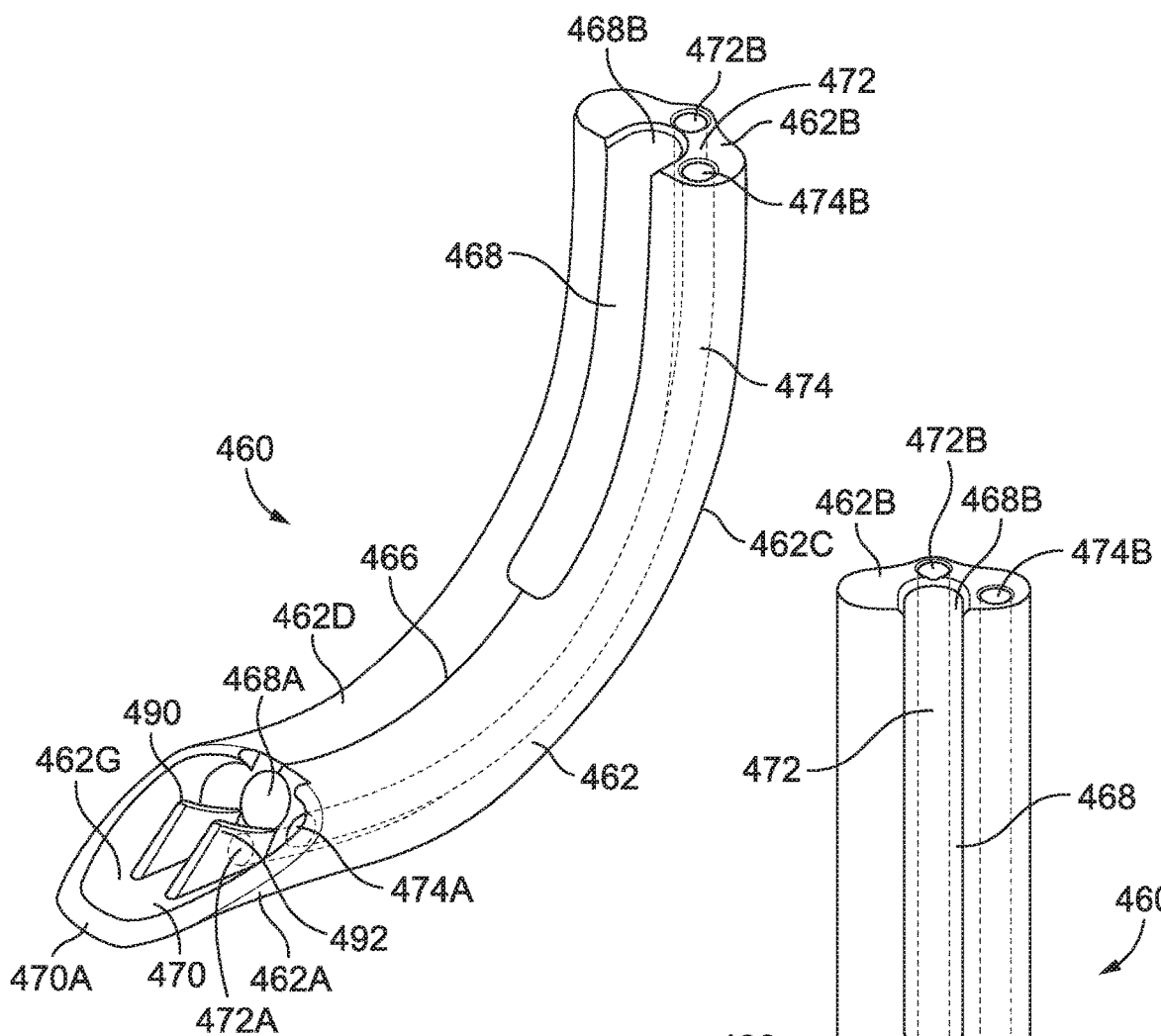
FIG. 1I depicts an oral airway device in which a camera channel is located centrally on the dorsal side of the oral airway device.

FIG. 1I depicts a further embodiment of the oral airway device 460. As was discussed in connection with FIG. 1A, the oral airway device 460 is a tubal body which is curved such that the oral airway device 460 follows the contour of the roof of a patient's mouth during insertion of the device 460 into the patient.

The curved tubal body of the oral airway device 460 is made by a wall 462 with a distal end 462A and a proximal end 462B. The wall 462 is curved along the distal-proximal 462A-462B axis such that the wall 462 follows the contour of the roof of a patient's mouth. The wall 462 creates an arch. The wall 462 has a dorsal surface 462C and a ventral surface 462D. Because of the arch curvature, a length of the wall 462 is longer on the dorsal surface, 462C, than on the ventral surface, 462D. The ventral surface 462D is in contact with the patient's tongue when the oral device 460 is placed in the patient.

The wall 462 has the slit 466 which runs along the distal-proximal 462A-462B axis on the ventral surface 462D. The wall 462 encircles the ETT lumen 468. The ETT lumen 468 is hollow and has a distal opening 468A at the distal end 462A of the wall 462. The ETT lumen 468 has a proximal opening 468B at the proximal end of the wall 462. The slit 466 opens into the ETT lumen 468.

Unlike the embodiment of the drawing of FIG. 1A, the wall 462 in the embodiment of FIG. 1I does not have flaps, but some proximal portion of the ETT lumen 468 is still not covered by the wall 462 on the ventral surface 462D. Accordingly, some portion of the ETT lumen 468 is exposed and this facilitates an insertion and removal of an endotracheal tube into the ETT lumen 468.

At the distal end 462A, the wall 462 ends with a tongue 470 on the dorsal surface 462C. The distal end 470A of the tongue 470 may be an oval or round shape. The tongue 470 is tapered at its distal end 470A. The tongue 470 is used to gently push patient's tissues apart during insertion of the device 460. The tongue 470 protrudes distally from the wall 462.

There is a ramp 490/492 which comprises two blocks, 490 and 492, each attached to the surface of the internal surface 462G of the tongue 470. The ramp 490/492 is sloped and positioned proximally to the tongue 470 and distally to the distal opening 468A of the ETT lumen 468 such that the blocks 490 and 492 flank the distal opening 468A of the ETT lumen 468.

The ramp 490/492 elevates above the surface of the internal side 462G of the wall 462. The function of the ramp 490/492 is to lift and support a distal end of a device loaded in the ETT lumen 468, such as for example an endotracheal tube, above the internal surface 462G.

The wall 462 has at least two hollow channels, 472 and 474. The esophageal channel 474 is a hollow passage with the distal opening 474A and the proximal opening 474B and is positioned in the wall 462, as was described in connection with FIG. 1A.

However, the camera channel 472 is positioned near the central line on the dorsal side 462C of the wall 462 in the embodiment of FIG. 1I. The camera channel 472 is hollow and has a proximal opening 472B at the proximal end 462B of the wall 462. The camera channel 472 runs along the distal-proximal 462A-462B axis of the wall 462. The camera channel 472 ends with a distal opening 472A at the distal end 462A of the wall 462. The distal opening 472A is preferably is not sealed such that a camera can protrude distally from the camera channel 472. In some embodiments, the distal opening 472A is sealed with a transparent material (not shown) such that a camera can capture images through the sealed window while being positioned inside the camera channel 472.

Figure 1J:
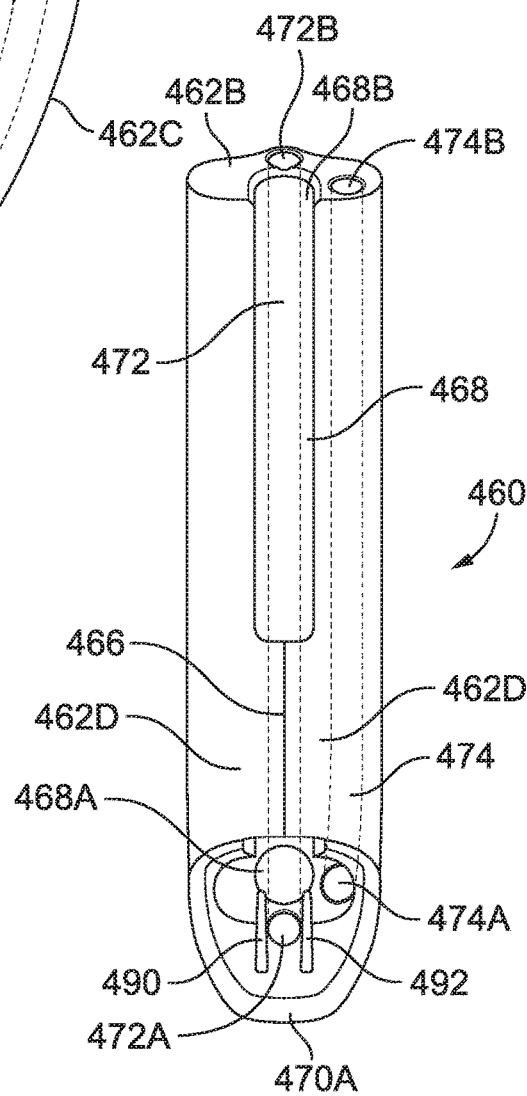
FIG. 1J depicts the oral airway device of FIG. 1I from the ventral surface.

Referring to FIG. 1J, this is a ventral surface view of the oral airway device of FIG. 1I. As can be further seen from the drawing of FIG. 1J, the distal opening 472A of the camera channel 472 is flanked by blocks 490 and 492. Accordingly, when a camera protrudes from the camera channel opening 472A, the blocks 490 and 492 flank the camera and keep it in place. Furthermore, and as can be seen in FIG. 1J, the ETT lumen 468 opens with the distal opening 468A right above the camera lumen opening 472A. Accordingly, when an endotracheal tube is loaded into the ETT lumen 468 and a camera is inserted into the camera channel 472, a distal end of the endotracheal tube protruding from the distal opening 468A of the ETT lumen can be constantly monitored by the camera from the distal opening 472A. This facilitates intubation, including intubation of patients who are difficult to intubate and/or patients with collapsed airways.

Figure 1K:
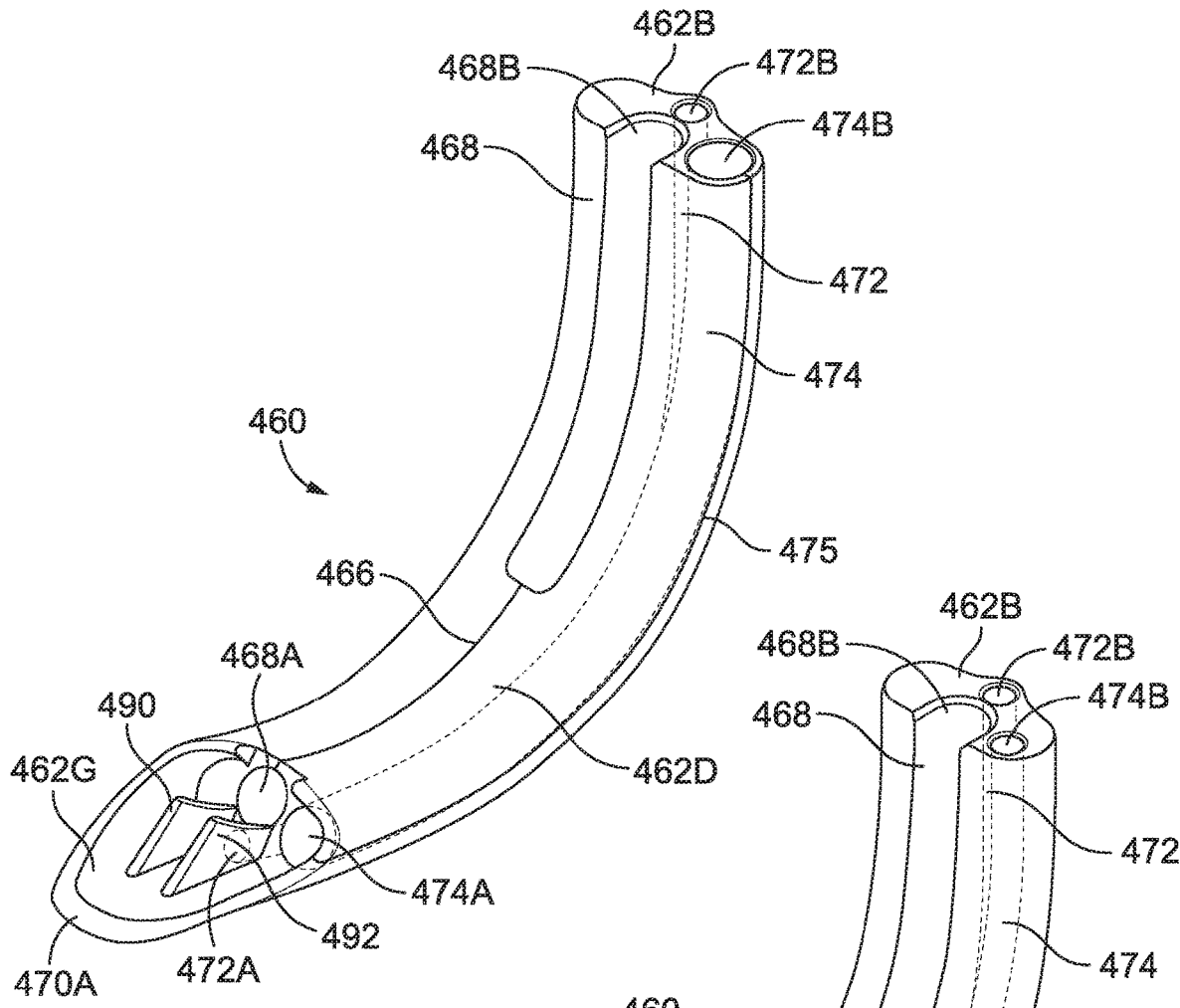
FIG. 1K depicts an oral airway device in which a camera channel is located centrally on the dorsal side of the oral airway device and an esophageal channel comprises a slit.

Referring to FIG. 1K, it depicts a further embodiment of the oral airway device 460 in which the camera channel 472 is positioned near the central line of the dorsal surface 462C of the wall 462, as was discussed in connection with FIG. 1I. In the embodiment of FIG. 1K, the ETT lumen is positioned centrally as determined by the proximity to the central axis of the oral airway device 460.

The esophageal channel 474 is positioned peripherally in one of the flanks 462L or 462R of the wall 462. The esophageal channel 474 comprises the slit 475 which runs externally along the distal-proximal axis 462A-462B in the wall 462. The edges of the wall 462 can be pushed apart along the slit 475 in order to facilitate insertion and removal of a suction tube or any other tool into the esophageal channel 474.

The diameter of the esophageal channel 474 is such that it can accommodate a scope for an upper endoscopy (EGD). Thus, the oral airway device 460 can be used to deliver a scope into the upper digestive tract, while at the same time being used for managing the patient's airways. Accordingly, the oral airway device 460 with the scope compatible esophageal channel can be used for various procedures on esophagus, stomach and/or the duodenum.

Figure 1L:
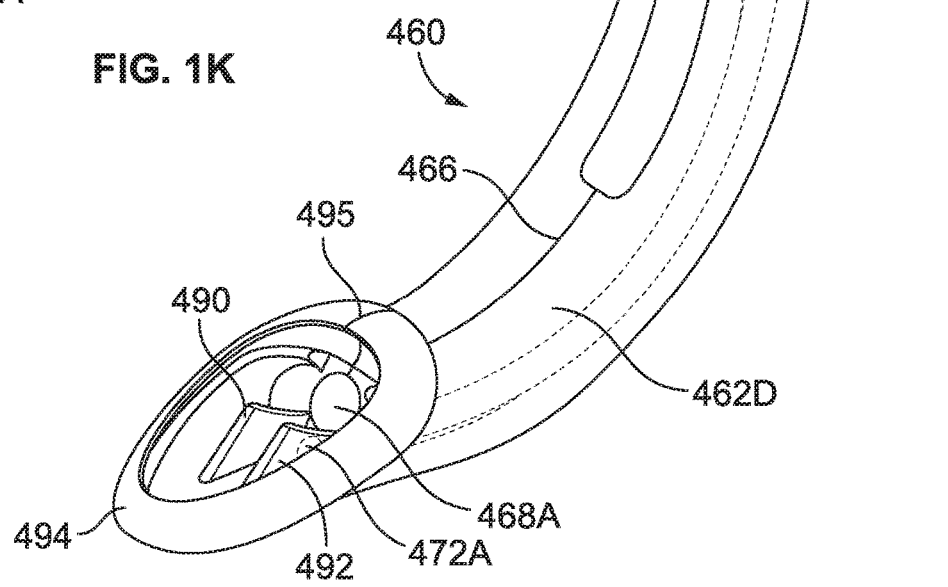
FIG. 1L depicts the oral airway device of FIG. 1I which comprises a non-inflatable cuff.

Referring to FIG. 1L, it provides a further embodiment of the oral airway device 460 in which the oral airway device 460 ends with a distal, soft and non-inflatable cuff 494.

The oral airway device 460 in this embodiment of FIG. 1L comprises the camera channel 472 located near the central line of the dorsal surface 462C of the wall 462, as was discussed in connection with FIGS. 1I and 1J. It will be appreciated, that any of the embodiments for the oral airway device 460 may end with the distal soft non-inflatable cuff 494.

In the embodiment of FIG. 1L, the soft non-inflatable distal cuff 494 is attached around the perimeter of the distal end 462 and the tongue tip 470A. Notably, the oral airway device 460 comprises the slit 466 in the wall 462 on its ventral surface 462D. The slit 466 opens into the ETT lumen 468. The cuff 494 has a slit 495 which is aligned with the slit 466. Thus, the wall 462 and the cuff 494 can be pushed apart at the slits 466 and 495 in order to insert an endotracheal tube or some other breathing tube into the ETT lumen 468.

The soft non-inflatable distal cuff 492 softens an impact of the oral airway device 460 on the patient's tissues during insertion. The soft non-inflatable cuff 492 also helps with occluding the patient's pharynx and establishing a closed system for ventilation.

Figure 1M:
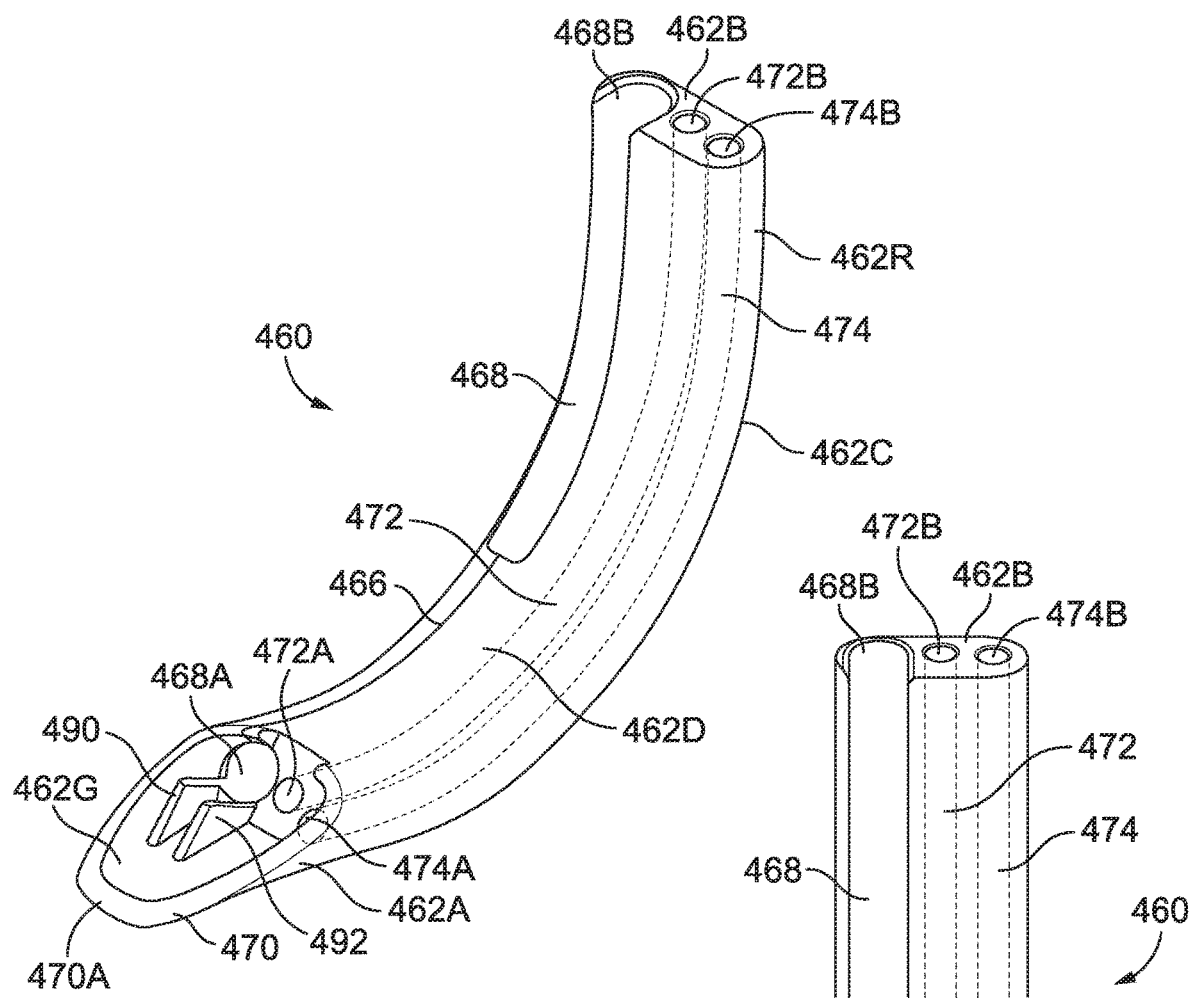
FIG. 1M depicts an oral airway device which comprises a central camera channel and peripheral ETT lumen.

Referring to FIG. 1M, it provides a further embodiment of the oral airway device 460. As was discussed in connection with FIGS. 1A-1L, the oral airway device 460 is a tubal body which is curved such that the oral airway device 460 follows the contour of the roof of a patient's mouth during insertion of the device 460 into the patient.

The curved tubal body of the oral airway device 460 is made by the wall 462 with the distal end 462A and the proximal end 462B. The wall 462 is curved along the distal-proximal 462A-462B axis such that the wall 462 follows the contour of the roof of a patient's mouth. The wall 462 creates an arch. The wall 462 has a dorsal surface 462C and a ventral surface 462D. Because of the arch curvature, a length of the wall 462 is longer on the dorsal surface, 462C, than on the ventral surface, 462D.

The ventral surface 462D is in contact with the patient's tongue when the device 460 is placed in the patient. In FIG. 1M, the ventral surface 462D and the right flank 462R are shown.

In the embodiment of FIG. 1M, the camera channel 472 is positioned centrally or near the central axis of the oral airway device 460. The camera channel 472 has the distal opening 472A and the proximal opening 472B. A camera can be inserted and slid along the camera channel 472. The camera can protrude distally from the distal opening 472A of the camera channel 472.

The wall 462 encircles the ETT lumen 468 which is positioned peripherally from the central location of the camera channel 472. Some proximal portion of the ETT lumen 468 is not covered by the wall 462 on the ventral surface 462D. Accordingly, some proximal portion of the ETT lumen 468 is exposed which facilitates insertion and removal of an endotracheal tube into the ETT lumen 468.

Just like in connection with other embodiments of the oral airway device 460, the wall 462 comprises the slit 466 which runs along the distal-proximal axis 462A-462B. The slit 466 is positioned over the ETT lumen 468 and opens into the ETT lumen 468. The edges of the wall 462 can be pushed apart along the slit 466. This facilitates a loading into and removal of an endotracheal tube from the ETT lumen 468. In the embodiment of FIG. 1M, the slit 466 is positioned on the ventral surface 462D of the wall 462. In other embodiments, the slit 466 may be positioned on a flanking surface—between the ventral surface 462D and the dorsal surface 462C or on the dorsal surface 462C.

The ETT lumen 468 is hollow and has the distal opening 468A at the distal end 462A of the wall 462. The ETT lumen 468 has the proximal opening 468B at the proximal end of the wall 462.

At the distal end 462A, the wall 462 ends with the tongue 470 on the dorsal surface 462C. The distal end 470A of the tongue 470 may be an oval or round shape. The tongue 470 is tapered at its distal end 470A. The tongue 470 is used to gently push patient's tissues apart during insertion of the oral airway device 460. The tongue 470 protrudes distally from the wall 462.

The esophageal channel 474 is positioned peripherally to the camera channel 472 and can be used with various tools, as discussed in connection with other embodiments.

There is a ramp which comprises two blocks, 490 and 492, each attached to the surface of the internal surface 462G. The ramp 490/492 is positioned proximally to the tongue 470 and distally to the distal opening 468A of the ETT lumen 468 such that the blocks 490 and 492 flank the distal opening 468A and guide an endotracheal tube when it is protruding from the distal opening 468A of the ETT lumen 468.

Figure 1N:
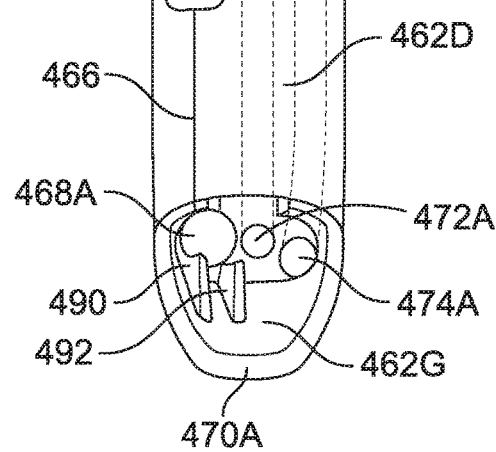
FIG. 1N depicts the oral airway device of FIG. 1M from the ventral surface.

As can be further seen from the drawing of FIG. 1N which depicts the device 460 of the drawing 1M from the ventral surface, the distal opening 468A of the ETT lumen 468 is flanked by blocks 490 and 492 which are tilted somewhat toward the center of the internal surface 462G. Accordingly, the blocks 490 and 492 guide a distal end of an endotracheal tube toward the center of the tongue 470. This brings a distal portion of the endotracheal tube under continuous visualization from a camera through the distal opening 472A of the camera channel 472.

In the embodiments of FIGS. 1M and 1N, the esophageal channel 474 is located peripherally to the camera channel 472. As can be seen from the drawing 1N, the distal end 474A of the esophageal channel 474 opens in near proximity to the distal opening 472A of the camera channel 472. Accordingly, if a tool is inserted into the esophageal channel 474, such as for example a stylet or bougie, the tool can be operated under continuous visualization from a camera inserted into the camera channel 472 and vice versa, a camera can be positioned in the esophageal channel 474 and a tool can be placed in the camera channel. If needed, two cameras can be used, on in the esophageal channel 474 and the other one in the camera channel 472.

Figure 1O:
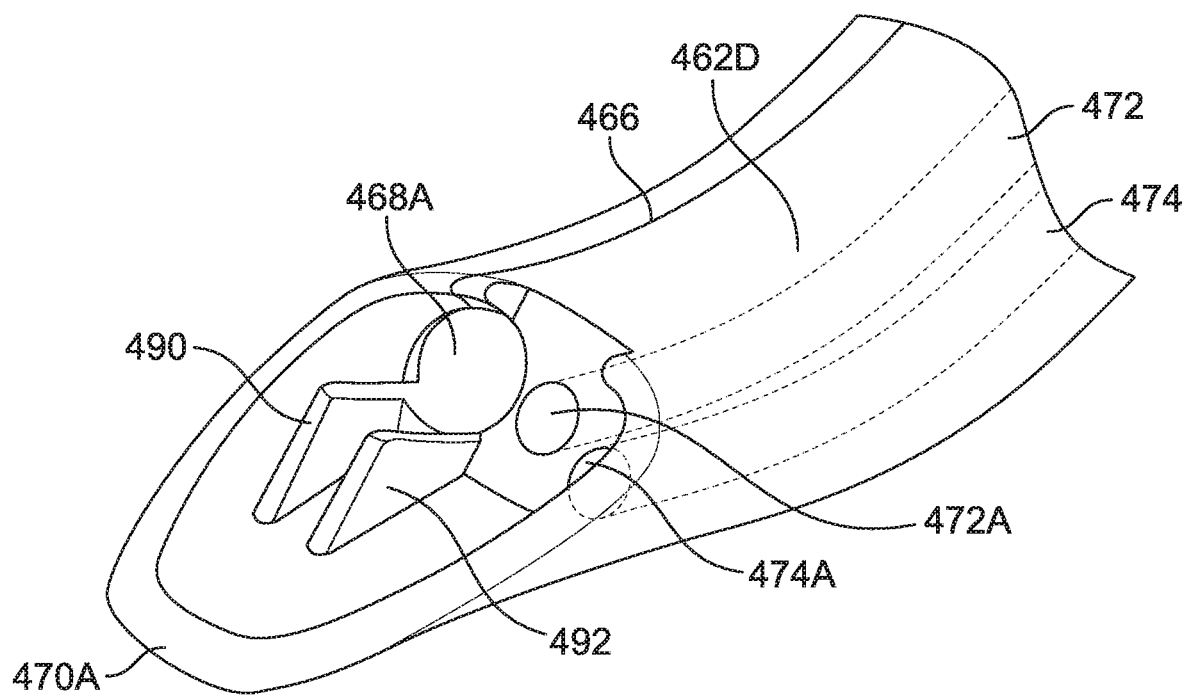
FIG. 1O depicts a distal portion of the oral airway device of FIG. 1M.

Referring to FIG. 1O, it is a zoomed view of a distal portion of the oral airway device 460 of the FIG. 1M. The distal opening 468A of the ETT lumen 468 is shown. The slit 466 provides access to the ETT lumen 468. The blocks 490 and 492 flank the distal opening 468A and elevate/guide an endotracheal tube (not shown) when loaded in the ETT lumen 468.

Figure 1P:
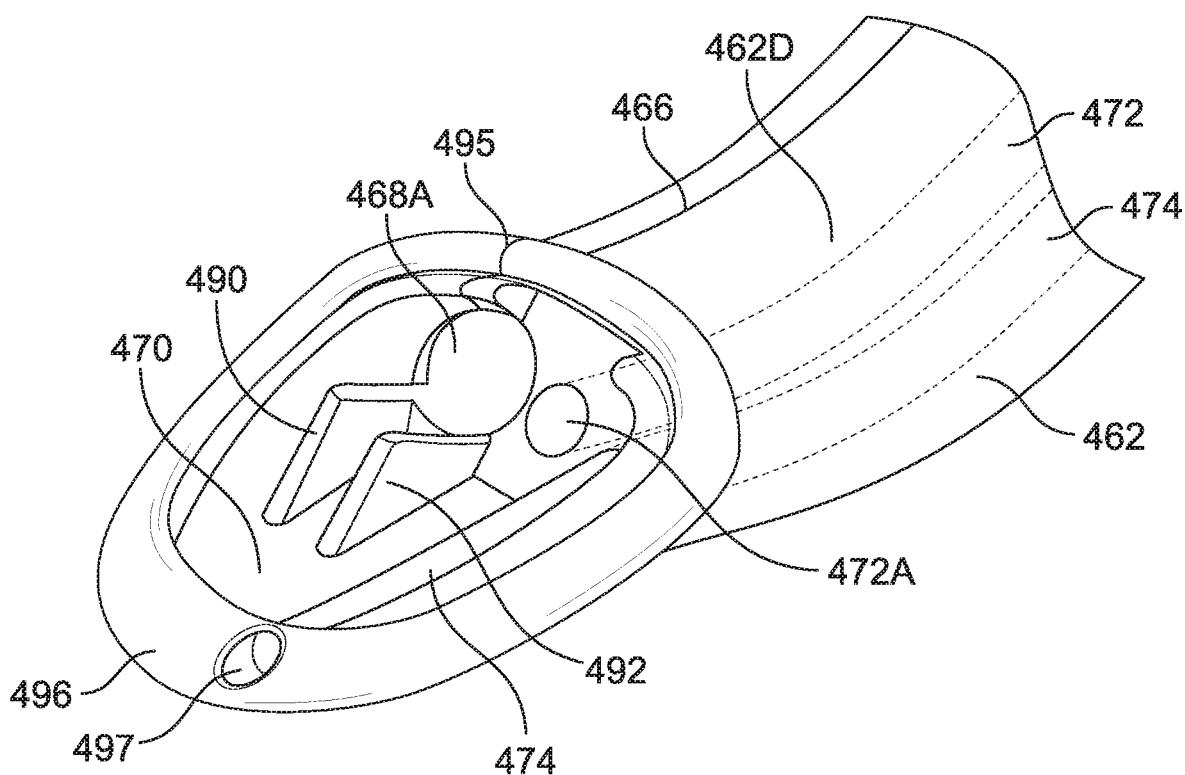
FIG. 1P depicts a distal portion of the oral airway device of FIG. 1M which further comprises a distal cuff and an extended esophageal channel.

Referring to FIG. 1P, it is a zoomed view of a distal portion of the oral airway device 460 as was discussed in connection with FIGS. 1M-1O, except the embodiment of FIG. 1P comprises a soft non-inflatable cuff 496 which is attached around the perimeter of the distal end 462A and the tongue 470 of the curved body of the oral airway device 460. The cuff 496 comprises a slit 495 which is aligned with the slit 466 in the wall 462. This allows pushing the cuff 496 and the wall 462 apart for loading an endotracheal tube into and its removal from the ETT lumen 468. In the embodiment of the FIG. 1P, the esophageal channel 474 is extended through the tongue 470 and through the cuff 496 which comprises an opening 497 which holds in place a suction tube or any other tool inserted into the esophageal channel 474. Thus, a suction tube or any other tool can protrude distally from the cuff 496 and prevent accumulation of fluids on the tongue 470 and behind the cuff 496, which otherwise may require a removal and replacement or cleaning of the oral airway device 460.

It will be appreciated that while in the embodiment of FIG. 1P, the distal cuff 496 is not inflatable, it may be inflatable in other embodiments. In further embodiments, the cuff 496 does not have the slit 495.

FIG. 1Q depicts an adaptor, generally 500, which can be loaded into the ETT lumen 468 of the oral airway device 460 or some other oral airway device. The adaptor 500 comprises two hollow tubes, an outer tube 502, and inner tube 504, the inner tube 504 being insertable and removable from the outer tube 502. The tubes 502 and 504 are either made curved to fit the shape of the lumen 468 of the oral airway device 460 or the tubes 502 and 504 are made of a flexible material such that they can assume the curved shape once inserted or prior to being inserted into the ETT lumen 468 of the oral airway device 460.

The inner tube 504 is longer in length than the outer tube 502. As shown in FIG. 1Q, a distal end 504A of the inner tube 504 protrudes distally from the distal end 502A of the outer tube 502. A proximal end 504B of the inner tube 504 protrudes proximally from the proximal end 502B of the outer tube 502.

The inner tube 504 is insertable into and removable from the outer tube 502. Accordingly, the length of the adaptor 500 can be adjusted as needed by having a longer or shorter portion of the inner tube 504 protruding proximally from the outer tube 502. The outer tube 502 and the inner tube 504 are hollow. The inner tube 504 has a central lumen 506 that has a proximal opening 506B and a distal opening 506A. If the inner tube 504 is removed from the outer tube 502, a central lumen of the outer tube 502 can be also used for inserting other devices.

The outer tube 502 may comprise a latch 508 located near the distal end 502A.

FIG. 1R depicts loading of the adaptor 500 into the ETT lumen 468 of the oral airway device 460. All elements are labeled as in connection with drawings 1A-1Q.

Referring to FIG. 1S, it depicts the adaptor 500 inserted in the ETT lumen 468 of the oral airway device 460. The latch 508 of the adaptor 500 is positioned over the proximal ends of the flaps 462F and 462E and the proximal end of the slit 466. Accordingly, the latch 508 holds the flaps 462D and 462E together and prevents the slit 466 from widening into a gap. This is helpful when the cuff 476 is to be inflated in a patient as the adaptor 500 prevents the slit 466 from widening into a gap. Accordingly, a closed system can be established with the cuff 476 and ventilation can be established.

Referring to FIG. 1T, it depicts a ventilation adaptor, generally 507. The ventilation adaptor 507 is a lid which can be used in order to establish a closed system in the oral airway device 460 with a slit and in order to connect the oral airway device 460 to a ventilator.

The ventilation adaptor 507 comprises a flat panel 508 with a distal edge 508A and a proximal edge 508B opposing the distal edge 508A. The flat panel 508 has a first longitudinal edge 508L and a second longitudinal edge 508R which opposes the first longitudinal edge 508L. The flat panel 508 is curved inwards along the longitudinal edges 508L and 508R such that there is a groove 508G along the longitudinal edge 508L and also there is a matching groove 508G along the longitudinal edge 508R. At or near the distal edge 508B, the flat panel 508 is attached to a flat panel 509. The flat panel 509 is positioned generally perpendicularly to the flat panel 508. The flat panel 509 comprises a conduit 509A which can be used for connecting the ventilation adaptor 507 to a ventilator.

As can be seen from the drawings of FIGS. 1U and 1V, the ventilation adaptor 507 fits tightly over the oral airway device 460 with the conduit 509A fitting over the proximal opening 468B of the ETT lumen 468. The flanks of the oral airway device 460 fit within the grooves 508Gs. Thus, the ventilation adaptor 507 keeps the slit 466 from coming apart. The ventilation adaptor 507 seals the oral airway device 460 and establishes a closed system in the oral airway device 460. A patient can then be ventilated through the conduit 509A which is connected to the ETT lumen 468.

In some embodiments, the ventilator adaptor 507 may comprise a second conduit 509B which is aligned with the proximal opening 474B of the esophageal channel 474.

Figure 2:
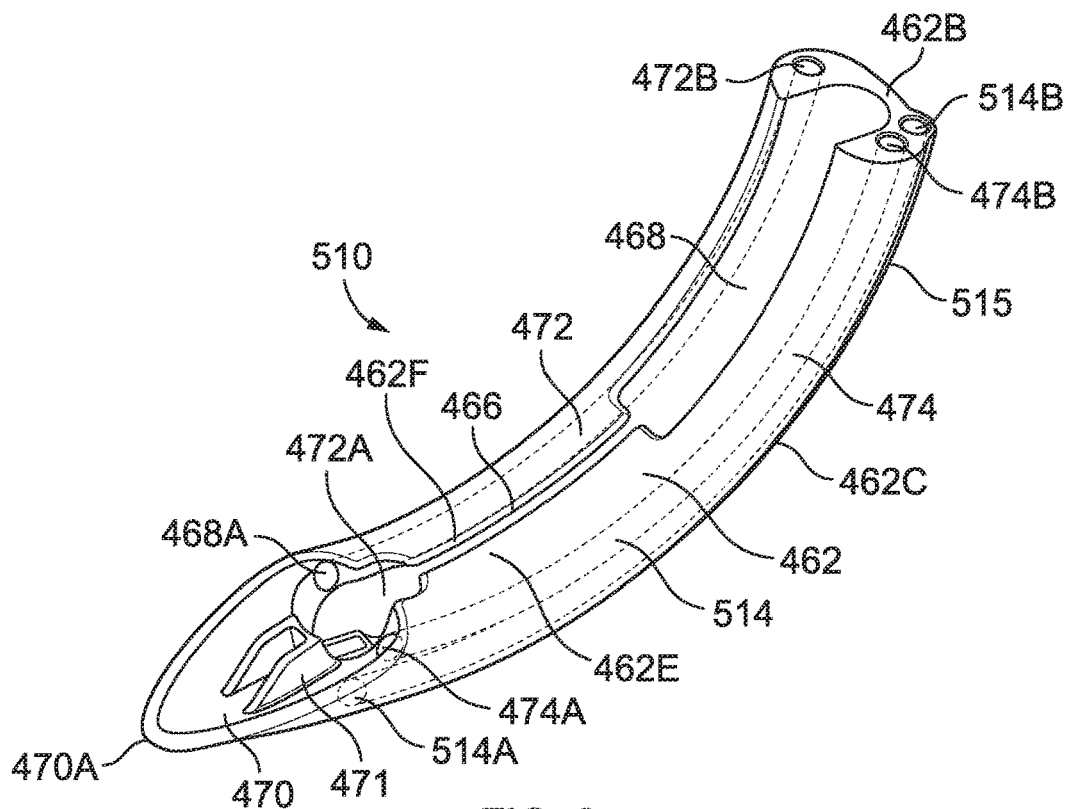
FIG. 2 depicts an oral airway device with three peripheral channels.

Referring to FIG. 2, it provides a further embodiment of an oral airway device, generally 510.

Just like the oral airway device 460, the oral airway device 510 has a tubal body created by the wall 462 which is curved as was discussed in connection with the device 460. All elements that are similar between devices 460 and 510 are labeled with the same numbers. Just like the oral airway device 460, the oral airway device 510 comprises channels 472 and 474. The camera channel 472 is located in the wall 460 peripherally to the ETT lumen 468 which is located centrally in the oral airway device 510. The camera channel 472 has the proximal opening 472B and the distal opening 472A. As discussed in connection with the device 460, a camera can be inserted and removed from the camera channel 472, as needed.

The channel 474 in the oral airway device 510 comprises the proximal opening 474B and the distal opening 474A. A tool, such as for example, a stylet or bougie can be inserted into the channel 474. The tool can be used under continuous visualization from the camera that is protruding distally from the distal opening 472A of the camera channel 472.

The camera channel 472 and the channel 474 are positioned peripherally to the ETT lumen 468.

As shown in FIG. 2, in the oral airway device 510, there is an additional peripheral channel 514 in the wall 462. The channel 514 is positioned on the dorsal surface 462C of the wall 462, but off center of the dorsal surface 462C. The channel 514 has a slit 515 which runs along the length of the channel 514. The slit 515 opens the channel 514 on the dorsal surface 462C of the wall 462. The channel 514 can be used for inserting a suction tube that can be used for aspirating stomach fluids. Other tools may be also loaded into the channel 514 as needed. The channel 514 opens up with a proximal opening 514B on the proximal end 462B of the wall 462. A suction tube or any other tool as needed may be inserted into the channel 514 through the proximal opening 514B. The length of the channel 514 may vary. The dorsal surface 460C of the wall 462 in the device 510 is arched as was described in connection with the device 460. In some embodiments, the channel 514 ends at the highest point of the arch. In other embodiment, the channel 514 may end at any other location on the dorsal surface 462C of the wall 462. As shown in FIG. 2, the channel 514 may extend dorsally into the tongue 470.

Figure 3A:
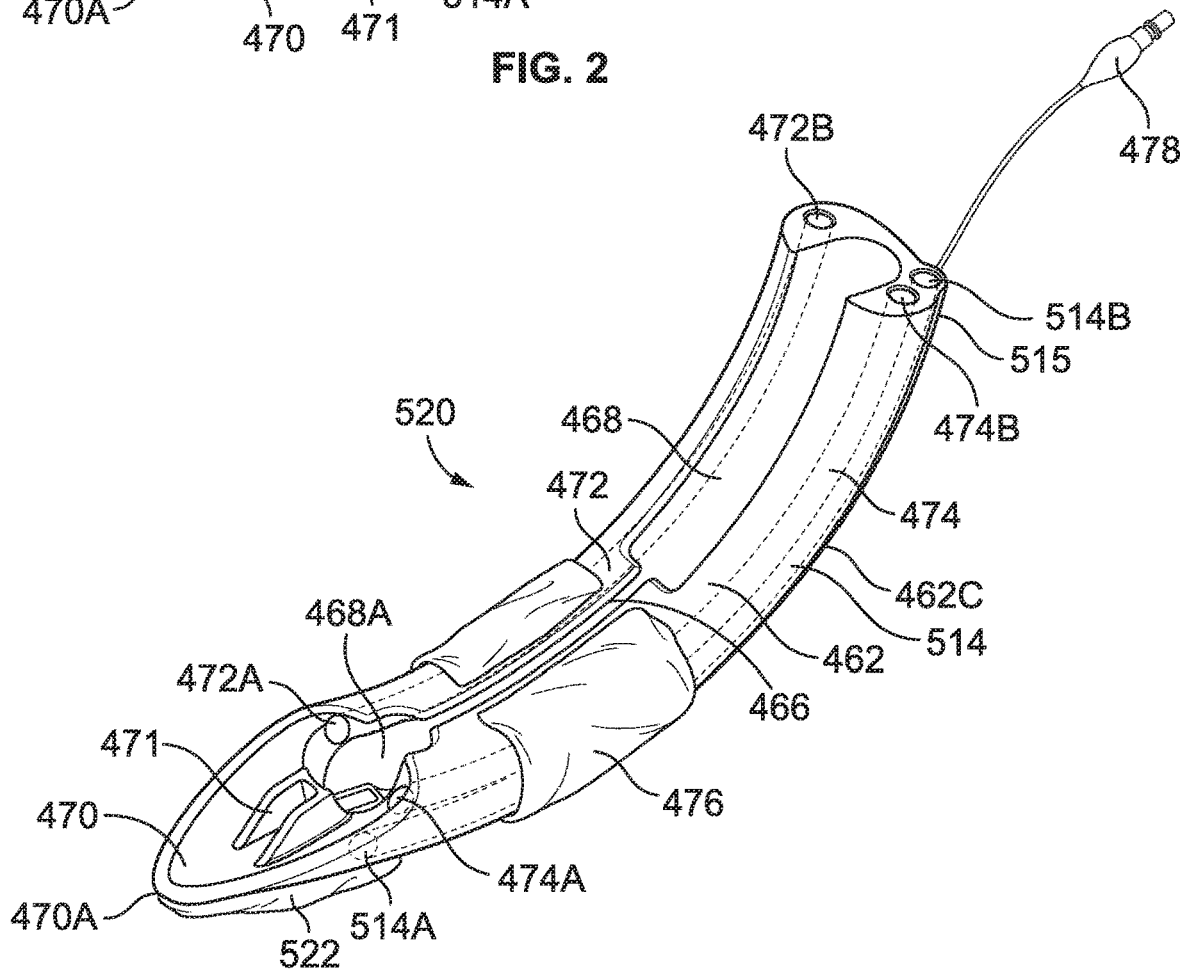
FIG. 3A depicts an oral airway device with three peripheral channels and an inflatable cuff.

Referring to FIG. 3A, it provides another embodiment of an oral airway device, generally 520. The oral airway device 520 comprises the same elements as was discussed in connection with the oral airway device 510 of FIG. 2, except the oral airway device 520 also comprises an inflatable cuff 476. The inflatable cuff 476 is the same inflatable cuff 476 as was described in connection with the device 460 in FIG. 1B. The inflatable cuff 476 can be inflated with a means 478. The oral airway device 520 also comprises a soft non-inflatable cuff 522 that covers the tongue 470 on the dorsal surface 462C of the oral airway device 520. One function of the non-inflatable cuff 522 is to cushion a contact between the tongue 470 and patient's tissues during an insertion of the oral airway device 520.

Figure 3B:
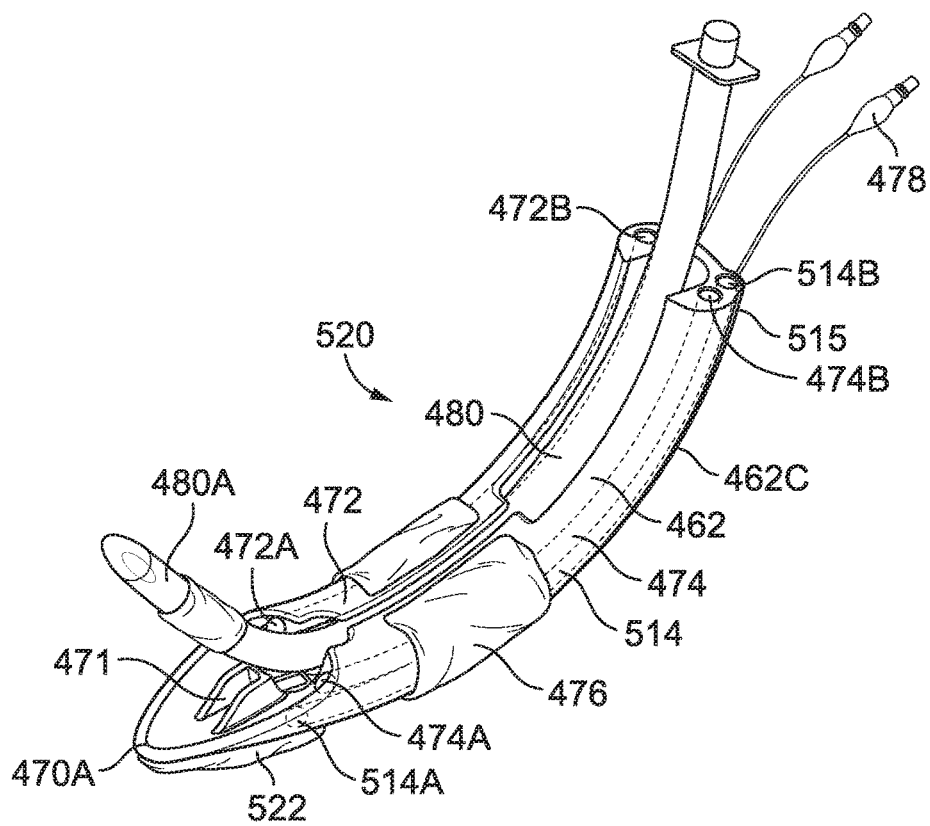
FIG. 3B depicts an endotracheal tube loaded into the oral airway device of FIG. 3A.

Referring to FIG. 3B, it depicts the endotracheal tube 480 loaded in the ETT lumen 468 of the device 520. In FIG. 3B, all elements of the oral airway device 520 as were described in connection with FIG. 3A.

Figure 3C:
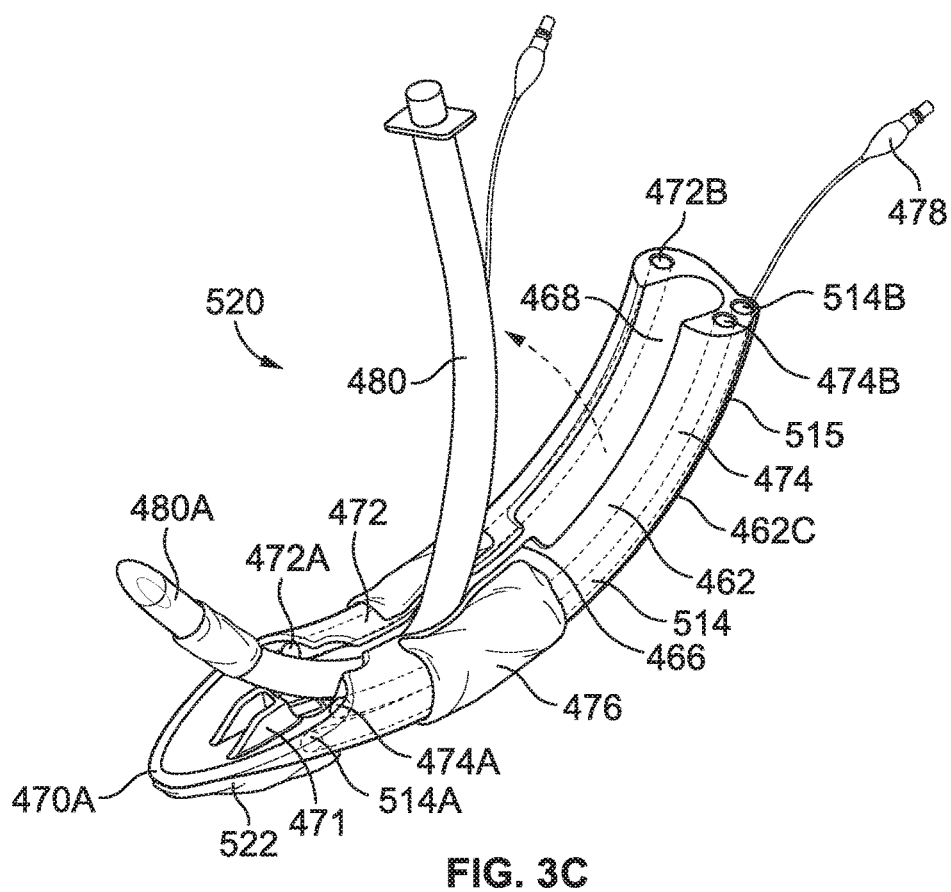
FIG. 3C depicts an endotracheal tube in a process of being removed from the oral airway device of FIG. 3A.

Referring to FIG. 3C, it depicts a removal of the endotracheal tube 480 from the oral airway device 520. The endotracheal tube 480 can be removed from the ETT lumen 468 by pulling the endotracheal tube 480 out through the slit 466. All elements are labeled as in connection with FIGS. 3A-3B.

Figure 4A:
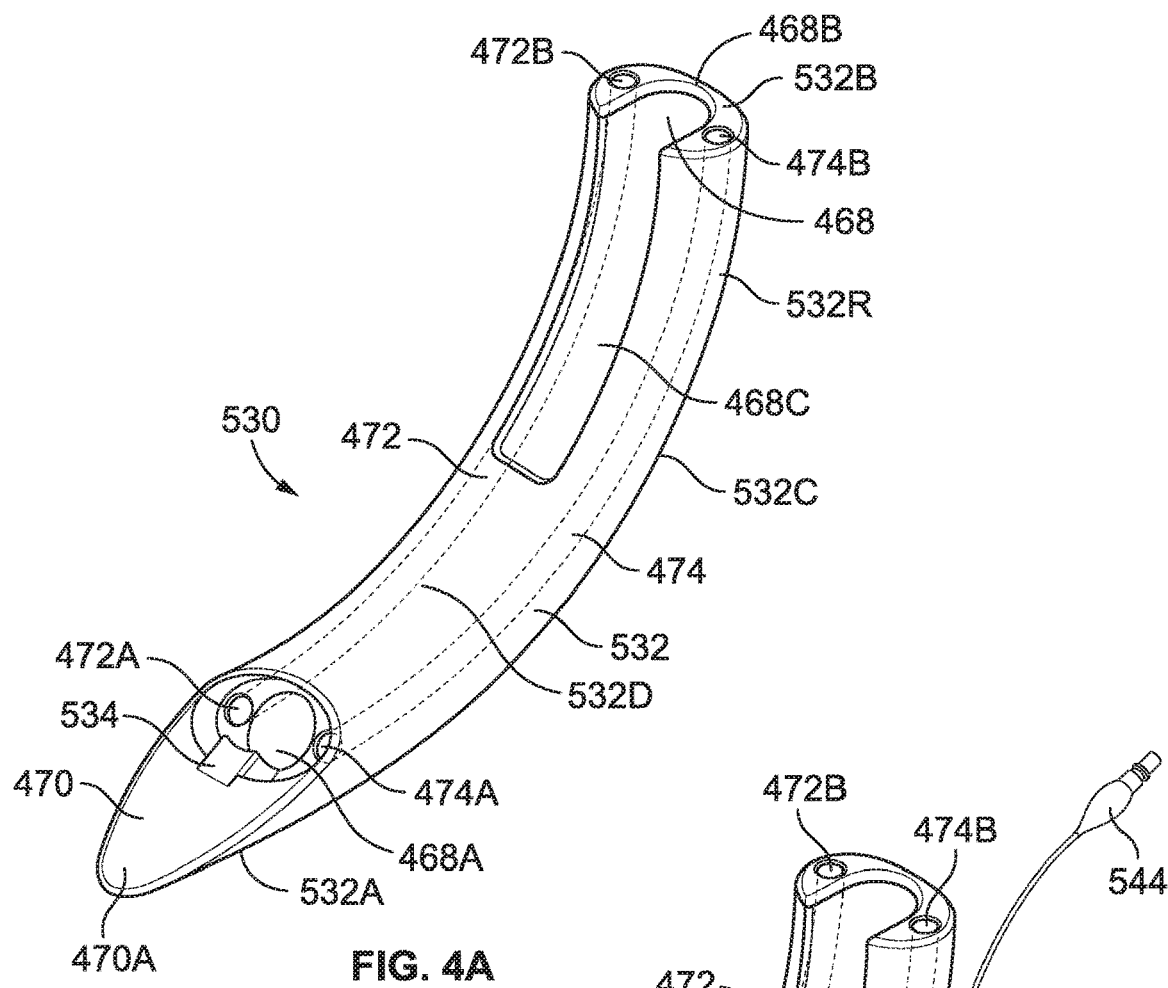
FIG. 4A depicts another embodiment of an oral airway device according to this disclosure.

Referring to FIG. 4A, it depicts another embodiment of an oral airway device provided by this disclosure, generally 530. The oral airway device 530 is a tubal body which is curved such that the oral airway device 530 follows the contour of the roof of a patient's mouth during insertion of the device 530 into the patient.

The curved tubal body of the airway device 530 is made by a wall 532 with a distal end 532A and a proximal end 532B. The wall 532 is curved along the distal-proximal 532A-532B axis such that the wall 532 follows the contour of the roof of a patient's mouth. The wall 532 creates an arch. The wall 532 has a dorsal surface 532C and a ventral surface 532D shown in FIG. 4A along with a right flank 532R. As will be appreciated by a person of skill, because of the arch curvature, a length of the wall 532 is longer on the dorsal surface, 532C, than on the ventral surface, 532D. The ventral surface 532D is in contact with the patient's tongue when the oral airway device 530 is placed in the patient.

The wall 532 encircles the ETT lumen 468. The ETT lumen 468 is hollow and has a distal opening 468A. The ETT lumen 468 has a proximal opening 468B at the proximal end of the wall 532.

The wall 532 recesses into the ETT lumen 468 on the ventral surface 532D such that some proximal portion 468C of the ETT lumen 468 is open and is not covered by the wall 532 on the ventral surface 532D. In this embodiment, there is no slit 466 along the ventral surface 532D of the wall 532. Instead, some proximal portion 468C of the ETT lumen 468 is not covered by the wall 532. This facilitates a loading and removal of a medical device, such as an endotracheal tube, into and from the ETT lumen 468.

At the distal end 532A, the wall 532 ends with a tongue 470 on the dorsal surface 532C. The distal end 470A of the tongue 470 may be an oval or round shape and is tapered at its distal end 470A. The tongue 470 is used to gently push patient's tissues apart during insertion of the oral airway device 530. The tongue 470 protrudes distally from the wall 532.

There is a ramp 534 positioned proximally to the tongue 470 and distally to the distal opening 468A. The ramp 534 elevates and supports a distal end of a device, such as for example an endotracheal tube, inserted into the ETT lumen 468.

The wall 532 has at least two hollow peripheral channels, 472 and 474. The camera channel 472 is hollow and is positioned peripherally to the ETT lumen 468. The camera channel 472 has a proximal opening 472B at the proximal end 532B of the wall 532. The camera channel 472 runs along the distal-proximal 532A-532B axis of the wall 532. The channel 472 ends with a distal opening 472A at the distal end 532A of the wall 532.

A camera (not shown) can be inserted through the proximal opening 472B in the channel 472. The camera can protrude from the distal opening 472A of the channel 472. Any camera described in this disclosure or generally known in the art can be used in the oral airway device 530. The camera is insertable and removable from the camera channel 472. A position of the camera at the distal opening 472A of the camera channel 472 can be adjusted as needed in order to monitor patient's tissues and/or insertion of the oral airway device 530.

In some embodiments, the camera channel 472 is a hollow passage in the wall 532 and the camera channel 472 is completely separated from the ETT lumen 468. In other embodiments, the camera channel 472 is a semi-lumen which is connected to the ETT lumen 468. In further embodiments, there is a slit (not shown in the drawing) that runs along the length of the camera channel 472. The slit of the channel 472 may run along the wall 532 and open externally on the wall 532. A camera can be easily inserted and removed from the camera channel 472 by being pulled through the slit.

The structure of the second channel, 474, is similar to the structure of the first channel 472. The channel 474 is a peripheral hollow channel. The channel 474 runs along the distal-proximal 532A-532B axis of the wall 532. The channel 474 is located peripherally to the ETT lumen 468. As can be seen in FIG. 4A, the channels 472 and 474 flank the ETT lumen 468 which is positioned between the channels 472 and 474.

The channels 472 and 474 may have the same diameter or they may be of a different diameter.

The esophageal channel 474 ends with a distal opening 474A at the distal end 532A of the wall 532. A tool, such as for example a suction tube, (not shown) can be inserted through the proximal opening 474B in the esophageal channel 474. The suction tube (or any other tool inserted in the esophageal channel 474) can protrude from the distal opening 474A of the esophageal channel 474. Any tools described in connection with other embodiments of this disclosure can be used in the oral airway device 530.

The tools are insertable and removable from the esophageal channel 474. A position of the tool at the distal opening 474A can be adjusted as needed in order to manipulate patient's tissues or provide suction. In some embodiments, the esophageal channel 474 is a passage in the wall 432 and the esophageal channel 474 is completely separated from the ETT lumen 468. In other embodiments, the esophageal channel 474 is a semi-lumen which is connected to the ETT lumen 468. In further embodiments, there is a slit that runs along the length of the esophageal channel 474. The slit opens into the ETT lumen 468 or the slit opens the esophageal channel 474 externally on the wall 532.

A relative positioning of the channels 472 and 474 is such that when a camera is inserted in the camera channel 472 and protrudes from the distal opening 472A of the camera channel 472, the camera can visualize a distal end of a tool inserted into the esophageal channel 474 and protruding from the distal opening 474A of the esophageal channel 474. Accordingly, manipulations of the tool are visualized with the camera.

As can be appreciated by a person of skill, in some embodiments, the channels 472 and 474 may be interchangeable, i.e. a camera can be inserted into either of the two channels, as needed, or two cameras can be used simultaneously. In further embodiments, the oral airway device 530 may have more than two channels in the wall 532. These additional channels may be located peripherally to the ETT lumen 468.

Figure 4B:
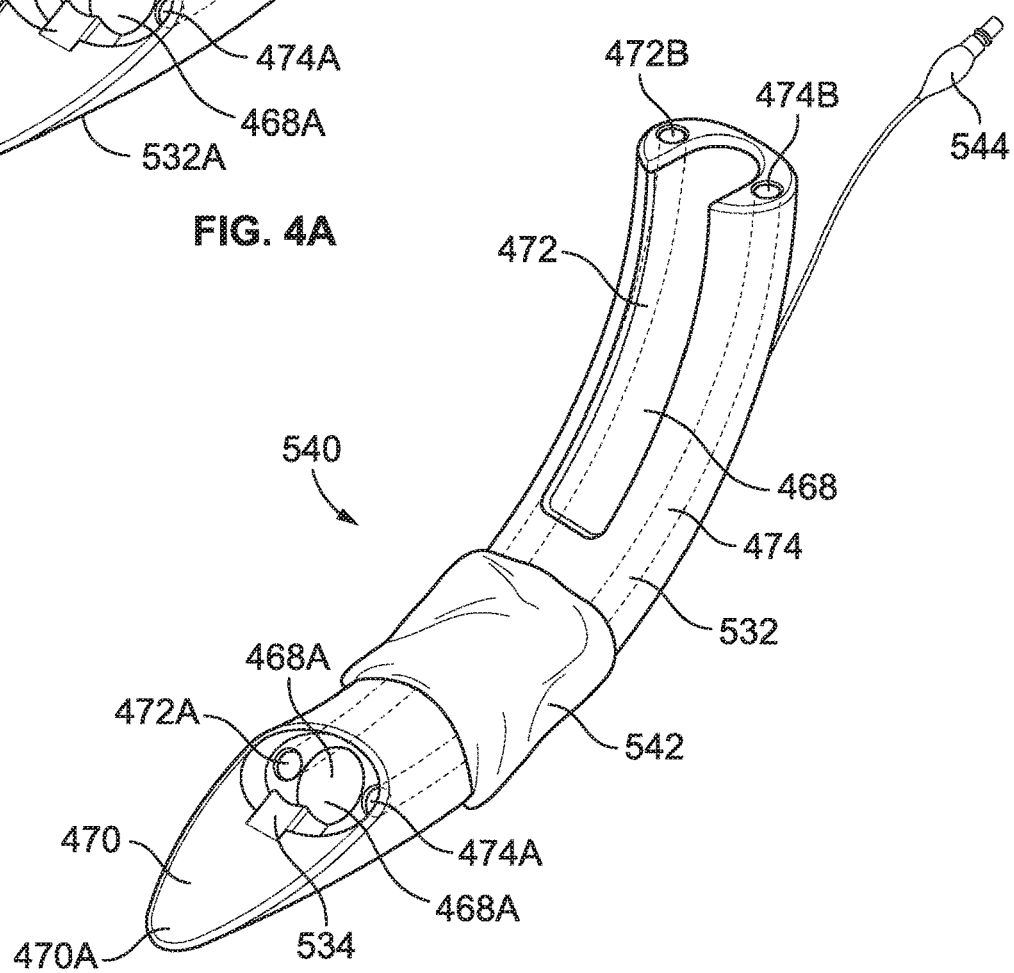
FIG. 4B depicts the oral airway device of FIG. 4A and comprising an inflatable cuff.

Referring to FIG. 4B, it depicts another embodiment of an oral airway device accordingly to this disclosure, generally 540. All of the elements in the device 540 are the same as were described in connection with the oral airway device 530, except the oral airway device comprises an inflatable cuff 542 which is located at the distal portion of wall 532. The inflatable cuff 542 can be inflated with a means 544.

Figure 4C:
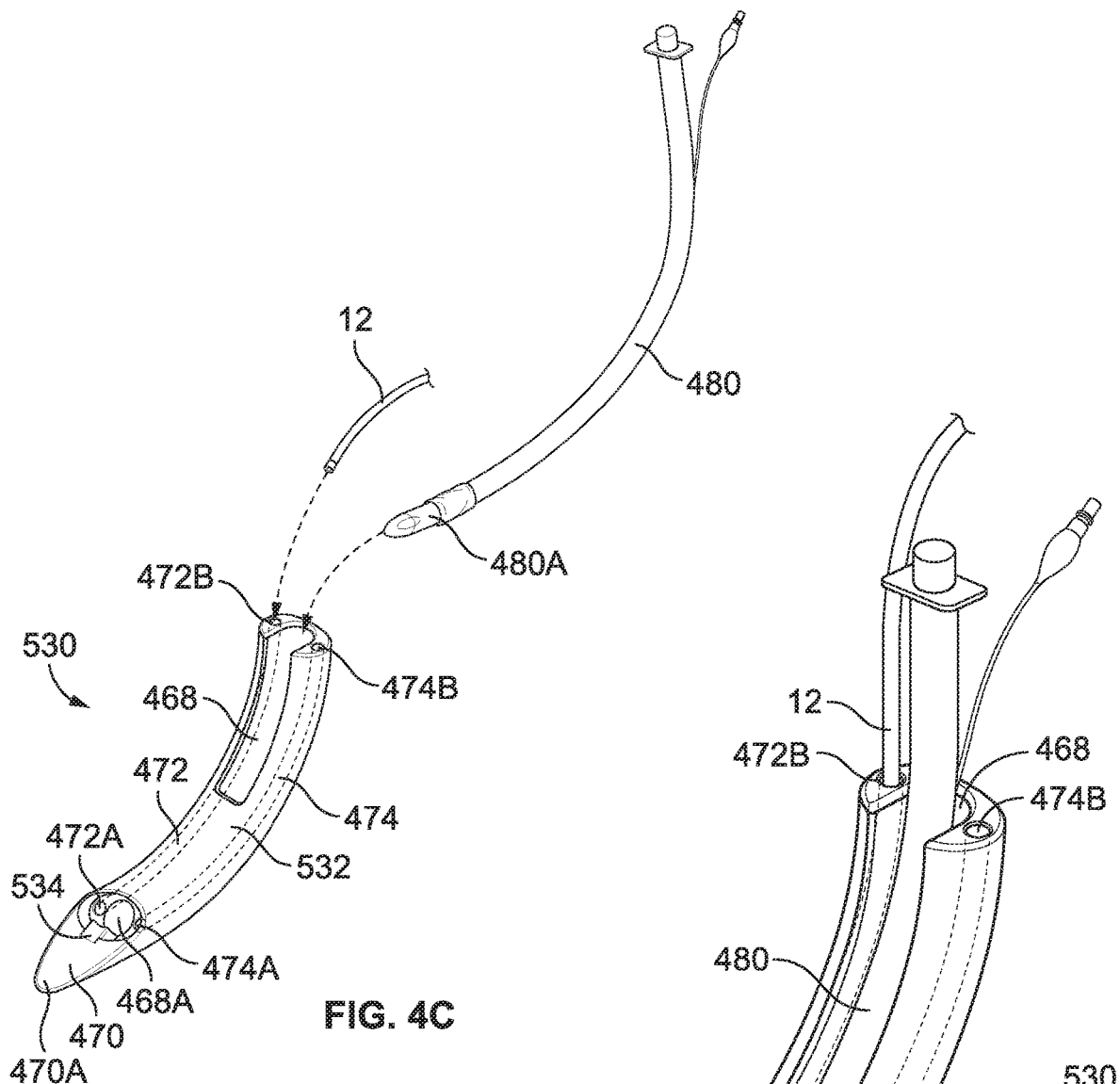
FIG. 4C depicts loading an endotracheal tube and inserting a camera into the oral airway device of FIG. 4A.

Referring to FIG. 4C, it depicts a loading of the endotracheal tube 480 into the ETT lumen 468 of the oral airway device 530. The FIG. 4C also depicts inserting a camera 12 into the camera channel 472. All other elements are numbered as in connection with FIG. 4A.

Figure 4D:
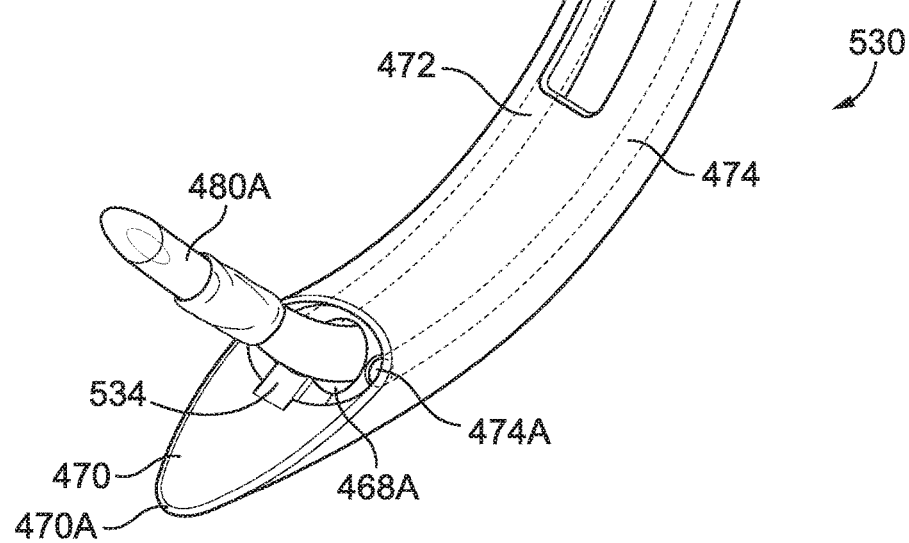
FIG. 4D depicts an endotracheal tube being loaded and a camera being inserted into the oral airway device of FIG. 4A.

FIG. 4D depicts the endotracheal tube 480 loaded in the ETT lumen 468 of the oral airway device 530 and camera 12 being inserted in the camera channel 472. All other elements are numbered as in connection with FIGS. 4A-4C.

Figure 4E:
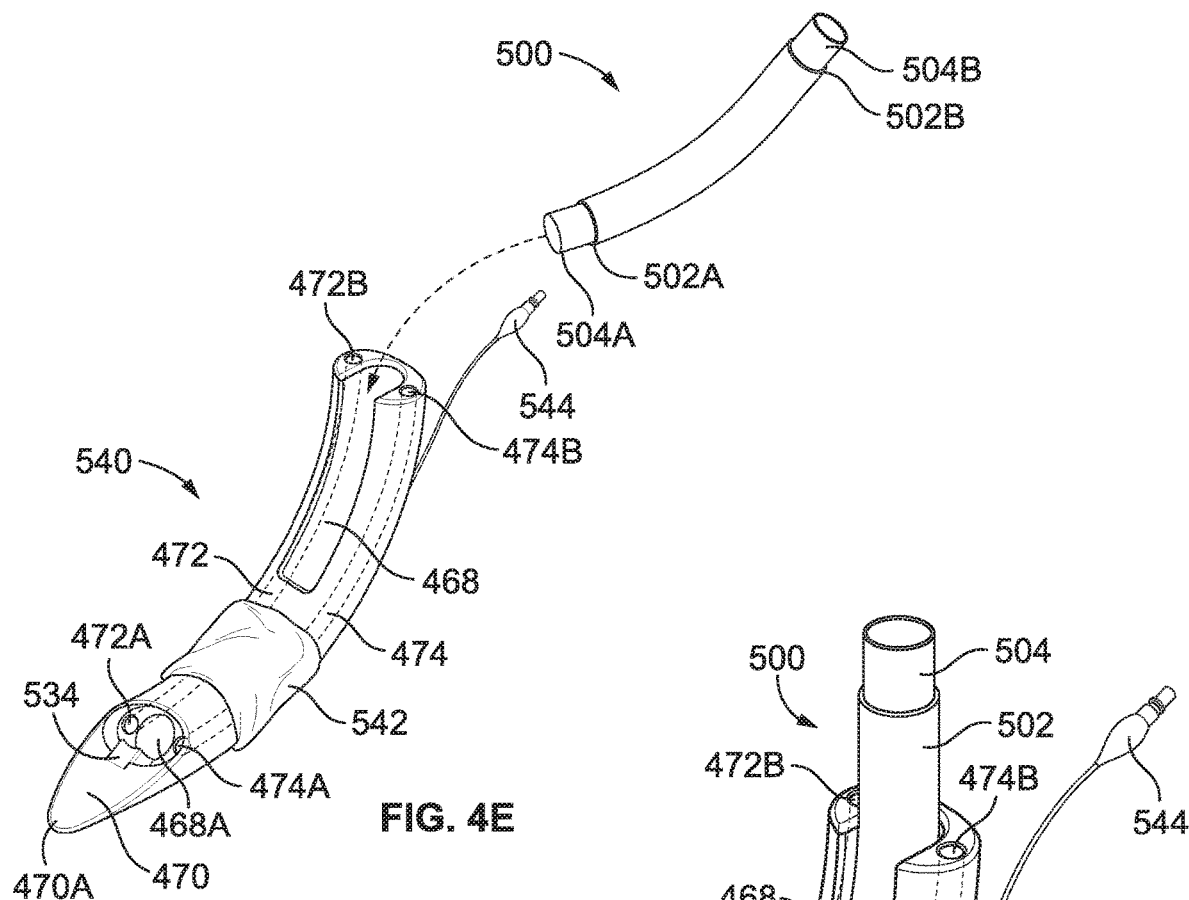
FIG. 4E depicts loading the device of FIG. 1Q into the oral airway device of FIG. 4B.

Referring to FIG. 4E, it depicts an insertion of the device 500 into the ETT lumen 468 of the oral airway device 540 which comprises the inflatable cuff 542. All other elements are numbered as in connection with FIGS. 4A-4D.

Figure 4F:
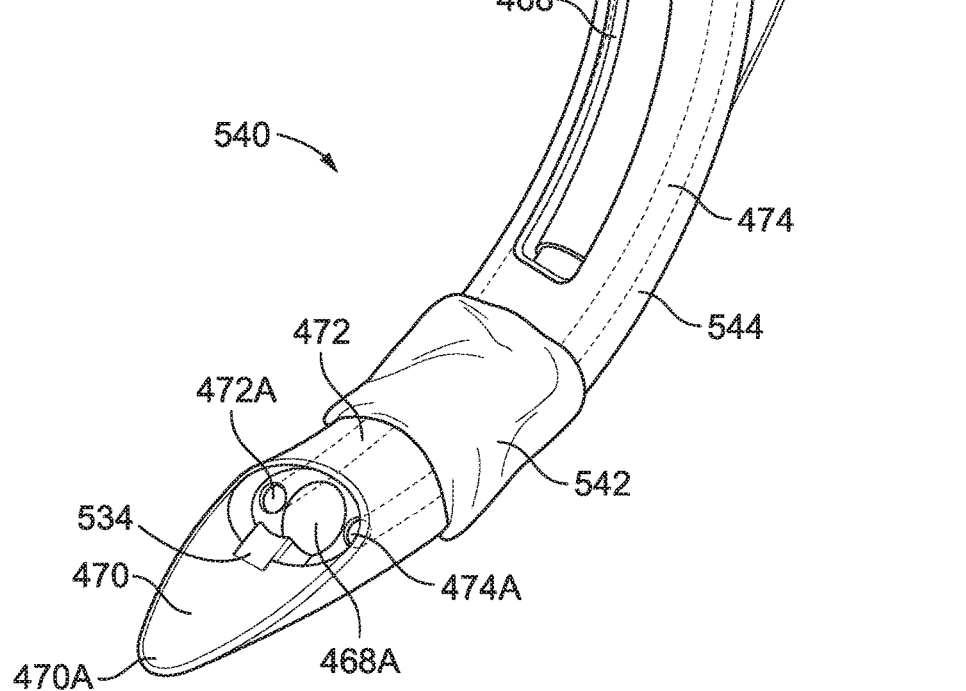
FIG. 4F depicts the device of FIG. 1Q being inserted into the oral airway device of FIG. 4B.

Referring to FIG. 4F, it depicts the device 500 inserted into the ETT lumen 468 of the oral airway device 540 of FIG. 4B. All other elements are numbered as in connection with FIGS. 4A-4E.

Referring to FIG. 4G, it depicts the oral airway device 540 shown from the dorsal surface 532C. All elements are numbered as in connection with FIGS. 4A-4F. A plug 546 is inserted into the proximal opening 472B of the camera channel 472. The plug 546 caps the camera channel 472 and can be used when a closed system needs to be established for ventilation. In the drawing of FIG. 4G, the plug 546 is used in the camera channel 472. In other embodiments, the esophageal channel 474 may be also capped with the plug 546.

Referring to FIGS. 4H and 4I, the plug 456 comprises a hollow cylindrical body 548 and a cap 550 which is attached to the hollow cylindrical body 548 with a bendable string 552. As is shown in FIG. 4H, the cap 550 may cap over the proximal end 548B of the hollow cylindrical body 548. As is shown in FIG. 4I, the cap 550 may be removed from the hollow cylindrical body 548. This allows for air to pass through the hollow cylindrical body 548. The hollow cylindrical body 548 is designed for a tight fit into a channel such as for example, the channel 472 and/or channel 474. Accordingly, the hollow cylindrical body 546 may have a shape of a bottle cork. A diameter of a distal end 548A may be smaller than a diameter of the proximal end 548B. The hollow cylindrical body 548 may comprise ridges 554s.

Figure 4J:
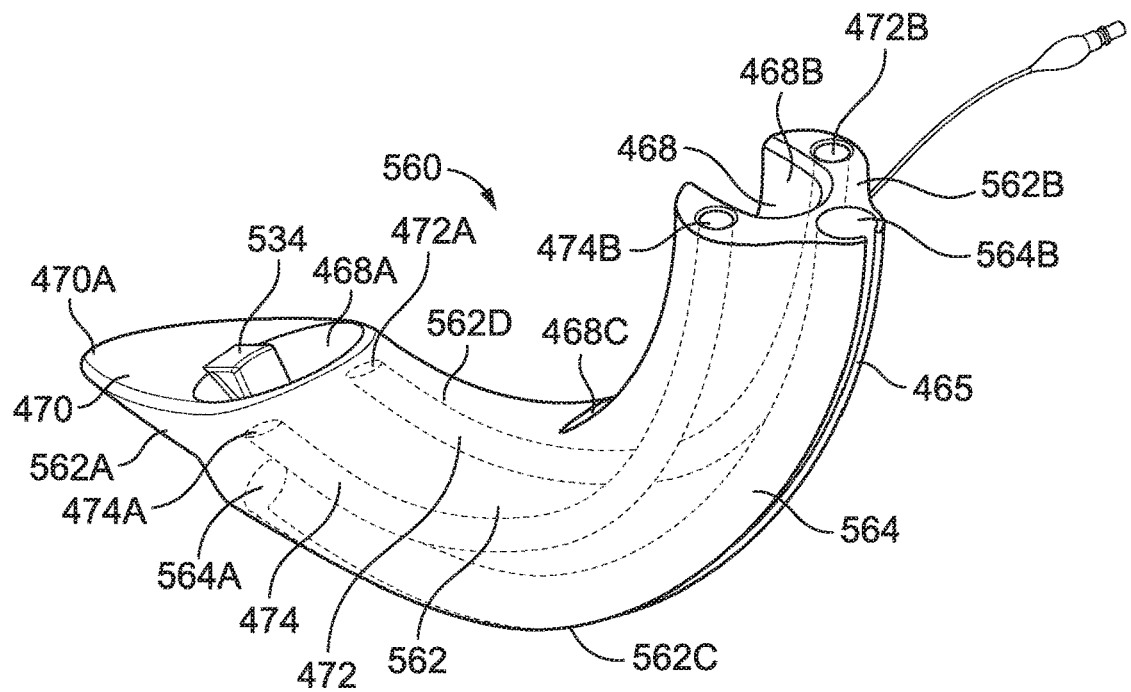
FIG. 4J depicts an oral airway device with a third peripheral channel.

Referring to FIG. 4J, it provides another embodiment of an oral airway device according to this disclosure, generally 560. Just like the oral airway device 530 shown in FIG. 4A, the oral airway device 560 is a tubal body which is curved such that the oral airway device 560 follows the contour of the roof of a patient's mouth during insertion of the device 560 into the patient.

The curved tubal body of the airway device 560 is made by a wall 562 with a distal end 562A and a proximal end 562B. The wall 562 is curved along the distal-proximal 562A-562B axis such that the wall 562 follows the contour of the roof of a patient's mouth. The wall 562 creates an arch. The wall 562 has a dorsal surface 562C and a ventral surface 562D. As will be appreciated by a person of skill because of the arch curvature, a length of the wall 562 is longer on the dorsal surface, 562C, than on the ventral surface, 562D. The ventral surface 562D is in contact with the patient's tongue when the device 560 is placed in the patient.

The wall 562 encircles an ETT lumen 468. The ETT lumen 468 is hollow and has a distal opening 468A. The ETT lumen 468 has a proximal opening 468B at the proximal end of the wall 562. Thus, the ETT lumen 468 runs along the distal-proximal axis 562A-562B.

The wall 562 recesses into the ETT lumen 468 on the ventral surface 562D such that some proximal portion 468C of the ETT lumen 468 is open and is not covered by the wall 562 on the ventral surface 562D. Accordingly, some proximal portion 468C of the ETT lumen 468 is not covered by the wall 562. Keeping the portion 468C of the ETT lumen 468 not enclosed with the wall 564 on the ventral surface 462D helps with loading into and removing from the central lumen 468 a medical device, such as an endotracheal tube.

At the distal end 562A, the wall 562 ends with a tongue 470 on the dorsal surface 562C. The distal end 470A of the tongue 470 may be of an oval or round shape. The tongue 470 is tapered at its distal end 470A. The tongue 470 is used to gently push patient's tissues apart during insertion of the device 560. The tongue 470 protrudes distally from the wall 562.

There is a ramp 534 positioned proximally to the tongue 470 and distally to the distal opening 468A. The ramp 534 elevates and supports a distal end of a device, such as for example an endotracheal tube, inserted into the ETT lumen 468.

The wall 562 has at least two hollow peripheral channels, 472 and 474. The camera channel 472 is hollow and is positioned peripherally to the ETT lumen 468. The camera channel 472 has a proximal opening 472B at the proximal end 562B of the wall 562. The camera channel 472 runs along the distal-proximal 562A-562B axis of the wall 562. The camera channel 472 ends with a distal opening 472A at the distal end 562A of the wall 562.

A camera (not shown) can be inserted through the proximal opening 472B in the camera channel 472. The camera can protrude from the distal opening 472A of the camera channel 472. Any camera described in this disclosure or generally known in the art can be used in the oral airway device 560. The camera is insertable and removable from the channel 472. A position of the camera at the distal opening 472A of the channel 472 can be adjusted as needed in order to monitor patient's tissues and/or insertion of the device 530.

In some embodiments, the camera channel 472 is a passage in the wall 562 and the camera channel 472 is completely separated from the ETT lumen 468. In other embodiments, the camera channel 472 is a semi-lumen which is connected to the ETT lumen 468. In further embodiments, there is a slit (not shown in the drawing) that runs along the length of the camera channel 472. The slit of the camera channel 472 may run along the wall 562 externally.

The structure of the second channel, 474, is similar to the structure of the first channel 472. The channel 472 is a peripheral hollow channel. The channel 474 runs along the distal-proximal 462A-462B axis of the wall 462. The channel 474 is located peripherally to the ETT lumen 468. As can be seen in FIG. 4J, the channels 472 and 474 flank the ETT lumen 468 which is positioned between the channels 472 and 474.

The channels 472 and 474 may be of the same diameter or they may be of a different diameter.

The channel 474 ends with a distal opening 474A at the distal end 562A of the wall 562.

The tools are insertable and removable from the channel 474. A position of the tool at the distal opening 474A can be adjusted as needed in order to manipulate patient's tissues or to provide suction. In some embodiments, the channel 474 is a passage in the wall 564 and the channel 474 is completely separated from the ETT lumen 468. In other embodiments, the channel 474 is a semi-lumen which is connected to the ETT lumen 468. In further embodiments, there is a slit that runs along the length of the channel 474. The slit opens into the ETT lumen 468.

A relative positioning of the channels 472 and 474 is such that when a camera is inserted in the channel 472 and protrudes from the distal opening 472A of the channel 472, the camera can visualize a distal end of a tool inserted into the channel 474 and protruding from the distal opening 474A of the channel 474. Accordingly, manipulations of the tool are visualized with the camera.

As can be appreciated by a person of skill, in some embodiments, the channels 472 and 474 may be interchangeable, i.e. a camera can be inserted into either of the two channels, as needed. In some embodiments, two cameras can be used at the same time.

As can be seen in FIG. 4J, the oral airway device 560 comprises a third channel, 564, which runs along the dorsal-ventral axis 562A-562B on the dorsal surface 562C. In the embodiment of FIG. 4J, the channel 564 is a semi-lumen which opens to the dorsal surface 562C. The channel 564 also has a proximal opening 564B. The channel 564 can be used for loading a stomach suction tube or a scope for the EGD procedure which can be placed in a patient in one step and together with an endotracheal tube when both devices are loaded into the oral airway device 560.

The stomach suction tube or scope can be then easily removed from the channel 564 while the oral airway device 560 still remains inserted into a patient. Because the channel 564 has a groove-like shape it holds the stomach suction tube or scope in place and prevents it from sliding and slipping. The length of the channel 564 may vary. In some embodiments the channel 564 runs along all or most all of the dorsal surface 562C of the wall 562. In these embodiments, the channel 564 ends at or near the distal end 562A of the wall 562. In other embodiments, the channel 564 runs only along a portion of the wall 562 and it ends at any place proximally to the distal end 562A of the wall 562.

Figure 4K:
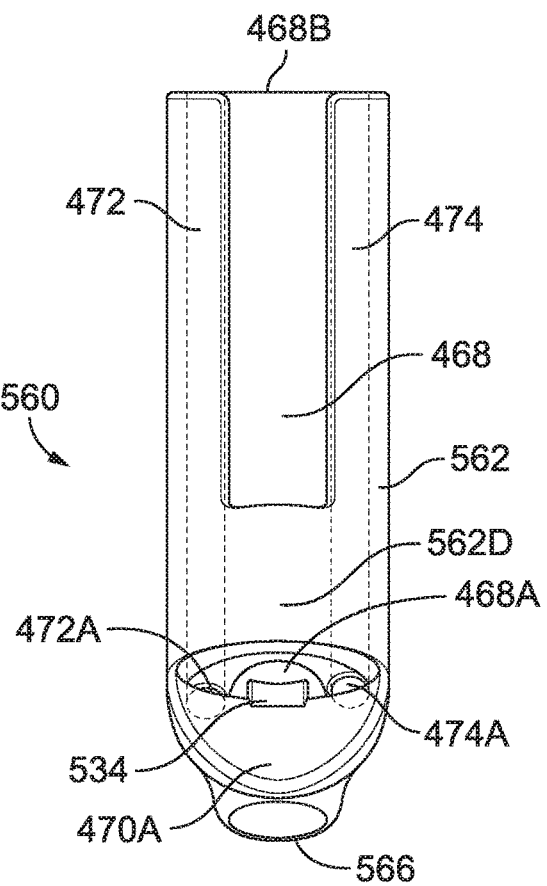
FIG. 4K depicts a ventral surface of the oral airway device of FIG. 4J.

Referring to FIG. 4K, it is a ventral view of the oral airway device 560 from the ventral surface 562D. All elements are numbered as in connection with FIG. 4J

The distal opening 472A to the camera channel 472 is shown. The distal opening 474A to the esophageal channel 474 is also shown. The proximal portion 468C of the ETT lumen 468 is not covered by the wall 562 on the ventral surface 562D. The ramp 534 is shown. The distal portion 470A of the tongue 470 is also shown.

As shown in the drawing of FIG. 4K, the oral airway device 560 may comprise a loop 566 attached externally near the distal end 562A of the wall 562. One of the functions for the loop 566 is to hold in place a stomach suction tube or scope loaded into the channel 564. The stomach suction tube or any other tube or tool may be pulled through the loop 566. Accordingly, the loop 566 secures the positioning of the stomach suction tube or any other tube or tool on the oral airway device 560 and prevents the stomach suction tube or any other tube or tool from separating from the oral airway device 560. A person of skill will appreciate that the loop 566 may be attached to the oral airway device 560 or any other of the oral airway devices provided in this disclosure, including the oral airway device 460, 510, 520, 530 or 540.

In another aspect, the present disclosure provides oral airway devices which comprise channels, but do not comprise the endotracheal tube (ETT) lumen 468. These oral airway devices will be now described with reference to FIGS. 5A-5F and FIG. 6.

Figures 5A, 5B, 5C:
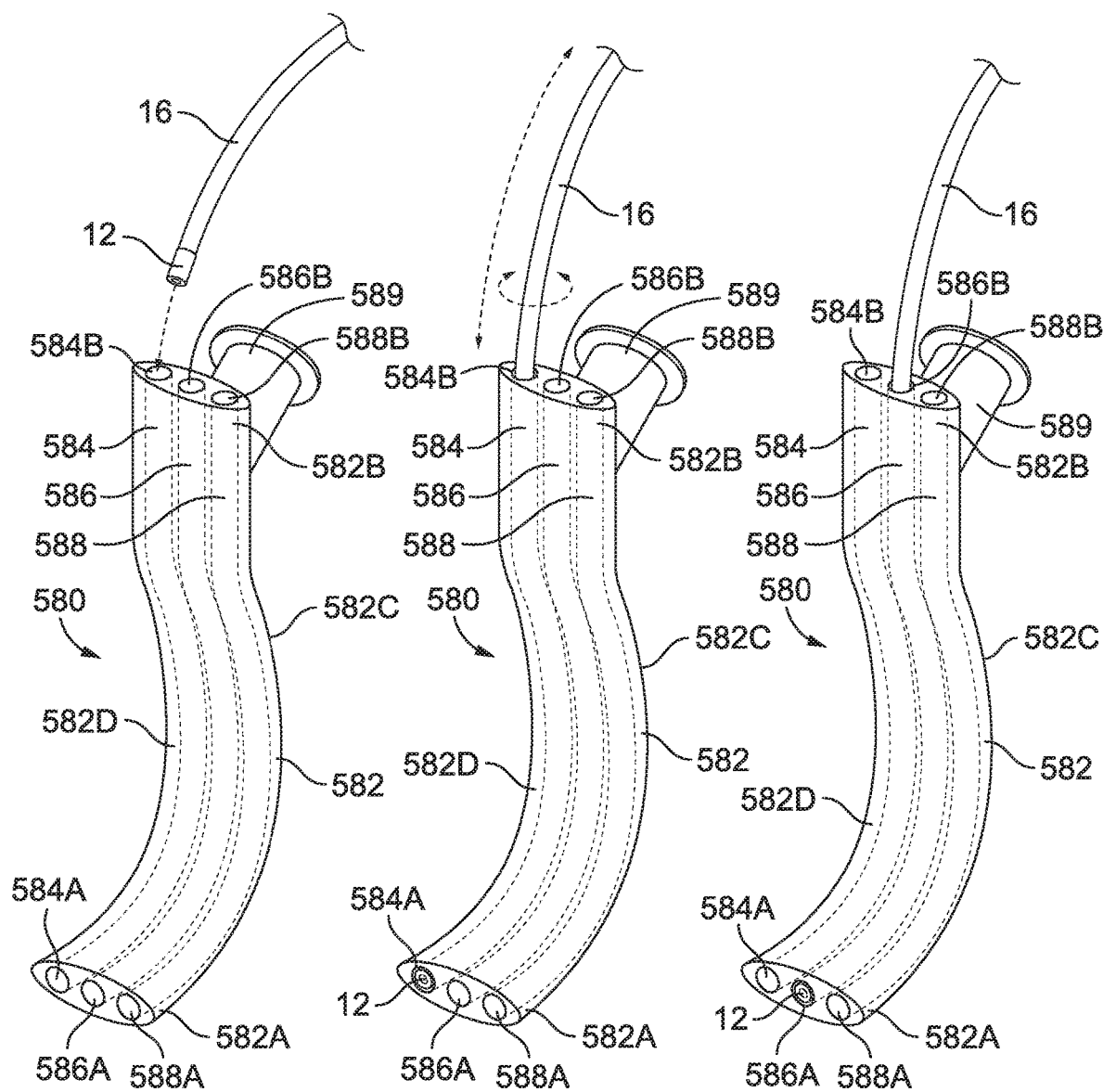
FIG. 5A depicts another embodiment of an oral airway device according to this disclosure.
FIG. 5B depicts a camera being inserted into one of the channels of the oral airway of FIG. 5A.
FIG. 5C depicts a camera being inserted into another channel of the oral airway of FIG. 5A.

Referring to FIG. 5A, it provides another embodiment of an oral airway device, generally 580. The oral airway device 580 comprises a tubal body created by a wall 582 with a distal end 582A and a proximal end 582B. The oral airway device 580 may comprise a handle 589 located near the proximal end 582B which may aid a practitioner in manipulating the oral airway device 580 during insertion or removal. The handle 589 may be adhered to the wall 582 or the handle 589 may be attached to the wall 582 removably such that the handle 589 is removed after the insertion of the oral airway device 580 has been completed.

The wall 582 is curved along the distal-proximal axis 582A-582B and follows the contour of the roof of a patient's mouth during insertion of the oral airway device 580 into the patient. The wall 582 has a dorsal surface, 582C, and a ventral surface, 582D. The wall 582 creates an arch which follows the contour of the roof of a patient's mouth such that the ventral surface 582D is in contact with the patient's tongue when the device 580 is inserted in the patient.

The oral airway device 580 has several hollow channels, 584, 586 and 588 which run through the tubal body 582. In other embodiments, the oral airway device 580 may have more or fewer than 3 channels.

Each of the channels, 584, 586 and 588, opens with a proximal opening 584B, 586B, and 588B, respectively, at or near the proximal end 582B of the wall 582. Each of the channels, 584, 586 and 588, opens with a distal opening 584A, 586A, and 588A, respectively, at or near the distal end 582A of the wall 582. In some other embodiments, a cuff (not shown), either inflatable or non-inflatable, is attached around the perimeter of the wall 582 in the near proximity to the distal end 582A of the wall 582.

In the embodiment of FIG. 5A, the oral airway device 580 comprises three channels. In other embodiments, the oral airway device 580 may comprise more than three, i.e. 4 or 5, or fewer than 3 channels, i.e. 2 or 1. The channels 584, 586 and 588 are passages in the tubal body 582. The channels 584, 586 and 588 can be used for hosting various devices. As shown in FIG. 5A, a camera 12 can be inserted into one of the channels, 584, 586 and/or 588.

FIG. 5B depicts the camera 12 being inserted into the channel 584 of the oral airway device 580. All elements are numbered as in connection with FIG. 5A.

FIG. 5C depicts the camera 12 being inserted into the channel 586. Accordingly, the oral airway device 580 is compatible with a camera and more than one camera can be used. At least one of the distal openings 584A, 586A and/or 588A is not sealed. This allows for a tool or the camera 12 to protrude distally from the oral airway device 580. The camera 12 is attached to a cable 16. The cable 16 can be used to move the camera 12 further distally or to remove the camera 12 from the oral airway device 580 while the oral airway device 580 remains inserted in a patient. The oral airway device 580 may be used for hosting a number of various tools, for example a bougie and a suction tube, which can be manipulated under continuation visualization by a camera.

In addition to embodiments in which a camera is insertable to one or more channels, a camera can be built-in the wall 582 in other embodiments. The oral airway device 580 can be used in combination with several cameras which would provide visualization of the patient's tissues from different positions.

FIGS. 5D and 5E are zoom-in views of the distal end 582A of the oral airway device 580. The distal opening 584A of the channel 584 and the distal opening 588A of the channel 588 are shown. The camera 12 is inserted in the channel 586 and can be seen at the distal opening 586A of the channel 586. In the embodiment of FIG. 5D, the camera 12 comprises a light source 18. In the embodiment of FIG. 5E, the light source 18 is incorporated into the wall 582.

FIG. 5F depicts a bougie 590 inserted into the channel 586 of the oral airway device 580. A distal end 590A of the bougie 590 protrudes distally from the distal end 586A of the channel 586. The bougie 590 or any other tool inserted into one of the channels 584, 586 and/or 588 can be manipulated under a continuous visualization from the camera 12 as shown in FIGS. 5A-5E.

Figure 6:
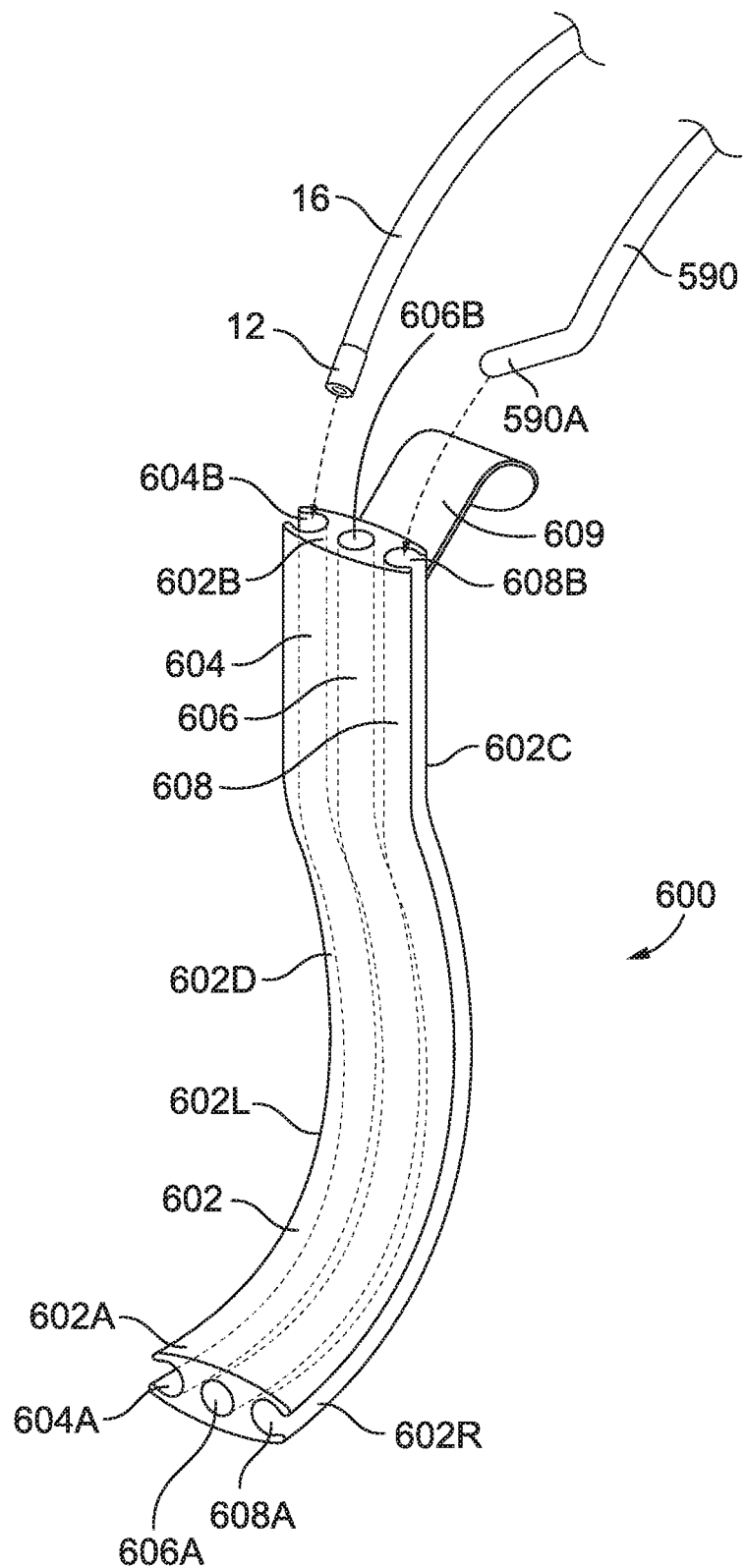
FIG. 6 depicts an oral airway device with peripheral channels opening externally along the oral airway device body.

FIG. 6 depicts another embodiment of an oral airway device with channels, generally 600. The oral airway device 600 comprises a tubal body created by a wall 602 with a distal end 602A and a proximal end 602B. The wall 602 is curved along the distal-proximal axis 602A-602B and follows the contour of the roof of a patient's mouth during insertion of the device 600 into the patient. The wall 602 has a dorsal surface, 602C, and a ventral surface, 602D. In some embodiments, the oral airway device 600 may comprise a handle 609 attached to the wall 602 on the dorsal surface 602C in proximity to the proximal end 602B. The handle 609 aids a practitioner in manipulating the device 600 during insertion and removal. The handle 609 may be attached removably such that the handle 609 can be separated from the wall 602 after the oral airway device 600 has been placed.

The wall 602 creates an arch which follows the contour of the rood of a patient's mouth such that the ventral surface 602D is in contact with a patient's tongue when the device 580 is inserted in the patient. The oral airway device 600 has several channels, 604, 606 and 608 which run through the wall 602 along the distal-proximal 602A-602B axis.

Each of the channels, 604, 606 and 608, opens with a proximal opening 604B, 606B, and 608B, respectively, at the proximal end 602B of the wall 602. Each of the channels, 604, 606 and 608, opens with a distal opening 604A, 606A, and 608A, respectively, at the distal end 602A of the wall 602. In the embodiment of FIG. 6, the oral airway device 600 comprises three channels. In other embodiments, this oral airway device 600 may comprise more than three, for example, 4 or 5, or fewer than 3 channels, for example, 2 or 1.

The channel 608 is a peripheral channel. It is a semi-lumen which opens externally on the wall 602. Accordingly, the channel 608 can be described as a recess in the wall 602 which runs along the distal-proximal axis 602A-602B. The channel 608 creates a groove into which a camera, tool or a tube can be placed. Because of its groove-like shape, the channel 608 keeps the camera, tool or tube in place and prevents it from jamming. However, as the channel 608 is open along the distal-proximal axis 602A-602B, it is easy to remove the camera, tool or tube from the channel 608 while the oral airway device 600 still remains inserted and in place in a patient. In the drawing of FIG. 6, the channel 608 opens externally to the right flank 602R of the wall 602. In other embodiments, the channel 604 may open to the dorsal surface 602C or ventral surface 602D of the wall 602.

The channel 606 is a hollow passage in the wall 602. The channel 604 has the same structure as the channel 608 in the embodiment of FIG. 6.

The channel 604 is located peripherally to the channel 606. The channel 604 is a semi-lumen which opens externally from the wall 602. In the drawing of FIG. 6, the channel 604 opens eternally to the left flank 602L of the wall 602. In other embodiments, the channel 604 may open to the dorsal surface 602C or ventral surface 602D of the wall 602.

Accordingly, the channel 604 can be viewed as a recess in the wall 602 which runs along the distal-proximal axis 602A-602B. The channel 604 creates a groove into which a camera, tool or a tube can be placed. Because of its groove-like shape, the channel 604 keeps the camera, tool or tube in place and prevents it from jamming. However, as the channel 604 is open along the distal-proximal axis 602A-602B, it is easy to remove the camera, tool or tube from the channel 608 while the oral airway device 600 still remains inserted and in place in a patient.

As is shown in FIG. 6, the camera 12 attached to the cable 16 can be placed in the channel 604 while a bougie 590 can be placed in the channel 608. Because the channel 608 is a groove, the bougie 590 with the distal end 590A being bended can still be placed in the channel 608. The distal end 590A of the bougie 590 is placed distally to the distal opening 608A of the channel 608. The rest of the bougie 590 is then placed inside of the channel 608.

It will be appreciated that while in the embodiment of FIG. 6, both peripheral channels 604 and 608 are semi-lumens which are open externally along the distal-proximal 602A-602B axis of the wall 602, in other embodiments the oral airway device 600 may comprise only one peripheral channel and/or only one of the two peripheral channels may be opening externally along the distal-proximal 602A-602B axis of the wall 602. In the embodiment of FIG. 6, the opening is a gap-like. In further embodiments, the opening may be a slit.

As it was already described in connection with drawings of FIGS. 5A-5F, any of the three channels, 604, 606 and/or 608, may be used for inserting a camera or a tool including for example, forceps, a suction tube, a stethoscope, a temperature probe, a bougie or a stylet.

In some embodiments, the oral airway device 600 may comprise an inflatable or non-inflatable cuff (not shown) attached around the perimeter of the wall 602 in the near proximity to the distal end 602A. In the embodiments where peripheral channels open with grooves to the wall 602, the cuff may also have slits that align with the grooves such that the cuff does not run over the grooves.

Further embodiments of this disclosure provide an adaptor which converts a medical tool or tube, such as for example an endotracheal tube, into a medical tool or tube which is compatible with a camera.

Figure 7A:
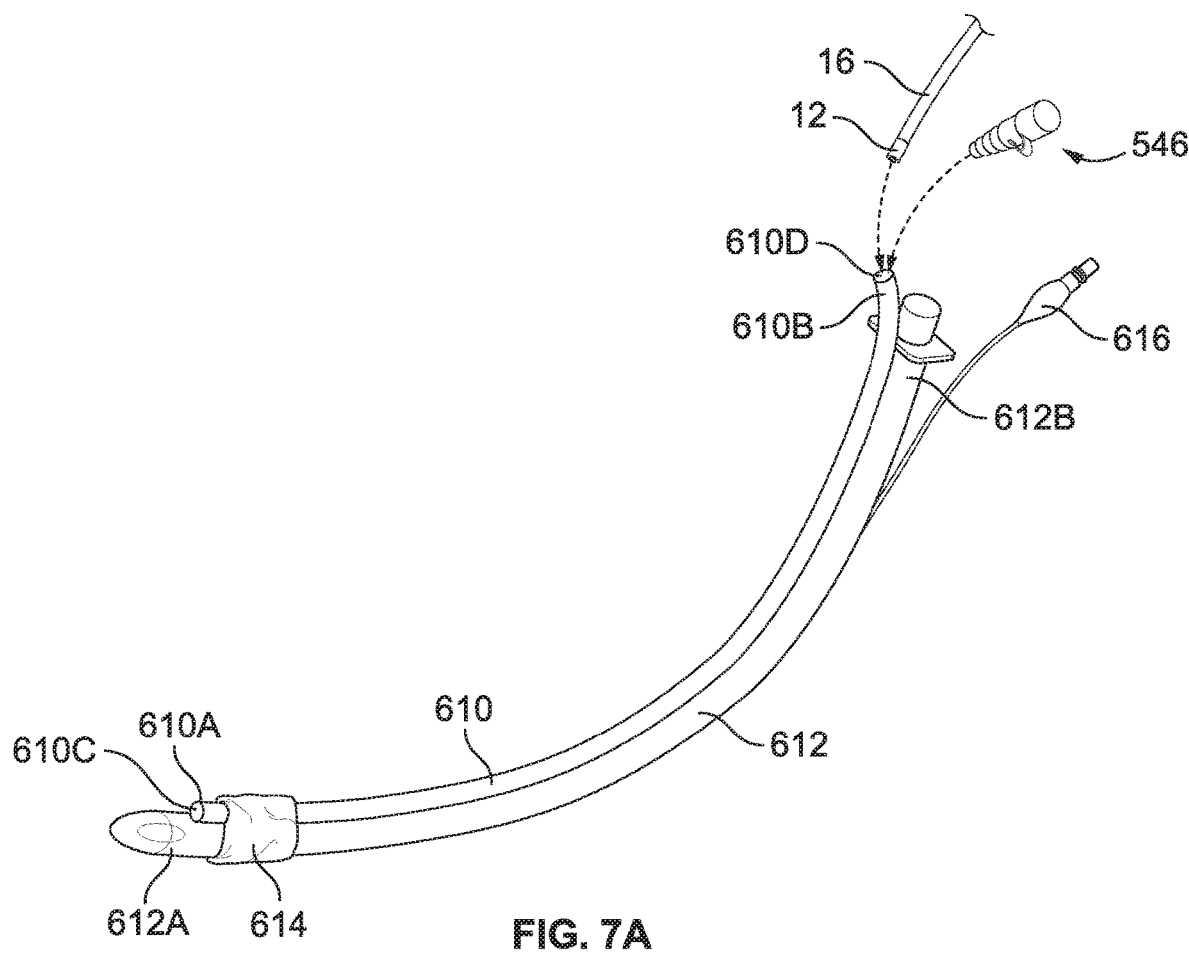
FIG. 7A depicts one embodiment of an adaptor being combined with an endotracheal tube.

One embodiment of the adaptor is shown in FIG. 7A. In this embodiment, the adaptor 610 is a plastic tube with a distal end 610A and a proximal end 610B which is combined with an endotracheal tube 612. The adaptor 610 may have a slit which runs along the tube from the proximal end 610B to the distal end 610A.

The endotracheal tube has a distal end 612A and a proximal end 612B. There is an inflatable cuff 614 which wraps around the endotracheal tube 612 in a proximity to the distal end 612A. The distal end 610A of the adaptor 610 is located distally to the cuff 614. The adaptor 610 runs along the distal-proximal axis 612A-612B. The adaptor 610 may be attached, such as for example by being adhered to the endotracheal tube 612 along the distal-proximal axis 612A-

612B. In alternative, the adaptor 610 may be placed under the cuff 614 such that the adaptor 610 may glide along the endotracheal tube 612.

The proximal end 610B of the adaptor 610 protrudes proximally from the proximal end 612B of the endotracheal tube 612. The cuff 614 can be inflated with a means 616 once the endotracheal tube 612 is placed in a patient.

The adaptor 610 is a hollow tube which may or may not have a slit and which has an opening 610C at the distal end 610A and an opening 610D at the proximal end 610B.

A camera 12 with cable 16 can be placed inside the adaptor 610 through the proximal opening 610D. When not in use, the camera 12 can be removed from the adaptor 610. The proximal opening 610D can be plugged with the plug 546 if a closed system needs to be established for ventilating a patient. The distal end 610C of the adaptor 610 is not sealed. Accordingly, the camera 12 can protrude distally from the adaptor 610. In the embodiment of FIG. 7A, the adaptor 610 is placed under the cuff 614 which may be used for holding the adaptor 610 together with the endotracheal tube 612. At least in some embodiments, the adaptor 610 can slide distally and proximally along the endotracheal tube 612.

Figure 7B:
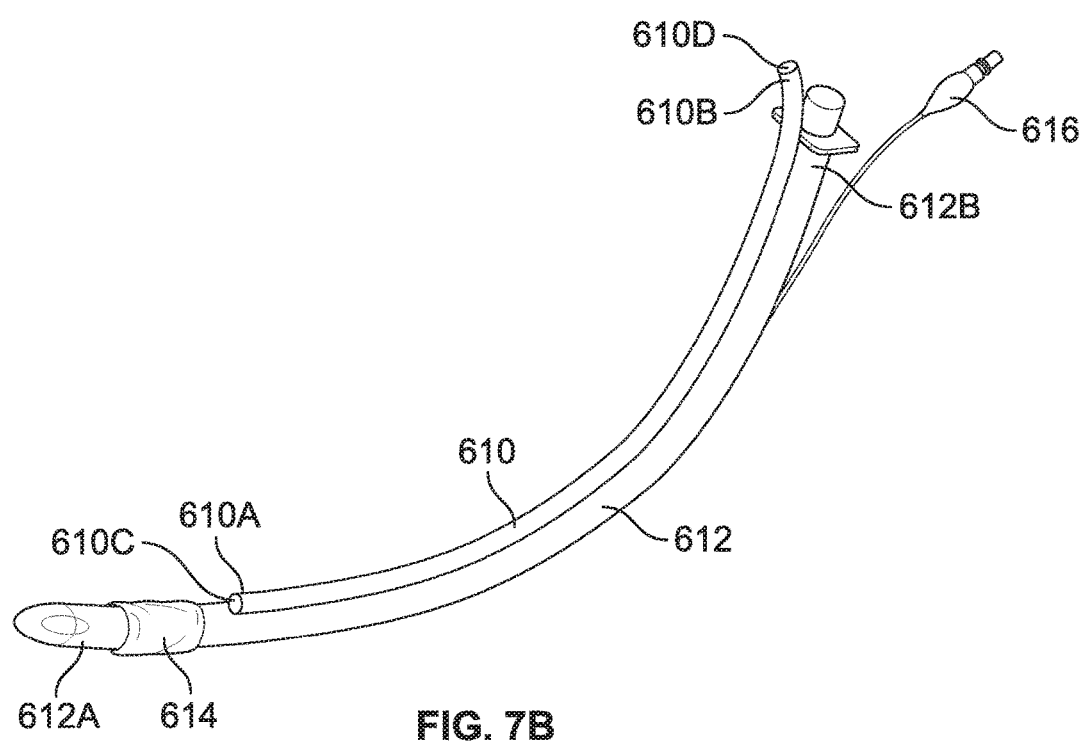
FIG. 7B depicts another embodiment of an adaptor being combined with an endotracheal tube.

Referring to FIG. 7B, the distal end 610A of the adaptor 610 is positioned proximally to the cuff 614. All other elements are numbered as was discussed in connection with FIG. 7A. In the embodiment of FIG. 7B, the adaptor 610 may be attached to the endotracheal tube 612 such that the adaptor 610 can still slide along the distal-proximal axis 612A-612B. In alternative, the adaptor 610 may be adhered to the endotracheal tube 612 and it does not slide.

Figure 8A:
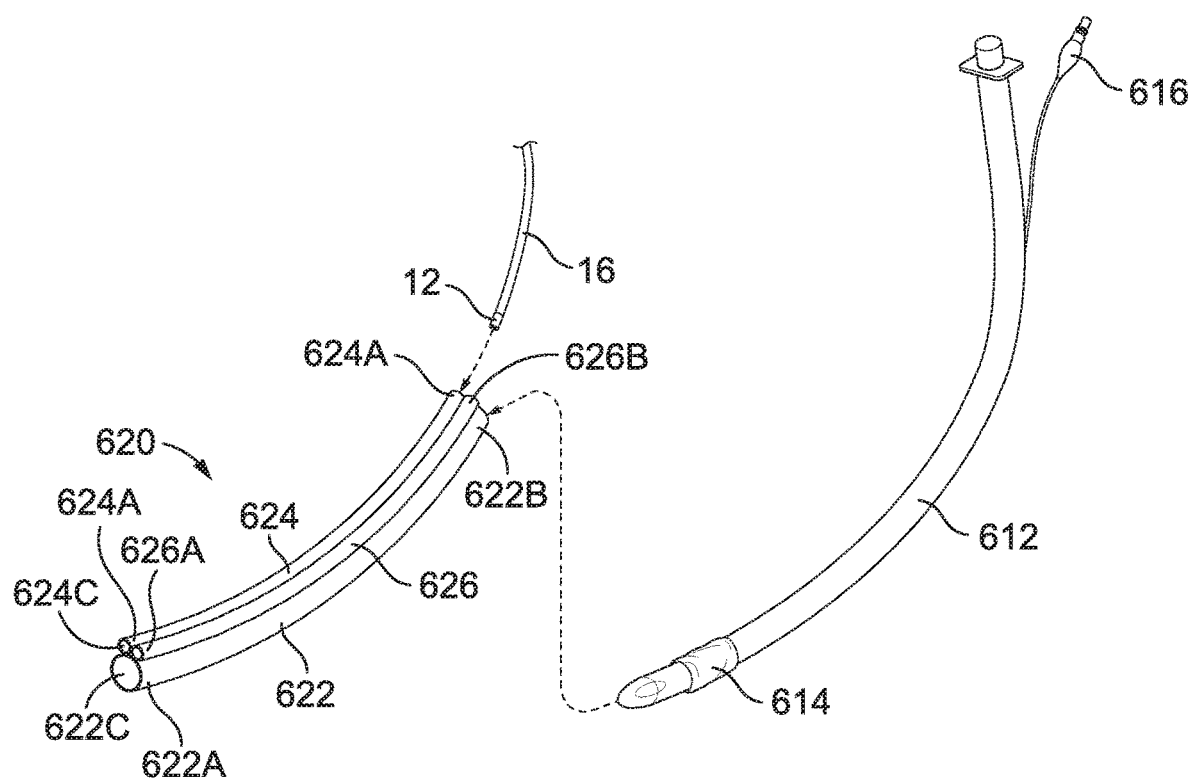
FIG. 8A is a further embodiment of an adaptor according to this disclosure.

Referring to FIG. 8A, it provides a further embodiment of an adaptor according to this disclosure, generally 620. The adaptor 620 comprises a hollow tube 622 with a distal end 622A and a proximal end 622B. The hollow tube 622 may have a slit (not shown) which runs the distal/proximal axis 622A/622B.

The hollow tube 622 has an opening 622C at the distal end 622A and an opening 622D (not shown in the drawing of FIG. 8A) at the proximal end 622B. The diameter of the hollow tube 622 is compatible with a diameter of an endotracheal tube 612. Accordingly, the endotracheal tube 612 can be inserted into the hollow tube 622. If a slit is present, it helps with insertion and removal of the endotracheal tube 612 from the hollow tube 622.

At least one second hollow tube 624 is attached to the hollow tube 622. The second hollow tube 624 has a distal end 624A and a proximal end 624B. The second hollow tube 624 has an opening 624C at the distal end 624A. The second hollow tube 624 has an opening 624D at the proximal end 624B. The distal end 624A of the second hollow tube 624 is aligned with the distal end 622A of the hollow tube 622. The proximal end 624B of the second hollow tube 624 is aligned with the proximal end 622B of the hollow tube 622.

A diameter of the second hollow tube 624 is compatible with a camera 12 such that the camera 12 connected to the cable 16 can be inserted through the proximal opening 624D into the second hollow tube 624. Since the distal end 624C is not sealed, the camera 12 can protrude distally from the second hollow tube 624. At least in some embodiments, the distal end 624A of the tube 624 may be sealed with a transparent window which prevents the camera 12 from coming in contact with bodily fluids.

The adaptor 620 may comprise one or more additional hollow tubes. In FIG. 8A, a third hollow tube 626 is shown. In other embodiments, the third hollow tube may be absent or the adaptor 620 may comprise a plurality of hollow tubes 626. The hollow tube 626 is attached to the hollow tube 620. The hollow tube 626 has a distal end 626A and a proximal end 626B. The hollow tube 626 has an opening 626C at the distal end 626A. The hollow tube 626 has an opening 626D at the proximal end 626B.

The distal end 626A of the hollow tube 626 is aligned with the distal end 622A of the hollow tube 622. The proximal end 626B of the hollow tube 626 is aligned with the proximal end 622B of the hollow tube 622. A diameter of the hollow tube 626 is compatible with a camera 12 such that the camera 12 connected to the cable 16 can be inserted through the proximal opening 626D into the hollow tube 626. Since the distal end 626C is not sealed, the camera 12 can protrude distally from the hollow tube 626. The hollow tubes 624 and 626 can be used interchangeable for hosting a camera and a tool, such as for example a bougie and/or stylet. A camera can be inserted into one of the hollow tubes 624 or 626, while a tool can be inserted into the other. An endotracheal tube is loaded into the hollow tube 622.

Figure 8B:
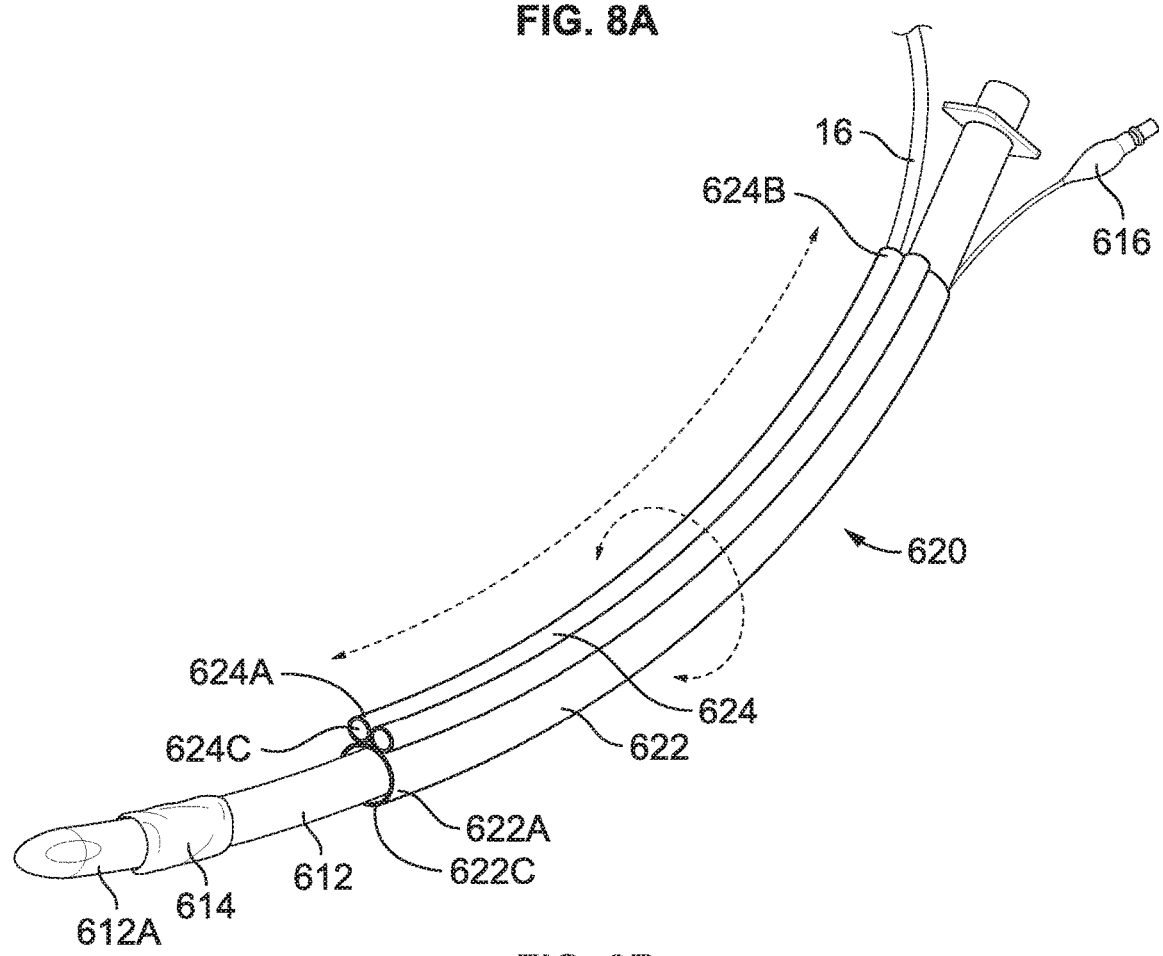
FIG. 8B depicts the adaptor of FIG. 8A being combined with an endotracheal tube and camera.

Referring to FIG. 8B, it depicts the endotracheal tube 612 and the camera 12 loaded into the adaptor 620. As can be seen from the assembly in FIG. 8B, the camera 12 placed in the tube 624 can provide a continuous visualization during placement of the endotracheal tube 12. If placement of the endotracheal tube 12 needs to be guided with a tool, the tool can be inserted into the third hollow channel, 626.

As shown in FIG. 8B, the adaptor 620 can rotate around the endotracheal tube 612 clock-wise and/or counter-clockwise. This allows to 5 move the camera 12 and/or tools as needed. The adaptor 620 can also slide along the distal-proximal 612A-612B axis of the endotracheal tube 612. This allows additional flexibility in combining the camera and/or tools closer or further away from the distal end 612A of the endotracheal tube 612.

The adaptor 620 can be used with a variety of endotracheal tubes and/or other devices as a diameter of the hollow tube 622 and the diameters of the hollow tubes 624 and 626 can be designed to accommodate various devices.

Figure 8C:
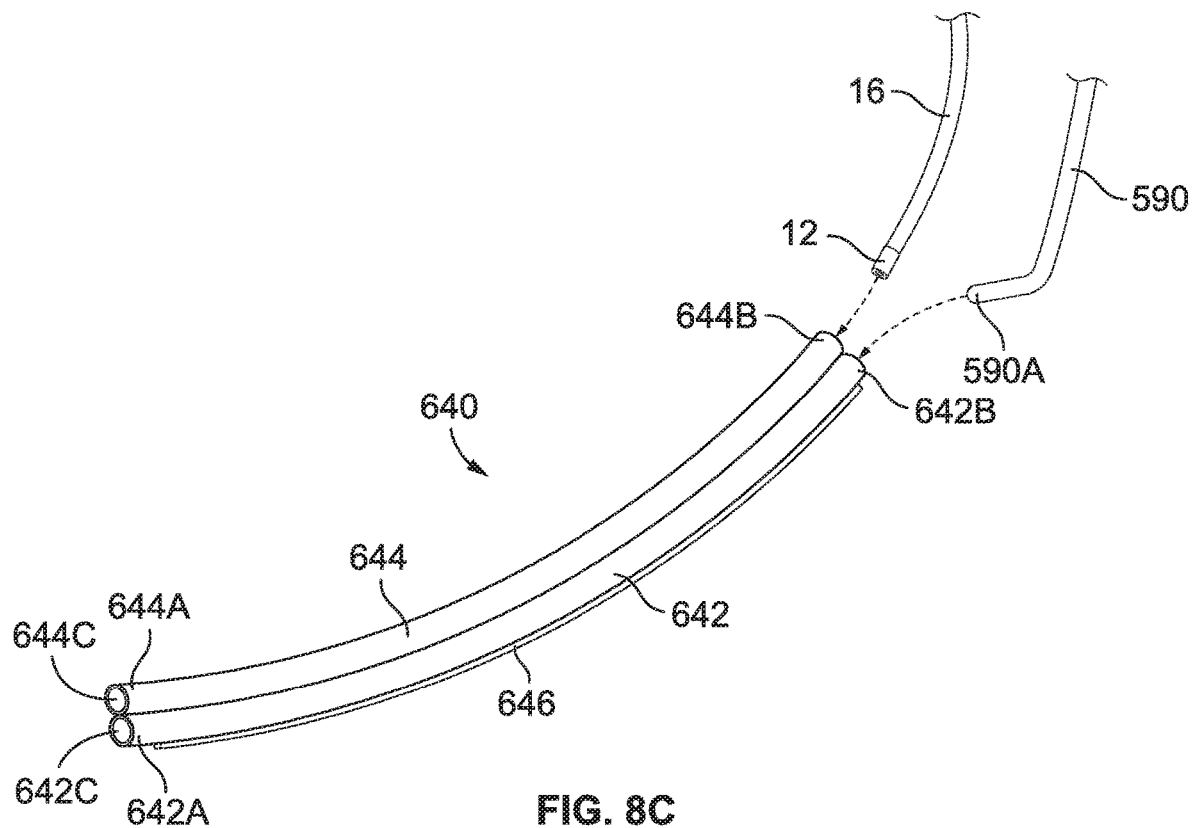
FIG. 8C depicts another embodiment of an adaptor comprising two hollow tubes and a backbone rod.

Referring to FIG. 8C, it depicts a further embodiment of an adaptor according to this disclosure, generally 640. The adaptor 640 comprises a hollow tube 642 with a distal end 642A and a proximal end 642B. The hollow tube 642 has an opening 642C at the distal end 642A and an opening 642D (not shown in the drawing of FIG. 8C) at the proximal end 642B.

At least one second hollow tube 644 is attached to the hollow tube 642. The second hollow tube 644 has a distal end 644A and a proximal end 644B. In other embodiments, the adaptor 640 may comprise a plurality of second hollow tubes 644, for example, 2 or 3 or 4 of the second hollow tubes 644.

The second hollow tube 644 has an opening 644C at the distal end 644A. The second hollow tube 644 has an opening 644D at the proximal end 644B. The distal end 644A of the second hollow tube 644 is aligned with the distal end 642A of the hollow tube 642. The proximal end 644B of the second hollow tube 644 is aligned with the proximal end 642B of the hollow tube 642. A diameter of the second hollow tube 624 is compatible with a camera 12 such that the camera 12 connected to the cable 16 can be inserted through the proximal opening 644D into the second hollow tube 644. Since the distal end 644C is not sealed, the camera 12 can protrude distally from the second hollow tube 644. A bougie 590 or any other tool or tube, i.e. an endotracheal tube, can be placed in the hollow tube 642.

The adaptor 640 may further comprise a stylet or rod 646 which runs along the hollow tube 642 for at least some of the length of the hollow tube 642 and provides a support and backbone to the adaptor 640. In further embodiments, the rod 646 is not present.

Figure 8D:
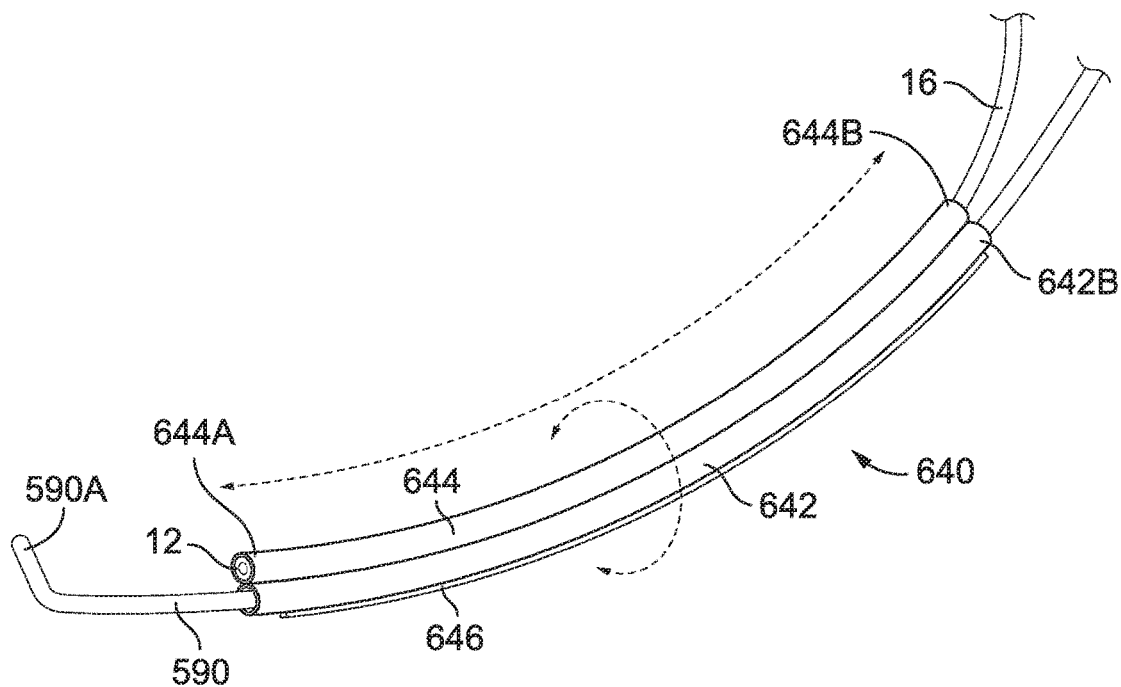
FIG. 8D depicts a bougie and camera being inserted into the adaptor of FIG. 8C.

As shown in FIG. 8D, the camera 12 is loaded into the second hollow tube 644, while the bougie 590 is loaded into the hollow tube 642 of the adaptor 640. The adaptor 640 can rotate clock-wise and counter-clockwise around the bougie. The adaptor 640 can slide distally and proximally along the bougie. This allow visualization of different tissue areas as needed.

Figure 8E:
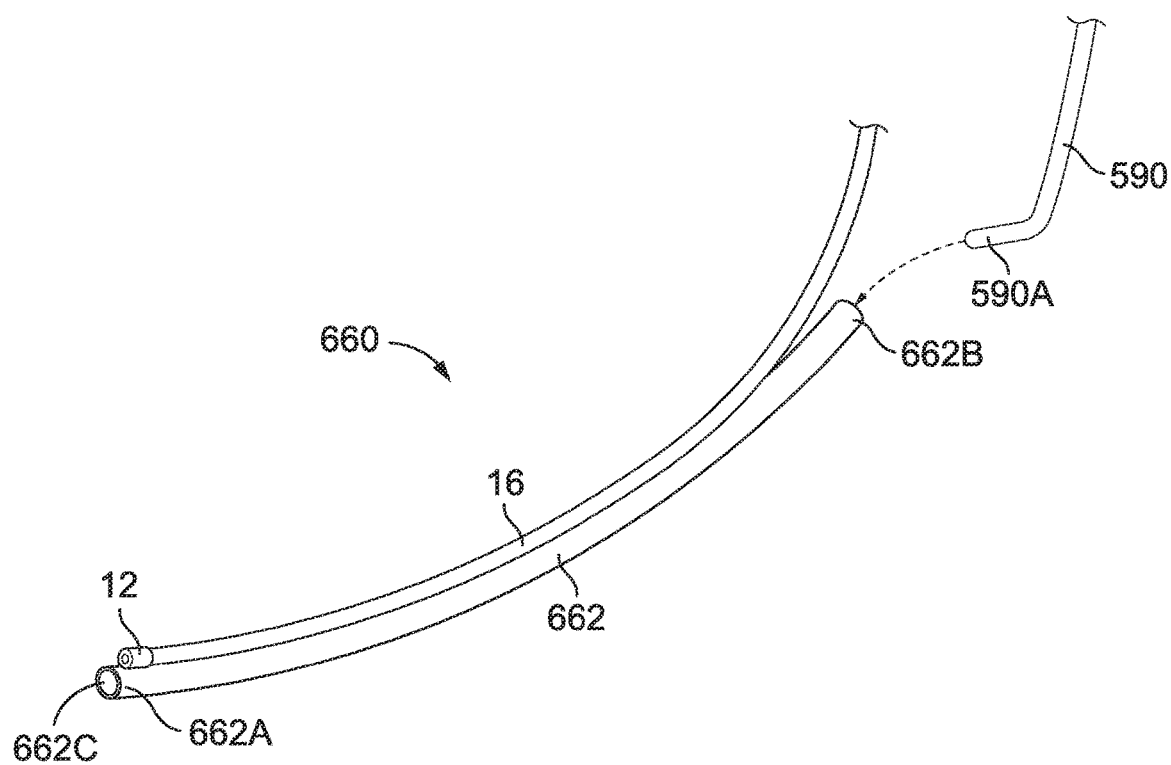
FIG. 8E depicts another embodiment of an adaptor comprising a hollow tube attached to a camera.

Referring to FIG. 8E, it provides a further embodiment of an adaptor according to this disclosure, generally 660. The adaptor 660 comprises a hollow tube 662 attached to the camera 12. The hollow tube 662 comprises a distal end 662A and a proximal end 662B. The camera 12 is attached to the hollow tube 662 externally and in proximity with the distal end 662A. The cable 16 runs along the length of the hollow tube 662.

Figure 8F:
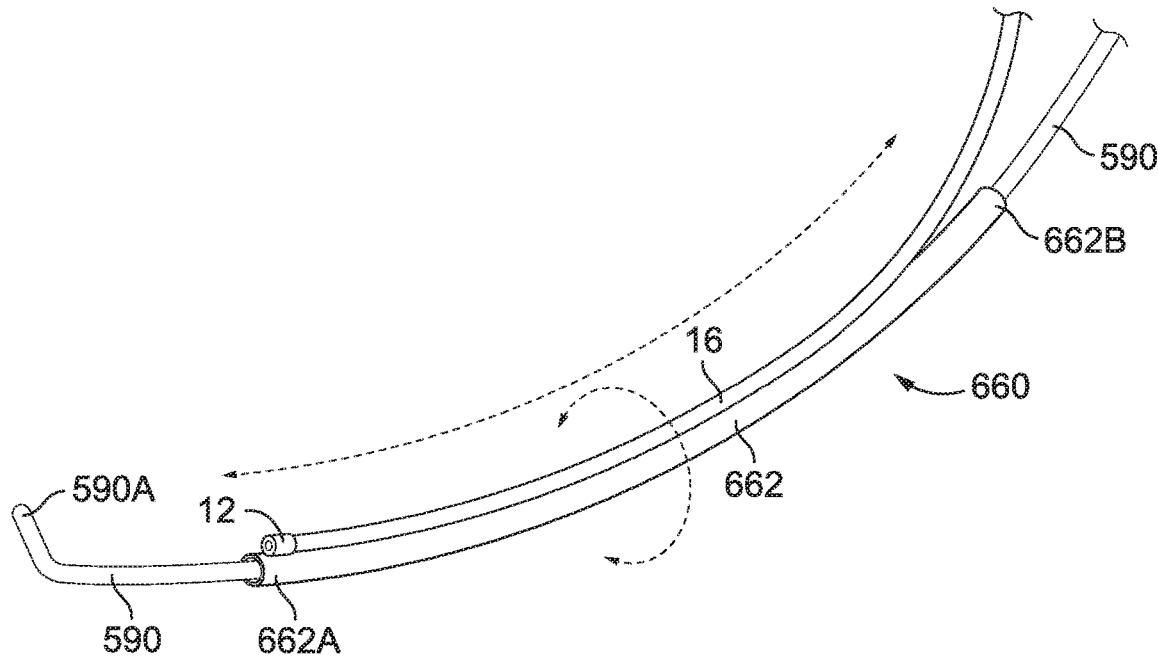
FIG. 8F depicts a bougie being inserted into the adaptor of FIG. 8E.

A bougie 590, or some other tool, can be placed into the hollow tube 662 as shown in FIG. 8F. The adaptor 660 can rotate clockwise and counter-clockwise around the bougie 590. The adaptor 660 can also slide distally and proximally along the length of the bougie 590. The adaptor 660 may comprise additional hollow tubes as was described in connection with adaptors 620 and 640.

Figure 8G:
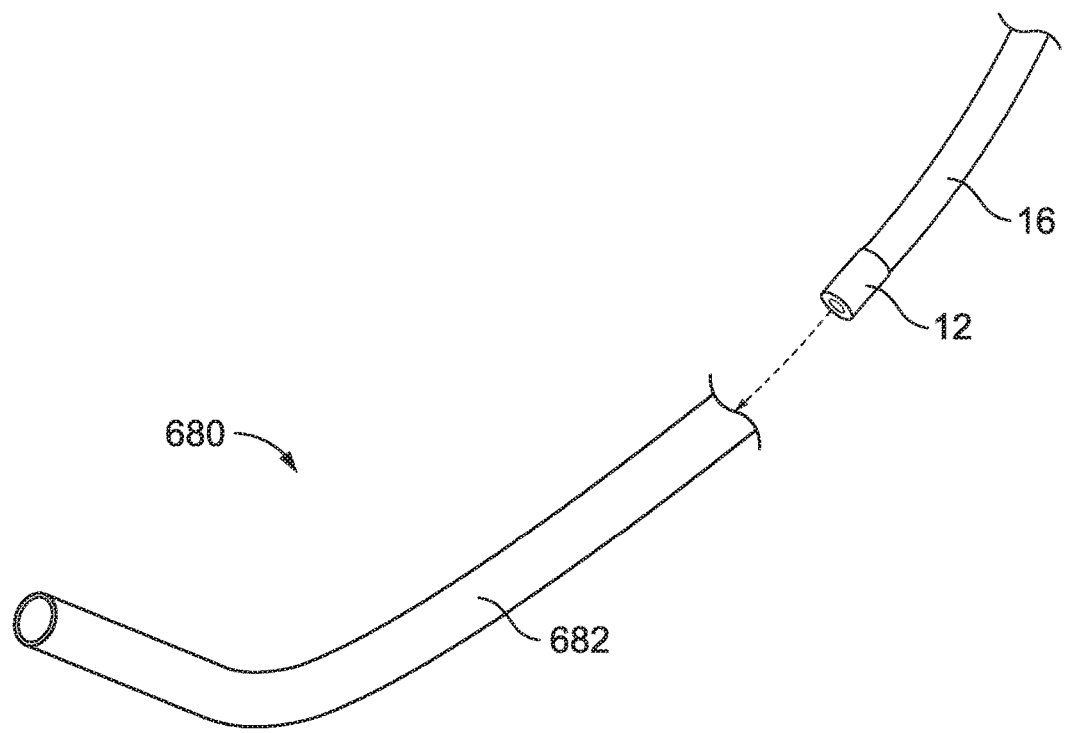
FIG. 8G depicts another embodiment of an adaptor according to this disclosure.
Figure 8H:
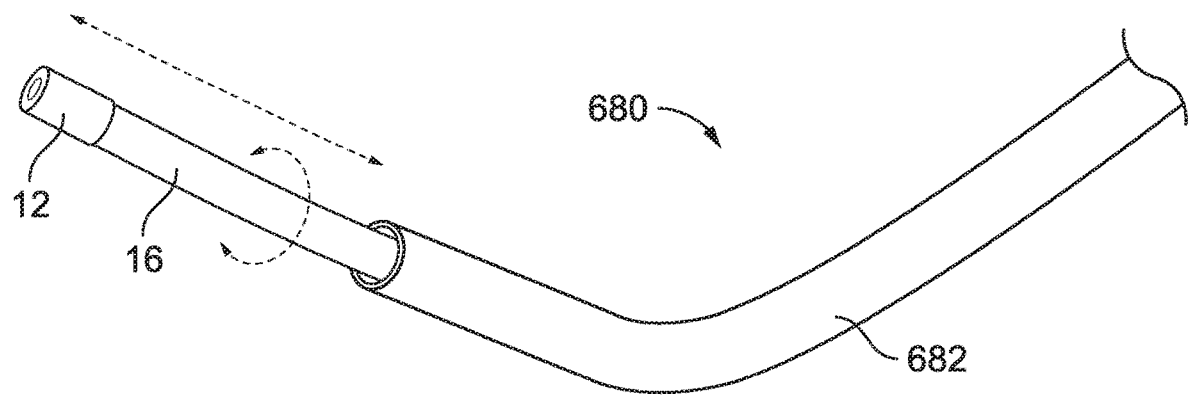
FIG. 8H depicts a camera being inserted and rotated in the adaptor of FIG. 8G.

Referring to FIG. 8G, it provides a further embodiment of an adaptor according to this disclosure, generally 680. The adaptor 680 comprises a hollow tube 682, a portion of which is shown in FIG. 8G. The camera 12 with cable 16 can be inserted into the hollow tube 682. The hollow tube 282 is made of a plastic material which flexible enough to be curved into a shape needed for insertion. However, once curved, the hollow tube 282 will retain the shape. Any of the adaptors provided in this disclosure can be made of this material and have the property of retaining a shape they have been placed into. In alternative, an adaptor according to this disclosure can be made of a flexible material. FIG. 8H depicts the camera 12 inserted into the adaptor 680.

In further aspects, this disclosure provides kits or systems for managing patient's airways. The kits/systems may comprise at least one of the devices described in this disclosure and further comprising additional tools and/or materials. These kits may include the oral airway device 460, 510, 520, 530, 540, 560, 580, and/or 600 together with any of the following: the adaptor 500, the ventilator adaptor 507, the camera 12, the plug 546, the bougie 590, the adaptor 620, the adaptor 640, the adaptor 660, the adaptor 680, or any combination thereof. The kit/system may further comprise other tools and/or a manual. Any of the devices described in this disclosure may be made in different sizes in order to accommodate pediatric patients and adult patients of different body weights.

In further aspects, this disclosure provides methods for managing patient airways, including ventilating and monitoring a patient. In these methods, at least one of the oral airway devices 460, 510, 520, 530, 540, 560, 580, and/or 600 is combined with at least a camera and preferably at least with a camera and a tool, such as for example a stylet or bougie, which can assist in placement of the oral airway device 460, 510, 520, 530, 540, 560, 580, and/or 600 into a patient. The oral airway devices may be also combined with a suction tube and/or a monitor of patient's heart tones and sounds. Any of these assemblies are then inserted into the patient's oral cavity and the oral airway device is then positioned in the patient's pharynx. If needed, a closed system can be established by using any of the cuffs 476, 494, 542, and/or the adaptors 500, 507, and/or plugs 546. The assembly is then connected to a ventilator and the patient is ventilated through the ETT lumen 468 or one of the channels 584, 586 and/or 588.

If a patient must be intubated, an endotracheal tube can be loaded into the ETT lumen of the oral airway device 460, 510, 520, 530, 540 or 560. The assembly can then deliver the endotracheal tube to the patient's trachea and ensure its proper placement.

The insertion of the oral airway device 460, 510, 520, 530, 540, 560, 580, and/or 600 into the patient's oral cavity then can be conducted by one single practitioner under continuous visualization from one or more cameras which ensures accurate and rapid placement of the device into the patient's pharynx. If the oral airway device 460, 510, 520, 530, 540 or 560 carries an endotracheal tube, the oral airway device 460, 510, or 520, 530 can be easily separated and removed through the slit in the endotracheal lumen from the endotracheal tube while the endotracheal tube still remains inserted and in place in the patient. These methods avoid repetitive intubation/extubation.

After the intubation has been completed, the intubated patient can be monitored continuously with the camera(s) and also for heart tones and sounds and/or temperature as needed.

The present devices and methods can be used for intubating patients who are difficult to intubate and also for patients with damaged airways. The present devices and methods are suitable for monitoring a patient for an adverse reaction such as for example, vomiting and/or obstruction.

While certain medical devices are described above, a person of skill would appreciate that this invention also includes embodiments with various obvious modifications as would be easily apparent to a person of skill.

What is claimed is:
1. An adaptor for use with a medical device, the adaptor consisting of:
   a hollow tube with a distal end opening and a proximal end opening, the hollow tube having a diameter compatible for insertion of the medical device into the hollow tube, wherein the medical device is an endotracheal tube with a proximal end and a distal end or a bougie; and
   a camera attached to the hollow tube externally, the camera being in proximity to the distal end of the hollow tube, the camera having a cable; and
   wherein the adaptor is sized for rotating around the endotracheal tube and sliding along the distal-proximal axis of the endotracheal tube when the adaptor is in use in a patient.
2. The adaptor of claim 1, wherein the hollow tube has a slit.

* * * * *